United States Patent [19]
Pierce et al.

[11] Patent Number: 6,015,701
[45] Date of Patent: *Jan. 18, 2000

[54] N-ACETYLGLUCOSAMINYLTRANSFERASE V PROTEINS AND CODING SEQUENCES

[75] Inventors: James Michael Pierce, Athens; Mohamed G. Shoreibah, Comer, both of Ga.; Beverly Adler, Newbury Park, Calif.; Nevis Lee Fregien, Miami, Fla.

[73] Assignees: University of Georgia Research Foundation, Inc., Athens, Ga.; Amgen, Inc., Thousand Oaks, Calif.

[ * ] Notice: This patent is subject to a terminal disclaimer.

[21] Appl. No.: 08/276,968

[22] Filed: Jul. 19, 1994

Related U.S. Application Data

[63] Continuation-in-part of application No. 08/016,863, Feb. 10, 1993, Pat. No. 5,602,003, which is a continuation-in-part of application No. 07/905,795, Jun. 29, 1992, abandoned.

[51] Int. Cl.$^7$ .......................... C12N 15/54; C12N 15/74; C12N 15/85
[52] U.S. Cl. ...................... 435/193; 435/325; 435/252.3; 435/252.33; 435/320.1; 536/23.2
[58] Field of Search ........................ 536/23.2; 435/320.1, 435/240.2, 252.3, 252.33, 193, 325

[56] References Cited

U.S. PATENT DOCUMENTS 5,032,519  7/1991  Paulson et al. .......................... 435/193

FOREIGN PATENT DOCUMENTS 0585109  3/1994  European Pat. Off. .

OTHER PUBLICATIONS

Saito et al. (1994) "cDNA Cloning and Chromosomal Mapping of Human N–acetylglucosaminyltransferase V", *Biochem. & Biophys. Res, Comm.* 198:318–327.
Gu et al. (1993) "Purification and Characterization of UDP–N–Acetylglucosamine: α–6–D–Maanoside β1–6N–Acetylglucosaminyltransferase (N–Acetylglucosaminyltransferase V) from a Human Lung Cancer Cell Line", *J. Biochem.* 113:614–619.
Shoreibah et al. (1993) "Isolation, Characterization, and Expression of a cDNA Encoding N–Acetylglucosoaminyltransferase V", *J. Biol. Chem.* 21(268):15381–15385.
Miyoshi et al. (1993) "N–Acetylglucosaminyltransferase III and V Messenger RNA Levels in LEC Rats during Hepatocarcinogenesis", *Cancer Research* 53:3899–3902.
Palcic et al. (1990) "Regulation of N–Acetylglucosaminyltransferase V Activity", *J. Biol. Chem.* 265:6759–6769.
Pierce et al. (1987) "Activity of UDP–GLCNAC:α–Mannoside β(1,6)N–Acetylglucosaminytransferase (GnT V) in Cultured Cells Using a Synthetic Trisaccharide Acceptor", *Biochem. Biophys. Res. Commun.* 146:679–684.
Bendiak et al. (1987) "Control of Glycoprotein Synthesis", *J. Biol. Chem.* 262(12):5784–5790.
Oppenheimer et al. (1981) "Purification and Characterization of a Rabbit Liver α1→3 Mannoside β1→2 N–Acetylglucosaminyltransferase", *J. Biol. Chem.* 256(2):799–804.
Frohman et al. (1988) "Rapid Production of Full–length cDNAs from Rare Transcripts: Amplification Using a Single Gene–specific Oligonucleotide Primer", *Proc. Natl. Acad. Sci. USA* 85:8998–9002.
Larsen et al. (1989) "Isolation of cDNA Encoding a Murine UDP galactose:β–D–galactosyl–1,4–N–acetyl–D–glucosaminide α–1,3–galactosyltransferase: Expression Cloning by Gene Transfer" *Proc Natl. Acad. Sci. USA* 86:8227–8231.
Shoreibah et al. (1990) "Purification of Rat Kidney UDP–N–Acetylglucosamine:α Mannoside β(1,6)N–Acetylglucosaminyltransferase (GlcNAc–TV)", *J. Cell Biol.* 111(5): Part 2, Abstract 1103.
Moreman et al. (1991) "Isolation, Characterization, and Expression of CDNAs Encoding Murine α–Mannoside II, a Golgi Enzyme That Controls Conversion of High Mannose to Complex N–Glycans", *J. Cell. Biol.* 115:1521–1534.
Weinstein et al. (1987) "Primary Structure of β–galactoside α2,6–Sialyltransferase", *J. Biol. Chem.* 262:17735–17743.
Colley et al. (1989) "Conversion of a Golgi Apparatus Sialyltransferase to a Secretory Protein by Replacement of the NH$_2$–terminal Signal Anchor with a Signal Peptide", *J. Biol. Chem.* 264:17619–17622.
Larsen et al. (1990) "Molecular Cloning, Sequence, and Expression of Human GDP–L–fucose: β–D–galactoside 2–α–L–fucosyltransferase cDNA that can Form the H Blood Group Antigen", *Proc. Natl. Acad. Sci. USA* 87:6674–6678.
Barker et al. (1972) "Agarose Derivatives of Uridine Diphosphate and N–acetylglucosamine for the Purification of A Galactosyltransferase", *J. Biol. Chem.* 247:7135–7147.
Pinto et al. (1983) "Preparation of Glycoconjugates for use as Artificial Antigens: a Simplified Procedure", *Carbohydr. Res.* 124:313–318.
Wen et al. (1992) "Neu Differentiation Factor A Transmembrane Glycoprotein Containing an EGF Domain and an Immunoglobulin Homology Unit", *Cell* 69:599–572.
Shoreibah et al. (1992) "Purification and Characterization of Rat Kidney UDP–N–acetylglucosamine:α–6–D–Mannoside β–1,6–N–Acetylglucosaminyltransferase", *J. Biol. Chem* 267:2920–2927.
Shoreibah et al. (1991) "Purification and Characterization of Rat Kidney N–Acetylgucosaminyltransferase–V", *Glycoconjugate J.* 8:260.

*Primary Examiner*—Charles L. Patterson, Jr.
*Attorney, Agent, or Firm*—Greenlee, Winner and Sullivan, PC

[57] ABSTRACT

The present invention provides substantially purified UDP-N-acetylglucosamine: α-6-D-mannoside β-1,6-N-acetylglucosaminyl transferase (GlcNAc T-V; EC 2.4.1.155) proteins and antibodies which specifically bind GlcNAc T-V. The present invention also provides polynucleotide sequences and oligonucleotide probes capable of specifically hybridizing to nucleic acid sequences which encode GlcNAc T-V, and cDNA and genomic clones encoding GlcNAc T-V, as well as nucleotide sequences encoding GlcNAc T-V, as specifically exemplified by GlcNAc T-V coding sequences from rat, hamster, mouse and human.

31 Claims, 20 Drawing Sheets

```
                                                        T
GACCCCGCTCCTGGCTGTGCCTGGGACCCCAGTTCCCAGGAGCACGGTTGCAGGAGAGTG              61

ACCCCGACTGCTACTGATGGTGCTTCTGCTGCTCCTCTACTAGCAGGAGTGACTCCTACC            121

CAGAAGTGGACTTGGAGGAGGGTCCGTTAGACCATCAGAATGGAAGCCCGACAAGCAAGT            181

CAGCTGACTCAGGAACCAGAGTGAGGGCCACGCACTCTCCGCCCCAGCCTGCACCATGAA            241

CTTGCCTTCCCCTTCTGCTTGTTGAGAGCCAAGGGAATGGTACATTACTAGAGAGAGATG            301
                                                             Met
                                                              1

GCTTTCTTTTCTCCCTGGAAGTTGTCCTCTCAGAAGCTGGGCTTTTTCTTGGTGACTTTT            361
AlaPhePheSerProTrpLysLeuSerSerGlnLysLeuGlyPhePheLeuValThrPhe

GGCTTCATATGGGGGATGATGCTTCTACACTTCACCATCCAGCAGCGAACTCAGCCTGAG            421
GlyPheIleTrpGlyMetMetLeuLeuHisPheThrIleGlnGlnArgThrGlnProGlu

AGCAGCTCCATGTTGCGGGAGCAAATCCTTGACCTCAGCAAAAGGTACATTAAGGCACTG            481
SerSerSerMetLeuArgGluGlnIleLeuAspLeuSerLysArgTyrIleLysAlaLeu
                      50

GCAGAAGAGAACAGGAACGTGGTGGATGGCCCGTATGCCGGTGTCATGACAGCCTATGAT
AlaGluGluAsnArgAsnValValAspGlyProTyrAlaGlyValMetThrAlaTyrAsp

CTGAAGAAAACGCTCGCCGTGCTGCTGGATAACATCTTGCAGCGCATCGGCAAGCTGGAG            601
LeuLysLysThrLeuAlaValLeuLeuAspAsnIleLeuGlnArgIleGlyLysLeuGlu
                                                           100

TCCAAGGTGGACAATCTTGTCAACGGCACAGGAGCGAATTCTACCAACTCCACCACGGCT            661
SerLysValAspAsnLeuValAsnGlyThrGlyAlaAsnSerThrAsnSerThrThrAla
                    *              *              *
                   109            114            117

GTCCCCAGCTTGGTGTCACTGGAGAAAATTAATGTGGCAGATATCATTAATGGAGTTCAA            721
ValProSerLeuValSerLeuGluLysIleAsnValAlaAspIleIleAsnGlyValGln

GAAAAATGTGTATTGCCTCCTATGGATGGCTACCCCCACTGCGAGGGGAAAATCAAGTGG            781
GluLysCysValLeuProProMetAspGlyTyrProHisCysGluGlyLysIleLysTrp
                              150

ATGAAAGACATGTGGCGGTCAGACCCCTGCTACGCAGACTATGGAGTGGACGGGACCTCC            841
MetLysAspMetTrpArgSerAspProCysTyrAlaAspTyrGlyValAspGlyThrSer

TGCTCCTTTTTTATTTACCTCAGTGAGGTTGAAAATTGGTGTCCTCGTTTACCTTGGAGA            901
CysSerPhePheIleTyrLeuSerGluValGluAsnTrpCysProArgLeuProTrpArg
                                                           200

GCAAAAAATCCCTATGAAGAAGCTGACCATAACTCATTGGCAGAAATCCGCACGGATTTT            961
AlaLysAsnProTyrGluGluAlaAspHisAsnSerLeuAlaGluIleArgThrAspPhe
```

FIG. 10A

```
AACATTCTCTACGGCATGATGAAGAAGCATGAGGAGTTCCGGTGGATGAGACTTCGGATC     1021
AsnIleLeuTyrGlyMetMetLysLysHisGluGluPheArgTrpMetArgLeuArgIle

CGGCGAATGGCTGATGCATGGATCCAAGCAATCAAGTCTCTGGCAGAGAAACAAAACCTA     1081
ArgArgMetAlaAspAlaTrpIleGlnAlaIleLysSerLeuAlaGluLysGlnAsnLeu
                            250

GAGAAGAGGAAACGGAAGAAAATCCTTGTTCACCTGGGGCTCCTGACCAAGGAATCAGGC     1141
GluLysArgLysArgLysLysIleLeuValHisLeuGlyLeuLeuThrLysGluSerGly

TTCAAGATTGCAGAGACAGCATTCAGCGGTGGCCCTCTCGGCGAGCTCGTTCAGTGGAGT     1201
PheLysIleAlaGluThrAlaPheSerGlyGlyProLeuGlyGluLeuValGlnTrpSer
                                                     300

GACTTAATCACATCTCTGTACCTGCTGGGCCATGACATCCGCATCTCAGCCTCGCTGGCT     1261
AspLeuIleThrSerLeuTyrLeuLeuGlyHisAspIleArgIleSerAlaSerLeuAla

GAGCTCAAGGAGATTATGAAGAAGGTTGTTGGAAACCGGTCTGGCTGTCCAACTGTAGGA     1321
GluLeuLysGluIleMetLysLysValValGlyAsnArgSerGlyCysProThrValGly
                                         *
                                        333

GACAGAATCGTTGAGCTTATTTATATCGATATTGTGGGACTTGCTCAATTCAAGAAAACG     1381
AspArgIleValGluLeuIleTyrIleAspIleValGlyLeuAlaGlnPheLysLysThr
                                                  350

CTAGGACCATCCTGGGTTCATTACCAGTGCATGCTCCGGGTGCTGGACTCCTTTGGAACA     1441
LeuGlyProSerTrpValHisTyrGlnCysMetLeuArgValLeuAspSerPheGlyThr

GAACCTGAGTTCAATCACGCAAGTTACGCCCAGTCGAAAGGCCACAAGACCCCCTGGGGA     1501
GluProGluPheAsnHisAlaSerTyrAlaGlnSerLysGlyHisLysThrProTrpGly
                                                         400

AAGTGGAATCTGAACCCGCAACAGTTTTACACCATGTTCCCTCATACCCCAGACAACAGC     1561
LysTrpAsnLeuAsnProGlnGlnPheTyrThrMetPheProHisThrProAspAsnSer

TTTCTGGGCTTCGTGGTCGAGCAGCACCTGAACTCCAGCGACATCCACCACATTAACGAG     1621
PheLeuGlyPheValValGluGlnHisLeuAsnSerSerAspIleHisHisIleAsnGlu
                                        *
                                       432

ATCAAAAGGCAGAACCAGTCCCTTGTGTATGGCAAAGTGGATAGTTTCTGGAAGAATAAG     1681
IleLysArgGlnAsnGlnSerLeuValTyrGlyLysValAspSerPheTrpLysAsnLys
                 *                450
                446

AAGATCTACTTGGACATCATTCACACGTACATGGAAGTGCACGCCACTGTTTACGGCTCC     1741
LysIleTyrLeuAspIleIleHisThrTyrMetGluValHisAlaThrValTyrGlySer

AGTACCAAGAACATCCCCAGTTACGTGAAAAACCATGGCATTCTCAGCGGCCGTGACCTA     1801
SerThrLysAsnIleProSerTyrValLysAsnHisGlyIleLeuSerGlyArgAspLeu
                                                          500
```

FIG. 10B

```
CAGTTTCTTCTCCGGGAAACCAAGCTTTTTGTTGGGCTTGGATTCCCTTATGAAGGTCCA         1861
GlnPheLeuLeuArgGluThrLysLeuPheValGlyLeuGlyPheProTyrGluGlyPro

GCTCCCCTGGAAGCCATCGCGAATGGATGTGCTTTCCTGAACCCCAAGTTCAACCCTCCT         1921
AlaProLeuGluAlaIleAlaAsnGlyCysAlaPheLeuAsnProLysPheAsnProPro

AAAAGCAGCAAAAACACAGACTTCTTCATTGGCAAGCCAACACTGAGAGAGCTCACATCC         1981
LysSerSerLysAsnThrAspPhePheIleGlyLysProThrLeuArgGluLeuThrSer
                                                 550

CAGCACCCGTACGCAGAAGTCTTCATCGGCCGGCCACACGTCTGGACCGTGGACCTCAAT         2061
GlnHisProTyrAlaGluValPheIleGlyArgProHisValTrpThrValAspLeuAsn

AACCGAGAGGAAGTAGAAGACGCAGTAAAAGCCATCTTAAACCAGAAGATTGAGCCGTAT         2101
AsnArgGluGluValGluAspAlaValLysAlaIleLeuAsnGlnLysIleGluProTyr
                                                 600

ATGCCATATGAGTTCACATGTGAAGGCATGCTGCAGAGAATCAACGCTTTCATCGAGAAA         2161
MetProTyrGluPheThrCysGluGlyMetLeuGlnArgIleAsnAlaPheIleGluLys

CAGGACTTCTGCCACGGCCAAGTGATGTGGCCGCCCCTTAGCGCCCTGCAGGTGAAGCTG         2221
GlnAspPheCysHisGlyGlnValMetTrpProProLeuSerAlaLeuGlnValLysLeu

GCTGAGCCCGGGCAGTCCTGCAAACAGGTGTGCCAGGAGAGCCAGCTCATCTGCGAGCCG         2281
AlaGluProGlyGlnSerCysLysGlnValCysGlnGluSerGlnLeuIleCysGluPro
                                                 650

TCCTTCTTCCAGCACCTCAACAAGGAAAAGGACCTGCTGAAGTATAAGGTAATCTGCCAA         2341
SerPhePheGlnHisLeuAsnLysGluLysAspLeuLeuLysTyrLysValIleCysGln

AGCTCAGAACTATACAAGGACATCCTGGTGCCCTCCTTCTACCCCAAGAGCAAGCACTGT         2401
SerSerGluLeuTyrLysAspIleLeuValProSerPheTyrProLysSerLysHisCys
                                                 700

GTGTTCCAAGGGGATCTCCTGCTCTTCAGTTGTGCCGGGGCCCACCCCACACACCAGCGG         2461
ValPheGlnGlyAspLeuLeuLeuPheSerCysAlaGlyAlaHisProThrHisGlnArg

ATCTGCCCCTGCCGGGACTTCATCAAGGGCCAAGTGGCCCTCTGCAAAGACTGCCTATAG         2521
IleCysProCysArgAspPheIleLysGlyGlnValAlaLeuCysLysAspCysLeuEnd

CATAGCCACCCTGGATTCATTCAGATGGGAAGACGTGGCTCCGCTGGGCAGGGCCGAGG          2581

GGCTGAAAGACAGTCAGGGACTCTGACCAGAGCCTGAAATCTT
```

FIG. 10C

Human, Cho, Mouse and Rat GlcNAc T-V Nucleotide Sequence Comparison

```
            1                                                      50
RatTV       TGACCCCGCT CCTGGCTGTG CCTGGGACCC CAGTTCCCAG GAGCACGGTT 51                                                     100
RatTV       GCAGGAGAGT GACCCCGACT GCTACTGATG GTGCTTCTGC TGCTCCTCTA 101                                                    150
RatTV       CTAGCAGGAG TGACTCCTAC CCAGAAGTGG ACTTGGAGGA GGGTCCGTTA 151                                                    200
ChoTV            AGCAGA ATGGAAGCCA GGCAAGGAAA TCAGCTGACT CAGGAGCCGG
RatTV       GACCATCAGA ATGGAAGCCC GACAAGCAAG TCAGCTGACT CAGGAACCAG 201                                                    250
ChoTV       AGTGAGAGCG ACACACCCTC CGCCCCAGCC TGCACCATGA ACTTGCCTTC
RatTV       AGTGAGGGCC ACGCACTCTC CGCCCCAGCC TGCACCATGA ACTTGCCTTC 251                                                    300
HumanTV                GTTAAGAGC CAAGGACAGG TGAAGTTGCC AGAGAGCAAT
ChoTV       ACCTTCTGCA CGTTGAGAGC CAAGGGAGGG GTACATTGCC AGAGAGAGAT
RatTV       CCCTTCTGCT TGTTGAGAGC CAAGGGAATG GTACATTACT AGAGAGAGAT 301                                                    350
HumanTV     GGCTCTCTTC ACTCCGTGGA AGTTGTCCTC TCAGAAGCTG GCTTTTTCC
ChoTV       GGCTTTCTTT ACTCCCTGGA AGTTGTCCTC TCAGAAGCTA GCTTTTTCT
RatTV       GGCTTTCTTT TCTCCCTGGA AGTTGTCCTC TCAGAAGCTG GCTTTTTCT 351                                                    400
HumanTV     TGGTGACTTT TGGCTTCATT TGGGGTATGA TGCTTCTGCA CTTTACCATC
ChoTV       TGGTGACTTT TGGCTTTATA TGGGGGATGA TGCTTCTGCA CTTCACCATC
RatTV       TGGTGACTTT TGGCTTCATA TGGGGGATGA TGCTTCTACA CTTCACCATC 401                                                    450
HumanTV     CAGCAGCGAA CTCAGCCTGA AAGCAGCTCC ATGCTGCGCG AGCAGATCCT
ChoTV       CAGCAGCGGA CTCAGCCTGA GAGCAGCTCC ATGTTGCGGG AGCAAATCCT
RatTV       CAGCAGCGAA CTCAGCCTGA GAGCAGCTCC ATGTTGCGGG AGCAAATCCT 451                                                    500
HumanTV     GGACCTCAGC AAAAGGTACA TCAAGGCACT GGCAGAAGAA AACAGGAATG
ChoTV       GGATCTCAGC AAAAGGTACA TCAAAGCACT GGCAGAAGAA AACAGAAACG
RatTV       TGACCTCAGC AAAAGGTACA TTAAGGCACT GGCAGAAGAG AACAGGAACG 501                                                    550
HumanTV     TGGTGGATGG GCCATACGCT GGAGTCATGA CAGCTTATGA TCTGAAGAAA
ChoTV       TGGTGGATGG ACCATACGCT GGCGTCATGA CAGCTTATGA TCTGAAGAAA
RatTV       TGGTGGATGG CCCGTATGCC GGTGTCATGA CAGCCTATGA TCTGAAGAAA 551                                                    600
HumanTV     ACCCTTGCTG TGTTATTAGA TAACATTTTG CAGCGCATTG GCAAGTTGGA
ChoTV       ACACTTGCTG TACTACTAGA TAACATCTTG CAACGCATTG GCAAGCTCGA
RatTV       ACGCTCGCCG TGCTGCTCGA TAACATCTTG CAGCGCATCG GCAAGCTGGA 601                                                    650
HumanTV     GTCGAAGGTG GACAATCTTG TTGTCAATGG CACCGGAACA AACTCAACCA
ChoTV       GTCGAAGGTG GACAATCTCG T...CAATGG CACAGGAGCA AATTCTACCA
RatTV       GTCCAAGGTG GACAATCTTG T...CAACGG CACAGGAGCG AATTCTACCA
```

FIG. 11A

```
         651                                                  700
HumanTV  ACTCCACTAC AGCTGTTCCC AGCTTGGTTG CACTTGAGAA AATTAATGTG
  ChoTV  ACTCCACCAC AGCTGTCCCC AGCTTGGTAT CGCTTGAAAA AATTAGTGTG
  RatTV  ACTCCACCAC GGCTGTCCCC AGCTTGGTGT CACTGGAGAA AATTAATGTG 701                                                  750
HumanTV  GCAGATATCA TTAACGGAGC TCAAGAAAAA TGTGTATTGC CTCCTATGGA
  ChoTV  GCAGATATCA TTAATGGAGT TCAAGAAAAA TGTGTATTGC CTCCTATGGA
  RatTV  GCAGATATCA TTAATGGAGT TCAAGAAAAA TGTGTATTGC CTCCTATGGA 751                                                  800
HumanTV  CGGCTACCCT CACTGTGAGG GAAAGATCAA GTGGATGAAA GACATGTGGC
  ChoTV  TGGCTACCCC CACTGCGAGG GGAAAATCAA GTGGATGAAA GACATGTGGC
  RatTV  TGGCTACCCC CACTGCGAGG GGAAAATCAA GTGGATGAAA GACATGTGGC 801                                                  850
HumanTV  GTTCAGATCC CTGCTACGCA GACTATGGAG TGGATGGATC CACCTGCTCT
  ChoTV  GCTCGGATCC CTGCTACGCA GACTATGGAG TGGACGGCAC CTCCTGCTCC
  RatTV  GGTCAGACCC CTGCTACGCA GACTATGGAG TGGACGGGAC CTCCTGCTCC 851                                                  900
HumanTV  TTTTTTATTT ACCTCAGTGA GGTTGAAAAT TGGTGTCCTC ATTTACCTTG
  ChoTV  TTTTTTATTT ACCTCAGTGA GGTTGAAAAT TGGTGTCCTC GTTTACCTTG
  RatTV  TTTTTTATTT ACCTCAGTGA GGTTGAAAAT TGGTGTCCTC GTTTACCTTG 901                                                  950
HumanTV  GAGAGCAAAA AATCCCTACG AAGAAGCTGA TCATAATTCA TTGGCGGAAA
  ChoTV  GAGAGCAAAA AATCCCTATG AAGAAGCTGA TCATAACTCA TTGGCGGAAA
  RatTV  GAGAGCAAAA AATCCCTATG AAGAAGCTGA CCATAACTCA TTGGCAGAAA 951                                                 1000
HumanTV  TTCGTACAGA TTTTAATATT CTCTACAGTA TGATGAAAAA GCATGAAGAA
  ChoTV  TCCGTACGGA TTTTAACATT CTCTACAGCA TGATGAAGAA GCATGAGGAG
  RatTV  TCCGCACGGA TTTTAACATT CTCTACGGCA TGATGAAGAA GCATGAGGAG 1001                                                1050
HumanTV  TTCCGGTGGA TGAGACTACG GATCCGGCGA ATGGCTGACG CATGGATCCA
  ChoTV  TTCCGGTGGA TGAGACTTCG GATCCGGCGA ATGGCTGATG CGTGGATCCA
  RatTV  TTCCGGTGGA TGAGACTTCG GATCCGGCGA ATGGCTGATG CATGGATCCA 1051                                                1100
HumanTV  AGCAATCAAG TCCCTGGCAG AAAAGCAGAA CCTTGAAAAG AGAAAGCGGA
  ChoTV  AGCAATCAAG TCTCTGGCAG AGAAACAAAA CCTGGAAAAG AGAAAACGGA
  RatTV  AGCAATCAAG TCTCTGGCAG AGAAACAAAA CCTAGAGAAG AGGAAACGGA 1101                                                1150
HumanTV  AGAAAGTCCT CGTTCACCTG GGACTCCTGA CCAAGGAATC TGGATTTAAG
  ChoTV  AGAAAATCCT TGTTCACCTG GGGCTCCTGA CCAAGGAATC TGGCTTCAAG
  RatTV  AGAAAATCCT TGTTCACCTG GGGCTCCTGA CCAAGGAATC AGGCTTCAAG 1151                                                1200
HumanTV  ATTGCAGAGA CAGCTTTCAG TGGTGGCCCT CTTGGTGAAT TAGTTCAATG
  ChoTV  ATTGCAGAGA CGGCATTCAG TGGTGGCCCT CTTGGCGAAC TGGTTCAGTG
MouseTV              GA CAGCATTCAG CGGTGGCCCT CTGGGTGAAC TCGTTCAGTG
  RatTV  ATTGCAGAGA CAGCATTCAG CGGTGGCCCT CTCGGCGAGC TCGTTCAGTG
```

FIG. 11B

|          | 1201       |            |            |            | 1250       |
|----------|------------|------------|------------|------------|------------|
| HumanTV  | GAGTGATTTA | ATTACATCTC | TGTACTTACT | GGGCCATGAC | ATTAGGATTT |
| ChoTV    | GAGTGACTTA | ATTACATCTC | TCTACCTACT | GGGCCATGAC | ATCCGGATCT |
| MouseTV  | GAGTGACTTA | ATCACATCTC | TGTACCTGCT | GGGCCATGAC | ATCCGGATCT |
| RatTV    | GAGTGACTTA | ATCACATCTC | TGTACCTGCT | GGGCCATGAC | ATCCGCATCT |

|          | 1251       |            |            |            | 1300       |
|----------|------------|------------|------------|------------|------------|
| HumanTV  | CAGCTTCACT | GGCTGAGCTC | AAGGAAATCA | TGAAGAAGGT | TGTAGGAAAC |
| ChoTV    | CGGCTTCACT | GGCTGAGCTA | AAGGAGATTA | TGAAGAAGGT | TGTTGGAAAT |
| MouseTV  | CGGCCTCACT | GGCTGAGCTC | AAGGAGATAA | TGAAGAAGGT | TGTTGGAAAC |
| RatTV    | CAGCCTCGCT | GGCTGAGCTC | AAGGAGATTA | TGAAGAAGGT | TGTTGGAAAC |

|          | 1301       |            |            |            | 1350       |
|----------|------------|------------|------------|------------|------------|
| HumanTV  | CGATCTGGCT | GCCCAACTGT | AGGAGACAGA | ATTGTTGAGC | TCATTTACAT |
| ChoTV    | CGGTCTGGCT | GTCCCACTGT | AGGAGACAGA | ATCGTTGAGC | TTATTTATAT |
| MouseTV  | CGGTCTGGCT | GTCCAACTGT | AGGAGACAGA | ATCGTTGAGC | TGATTTATAT |
| RatTV    | CGGTCTGGCT | GTCCAACTGT | AGGAGACAGA | ATCGTTGAGC | TTATTTATAT |

|          | 1351       |            |            |            | 1400       |
|----------|------------|------------|------------|------------|------------|
| HumanTV  | TGATATTGTA | GGACTTGCTC | AATTCAAGAA | AACTCTTGGA | CCATCCTGGG |
| ChoTV    | TGATATTGTG | GGACTTGCTC | AATTTAAGAA | AACTCTAGGA | CCATCCTGGG |
| MouseTV  | CGATATTGTG | GGACTTGCTC | AATTTAAGAA | AACACTAGGG | CCATCCTGGG |
| RatTV    | CGATATTGTG | GGACTTGCTC | AATTCAAGAA | AACGCTAGGA | CCATCCTGGG |

|          | 1401       |            |            |            | 1450       |
|----------|------------|------------|------------|------------|------------|
| HumanTV  | TTCATTACCA | GTGCATGCTC | CGAGTCCTTG | ATTCATTTGG | TACTGAACCC |
| ChoTV    | TTCACTACCA | GTGCATGCTC | CGAGTGCTAG | ATTCCTTTGG | AACAGAACCT |
| MouseTV  | TTCATTACCA | GTGCATGCTC | CGGGTGCTAG | ACTCCTTTGG | AACAGAACCT |
| RatTV    | TTCATTACCA | GTGCATGCTC | CGGGTGCTGG | ACTCCTTTGG | AACAGAACCT |

|          | 1451       |            |            |            | 1500       |
|----------|------------|------------|------------|------------|------------|
| HumanTV  | GAATTTAATC | ATGCAAATTA | TGCCCAATCG | AAAGGCCACA | AGACCCCTTG |
| ChoTV    | GAGTTCAATC | ATGCAAGTTA | TGCCCAGTCG | AAAGGCCACA | AGACCCCCTG |
| MouseTV  | GAGTTCAATC | ATGCGAGCTA | TGCCCAGTCA | AAAGGCCACA | AGACCCCCTG |
| RatTV    | GAGTTCAATC | ACGCAAGTTA | CGCCCAGTCG | AAAGGCCACA | AGACCCCCTG |

|          | 1501       |            |            |            | 1550       |
|----------|------------|------------|------------|------------|------------|
| HumanTV  | GGGAAAATGG | AATCTGAACC | CTCAGCAGTT | TTATACCATG | TTCCCTCATA |
| ChoTV    | GGGAAAATGG | AATCTGAACC | CGCAGCAGTT | TTACACCATG | TTCCCTCACA |
| MouseTV  | GGGAAAGTGG | AATCTGAACC | CGCAGCAGTT | TTACACCATG | TTCCCTCATA |
| RatTV    | GGGAAAGTGG | AATCTGAACC | CGCAACAGTT | TTACACCATG | TTCCCTCATA |

|          | 1551       |            |            |            | 1600       |
|----------|------------|------------|------------|------------|------------|
| HumanTV  | CCCCAGACAA | CAGCTTTCTG | GGGTTTGTGG | TTGAGCAGCA | CCTGAACTCC |
| ChoTV    | CCCCAGATAA | CAGCTTCCTG | GGCTTCGTGG | TCGAGCAGCA | CCTGAACTCT |
| MouseTV  | CCCCAGACAA | CAGCTTTCTG | GGCTTCGTGG | TGGAGCAGCA | CCTGAACTCC |
| RatTV    | CCCCAGACAA | CAGCTTTCTG | GGCTTCGTGG | TCGAGCAGCA | CCTGAACTCC |

|          | 1601       |            |            |            | 1650       |
|----------|------------|------------|------------|------------|------------|
| HumanTV  | AGTGATATCC | ACCACATTAA | TGAAATCAAA | AGGCAGAACC | AGTCCCTTGT |
| ChoTV    | AGCGACATCC | ACCACATTAA | TGAGATCAAA | AGGCAGAACC | AGTCCCTTGT |
| MouseTV  | AGCGACATTC | ACCACATCAA | CGAGATCAAA | AGGCAGAACC | AGTCCCTTGT |
| RatTV    | AGCGACATCC | ACCACATTAA | CGAGATCAAA | AGGCAGAACC | AGTCCCTTGT |

|          | 1651       |            |            |            | 1700       |
|----------|------------|------------|------------|------------|------------|
| HumanTV  | GTATGGCAAA | GTGGATAGCT | TCTGGAAGAA | TAAGAAGATC | TACTTGGACA |
| ChoTV    | GTATGGCAAA | GTGGATAGTT | TCTGGAAGAA | TAAGAAAATC | TACTTGGATA |
| MouseTV  | GTATGGCAAA | GTGGATAGTT | TCTGGAAGAA | TAAGAAAATC | TACCTGGATA |
| RatTV    | GTATGGCAAA | GTGGATAGTT | TCTGGAAGAA | TAAGAAGATC | TACTTGGACA |

FIG. 11C

```
         1701                                                1750
HumanTV  TTATTCACAC ATACATGGAA GTGCATGCAA CTGTTTATGG CTCCAGCACA
ChoTV    TCATTCACAC GTACATGGAA GTTCATGCCA CTGTTTACGG CTCCAGCACA
MouseTV  TCATTCACAC GTACATGGAA GTGCACGCCA CTGTTTATGG CTCCAGTACC
RatTV    TCATTCACAC GTACATGGAA GTGCACGCCA CTGTTTACGG CTCCAGTACC 1751                                                1800
HumanTV  AAGAATATTC CCAGTTACGT GAAAAACCAT GGTATCCTCA GTGGACGGGA
ChoTV    AAGAACATTC CCAGTTACGT GAAAAATCAT GGCATTCTCA GTGGGCGTGA
MouseTV  AAGAACATTC CCAGTTACGT GAAAAACCAT GGCATTCTCA GTGGACGTGA
RatTV    AAGAACATCC CCAGTTACGT GAAAAACCAT GGCATTCTCA GCGGCCGTGA 1801                                                1850
HumanTV  CCTGCAGTTC CTTCTTCGAG AAACCAAGTT GTTTGTTGGA CTTGGGTTCC
ChoTV    CCTGCAGTTT CTTCTCCGGG AAACAAAGCT GTTTGTTGGG CTGGGATTCC
MouseTV  CCTGCAGTTT CTTCTCCGGG AAACCAAGCT GTTCGTTGGG CTCGGATTCC
RatTV    CCTACAGTTT CTTCTCCGGG AAACCAAGCT TTTTGTTGGG CTTGGATTCC 1851                                                1900
HumanTV  CTTACGAGGG CCCAGCTCCC CTGGAAGCTA TCGCAAATGG ATGTGCTTTT
ChoTV    CTTATGAGGG TCCAGCTCCC CTAGAGGCCA TTGCAAATGG ATGTGCTTTC
MouseTV  CTTATGAAGG CCCAGCTCCC CTGGAGGCCA TCGCGAATGG ATGTGCTTTC
RatTV    CTTATGAAGG TCCAGCTCCC CTGGAAGCCA TCGCGAATGG ATGTGCTTTC 1901                                                1900
HumanTV  CTGAATCCCA AGTTCAACCC ACCCAAAAGC AGCAAAAACA CAGACTTTTT
ChoTV    CTGAACCCCA AGTTCAGCCC TCCCAAGAGC AGCAAAAATA CAGACTTCTT
MouseTV  CTGAACCCCA AGTTCAACCC TCCCAAAAGC AGCAAAAACA CAGACTTCTT
RatTV    CTGAACCCCA AGTTCAACCC TCCTAAAAGC AGCAAAAACA CAGACTTCTT 1951                                                2000
HumanTV  CATTGGCAAG CCAACTCTGA GAGAGCTGAC ATCCCAGCAT CCTTACGCTG
ChoTV    CATTGGCAAG CCGACCCTGA GAGAGCTGAC GTCTCAGCAC CCTTATGCAG
MouseTV  CATTGGCAAG CCAACACTGA GAGAGCTGAC ATCCCAGCAT CCTTACGCAG
RatTV    CATTGGCAAG CCAACACTGA GAGAGCTCAC ATCCCAGCAC CCGTACGCAG 2001                                                2050
HumanTV  AAGTTTTCAT CGGGCGGCCA CATGTGTGGA CTGTTGACCT CAACAATCAG
ChoTV    AAGTCTTCAT CGGCCGGCCA CACGTCTGGA CCGTGGATCT GAACAATCGA
MouseTV  AAGTCTTCAT CGGCCGGCCA CACGTCTGGA CTGTGGATCT CAATAACCGA
RatTV    AAGTCTTCAT CGGCCGGCCA CACGTCTGGA CCGTGGACCT CAATAACCGA 2051                                                2100
HumanTV  GAGGAAGTAG AGGATGCAGT GAAAGCAATT TTAAATCAGA AGATTGAGCC
ChoTV    GAGGAAGTAG AGGATGCCGT GAAAGCCATC TTAAACCAGA AGATTGAGCC
MouseTV  GAGGAAGTAG AAGATGCAGT AAAAGCCATC TTAAACCAGA AGATTGAGCC
RatTV    GAGGAAGTAG AAGACGCAGT AAAAGCCATC TTAAACCAGA AGATTGAGCC 2101                                                2150
HumanTV  ATACATGCCA TATGAATTTA CGTGCGAGGG GATGCTACAG AGAATCAATG
ChoTV    GTATATGCCG TATGAGTTCA CATGTGAAGG GATGCTGCAG AGAATCAACG
MouseTV  GTATATGCCA TATGAGTTCA CATGTGAAGG CATGCTGCAG AGAATCAACG
RatTV    GTATATGCCA TATGAGTTCA CATGTGAAGG CATGCTGCAG AGAATCAACG 2151                                                2200
HumanTV  CTTTCATTGA AAAACAGGAC TTCTGCCATG GGCAAGTGAT GTGGCCACCC
ChoTV    CGTTCATAGA GAAGCAGGAC TTCTGCCATG GCCAGGTGAT GTGGCCTCCC
MouseTV  CTTTCATTGA AAAACAGGAC TTCTGCCATG GCCAAGTGAT GTGGCCGCCC
RatTV    CTTTCATCGA GAAACAGGAC TTCTGCCACG GCCAAGTGAT GTGGCCGCCC
```

FIG. 11D

```
                    2201                                              2250
HumanTV   CTCAGCGCCC TACAGGTCAA GCTTGCTGAG CCCGGGCAGT CCTGCAAGCA
  ChoTV   CTGAGCGCCT TGCAGGTGAA GCTGGCTGAG CCTGGGCAGT CCTGCAAGCA
MouseTV   CTCAGCGCCC TGCAGGTTAA GCTGGCTGAG CCAGGGCAGT CCTGCAAACA
  RatTV   CTTAGCGCCC TGCAGGTGAA GCTGGCTGAG CCCGGGCAGT CCTGCAAACA 2251                                              2300
HumanTV   GGTGTGCCAG GAGAGCCAGC TCATCTGCGA GCCTTCTTTC TTCCAGCACC
  ChoTV   AGTGTGCCAG GAGAACCAGC TCATCTGTGA GCCATCCTTC TTCCAGCACC
MouseTV   GGTGTGCCAG GAGAGCCAGC TCATCTGCGA GCCATCCTTC TTTCAACACC
  RatTV   GGTGTGCCAG GAGAGCCAGC TCATCTGCGA GCCGTCCTTC TTCCAGCACC 2301                                              2350
HumanTV   TCAACAAGGA CAAGGACATG CTGAAGTACA AGGTGACCTG CCAAAGCTCA
  ChoTV   TCAACAAGGA AAAGGACTTG CTGAAGTACA GAGTGACCTG CCAAAGCTCA
MouseTV   TCAACAAGGA AAAGGACCTG CTGAAGTATA AGGTGACCTG CCAAAGCTCA
  RatTV   TCAACAAGGA AAAGGACCTG CTGAAGTATA AGGTAATCTG CCAAAGCTCA 2351                                              2400
HumanTV   GAGCTGGCCA AGGACATCCT GGTGCCCTCC TTTGACCCTA AGAATAAGCA
  ChoTV   GAACTGTACA AGGACATCCT GGTGCCATCC TTCTACCCCA AGAGCAAGCA
MouseTV   GAACTGTACA AGGACATCCT GGTGCCCTCC TTCTACCCCA AGAGCAAGCA
  RatTV   GAACTATACA AGGACATCCT GGTGCCCTCC TTCTACCCCA AGAGCAAGCA 2401                                              2450
HumanTV   CTGTGTGTTT CAAGGTGACC TCCTGCTCTT CAGCTGTGCA GGCGCCCACC
  ChoTV   CTGTGTGCTC CAAGGGGATC TCCTGCTCTT CAGTTGTGCC GGGGCCCACC
MouseTV   CTGTGTGTTC CAAGGGGACC TCCTGCTCTT CAGTTGTGCC GGAGCCCATC
  RatTV   CTGTGTGTTC CAAGGGGATC TCCTGCTCTT CAGTTGTGCC GGGGCCCACC 2451                                              2500
HumanTV   CCAGGCACCA GAGGGTCTGC CCCTGCCGGG ACTTCATCAA GGGCCAGGTG
  ChoTV   CCACACACCA GAGGATCTGC CCCTGCCGGG ACTTCATCAA GGGCCAAGTG
MouseTV   CCACACACCA GCGGATCTGC CCCTGCCGGG ACTTCATCAA GGGCCAAGTG
  RatTV   CCACACACCA GCGGATCTGC CCCTGCCGGG ACTTCATCAA GGGCCAAGTG 2501                                              2550
HumanTV   GCTCTCTGCA AAGACTGCCT ATAGCAGCTA CCTGCTCAGC CCTGCACCAT
  ChoTV   GCCCTATGCA AAGACTGCCT ATA
MouseTV   GCCCTCTGCA AAGACTGCCT ATAGCATCGC TGCCCTGAAT TAACTCAGAC
  RatTV   GCCCTCTGCA AAGACTGCCT ATAGCATAGC CACCCTGGAT TCATTCAGAT 2551                                              2600
HumanTV   GCTGCTGGGG AAGACAGTGG CCCCAGCCCC CTCAGGCAGG GCCAGGGACA
MouseTV   GGGAAAGACG TGGCTCCACT GGGCAGGGCC AAGGGGCACA AAGACATTCA
  RatTV   GGGAAAGACG TGGCTCCGCT GGGCAGGGCC GAGGGGCTGA AGACAGTCA 2601                                              2650
HumanTV   GAAGTCATGC AGGGACTCTG GCAAGAGCCT GAACTTTTTC GTAGAAGGTT
MouseTV   GGGACTCTGA CCAGAGCCTG AGATCTTTGG TCCAGGGCTT GAGTTTAGTA
  RatTV   GGGACTCTGA CCAGAGCCTG AAATCTT 2651                                              2700
HumanTV   CTGAATTGGC ATTGCCCTTG CTGCACTCCG AGCAACCCAG TGGAGTCTTC
MouseTV   CCGCTCCAGC CACAGCCAGT GCATCCCAGT TTACACCAAA ACCACAAGGG 2701                                              2750
HumanTV   ACCAAAACAA AACAAGAGCG TATGTCAGGC CAGGAGCCTG GCCTGTCCCT
MouseTV   AACAGGTTAG AACAGGAACC TGGGTTCTCC TCAGTGTAAG GAATGTCCTC
```

FIG. 11E

```
         2751                                                   2800
HumanTV  GGCACAACAT CATTTCTGTT TCTCAAGGAG CAACTGTGGG AAGACTGTCA
MouseTV  TCTGTCTGGG AGATCGAGCG ACTGTAGGGA AAGGATCCAG GCAGTTGCTC 2801                                                   2850
HumanTV  CTGCAGCTGC TCCAGGGCAA AAGAA
MouseTV  CCGGGAATTT TTTTTTTTTT TTTTTTTAAA GAAGGGATAA AAGTCCGGAG
```

FIG. 11F

Human, Cho, Mouse and Rat GlcNAcT-V
Amino Acid Sequence Comparison

```
                     1                                                              50
        HumanTV    MALFTPWKLS SQKLGFFLVT FGFIWGMMLL HFTIQQRTQP ESSSMLREQI
          ChoTV    MAFFTPWKLS SQKLGFFLVT FGFIWGMMLL HFTIQQRTQP ESSSMLREQI
          RatTV    MAFFSPWKLS SQKLGFFLVT FGFIWGMMLL HFTIQQRTQP ESSSMLREQI 51                                                             100
        HumanTV    LDLSKRYIKA LAEENRNVVD GPYAGVMTAY DLKKTLAVLL DNILQRIGKL
          ChoTV    LDLSKRYIKA LAEENRNVVD GPYAGVMTAY DLKKTLAVLL DNILQRIGKL
          RatTV    LDLSKRYIKA LAEENRNVVD GPYAGVMTAY DLKKTLAVLL DNILQRIGKL 101                                                             150
        HumanTV    ESKVDNLVVN GTGTNSTNST TAVPSLVALE KINVADIING AQEKCVLPPM
          ChoTV    ESKVDNLV.N GTGANSTNST TAVPSLVSLE KISVADIING VQEKCVLPPM
          RatTV    ESKVDNLV.N GTGANSTNST TAVPSLVSLE KINVADIING VQEKCVLPPM 151                                                             200
        HumanTV    DGYPHCEGKI KWMKDMWRSD PCYADYGVDG STCSFFIYLS EVENWCPHLP
          ChoTV    DGYPHCEGKI KWMKDMWRSD PCYADYGVDG TSCSFFIYLS EVENWCPRLP
          RatTV    DGYPHCEGKI KWMKDMWRSD PCYADYGVDG TSCSFFIYLS EVENWCPRLP 201                                                             250
        HumanTV    WRAKNPYEEA DHNSLAEIRT DFNILYSMMK KHEEFRWMRL RIRRMADAWI
          ChoTV    WRAKNPYEEA DHNSLAEIRT DFNILYSMMK KHEEFRWMRL RIRRMADAWI
          RatTV    WRAKNPYEEA DHNSLAEIRT DFNILYGMMK KHEEFRWMRL RIRRMADAWI 251                                                             300
        HumanTV    QAIKSLAEKQ NLEKRKRKKV LVHLGLLTKE SGFKIAETAF SGGPLGELVQ
          ChoTV    QAIKSLAEKQ NLEKRKRKKI LVHLGLLTKE SGFKIAETAF SGGPLGELVQ
        MouseTV                                                TAF SGGPLGELVQ
          RatTV    QAIKSLAEKQ NLEKRKRKKI LVHLGLLTKE SGFKIAETAF SGGPLGELVQ 301                                                             350
        HumanTV    WSDLITSLYL LGHDIRISAS LAELKEIMKK VVGNRSGCPT VGDRIVELIY
          ChoTV    WSDLITSLYL LGHDIRISAS LAELKEIMKK VVGNRSGCPT VGDRIVELIY
        MouseTV    WSDLITSLYL LGHDIRISAS LAELKEIMKK VVGNRSGCPT VGDRIVELIY
          RatTV    WSDLITSLYL LGHDIRISAS LAELKEIMKK VVGNRSGCPT VGDRIVELIY 351                                                             400
        HumanTV    IDIVGLAQFK KTLGPSWVHY QCMLRVLDSF GTEPEFNHAN YAQSKGHKTP
          ChoTV    IDIVGLAQFK KTLGPSWVHY QCMLRVLDSF GTEPEFNHAS YAQSKGHKTP
        MouseTV    IDIVGLAQFK KTLGPSWVHY QCMLRVLDSF GTEPEFNHAS YAQSKGHKTP
          RatTV    IDIVGLAQFK KTLGPSWVHY QCMLRVLDSF GTEPEFNHAS YAQSKGHKTP 401                                                             450
        HumanTV    WGKWNLNPQQ FYTMFPHTPD NSFLGFVVEQ HLNSSDIHHI NEIKRQNQSL
          ChoTV    WGKWNLNPQQ FYTMFPHTPD NSFLGFVVEQ HLNSSDIHHI NEIKRQNQSL
        MouseTV    WGKWNLNPQQ FYTMFPHTPD NSFLGFVVEQ HLNSSDIHHI NEIKRQNQSL
          RatTV    WGKWNLNPQQ FYTMFPHTPD NSFLGFVVEQ HLNSSDIHHI NEIKRQNQSL
```

FIG. 12A

```
           451                                                        500
HumanTV    VYGKVDSFWK NKKIYLDIIH TYMEVHATVY GSSTKNIPSY VKNHGILSGR
  ChoTV    VYGKVDSFWK NKKIYLDIIH TYMEVHATVY GSSTKNIPSY VKNHGILSGR
MouseTV    VYGKVDSFWK NKKIYLDIIH TYMEVHATVY GSSTKNIPSY VKNHGILSGR
  RatTV    VYGKVDSFWK NKKIYLDIIH TYMEVHATVY GSSTKNIPSY VKNHGILSGR 501                                                        550
HumanTV    DLQFLLRETK LFVGLGFPYE GPAPLEAIAN GCAFLNPKFN PPKSSKNTDF
  ChoTV    DLQFLLRETK LFVGLGFPYE GPAPLEAIAN GCAFLNPKFS PPKSSKNTDF
MouseTV    DLQFLLRETK LFVGLGFPYE GPAPLEAIAN GCAFLNPKFN PPKSSKNTDF
  RatTV    DLQFLLRETK LFVGLGFPYE GPAPLEAIAN GCAFLNPKFN PPKSSKNTDF 551                                                        600
HumanTV    FIGKPTLREL TSQHPYAEVF IGRPHVWTVD LNNQEEVEDA VKAILNQKIE
  ChoTV    FIGKPTLREL TSQHPYAEVF IGRPHVWTVD LNNREEVEDA VKAILNQKIE
MouseTV    FIGKPTLREL TSQHPYAEVF IGRPHVWTVD LNNREEVEDA VKAILNQKIE
  RatTV    FIGKPTLREL TSQHPYAEVF IGRPHVWTVD LNNREEVEDA VKAILNQKIE 601                                                        650
HumanTV    PYMPYEFTCE GMLQRINAFI EKQDFCHGQV MWPPLSALQV KLAEPGQSCK
  ChoTV    PYMPYEFTCE GMLQRINAFI EKQDFCHGQV MWPPLSALQV KLAEPGQSCK
MouseTV    PYMPYEFTCE GMLQRINAFI EKQDFCHGQV MWPPLSALQV KLAEPGQSCK
  RatTV    PYMPYEFTCE GMLQRINAFI EKQDFCHGQV MWPPLSALQV KLAEPGQSCK 651                                                        700
HumanTV    QVCQESQLIC EPSFFQHLNK DKDMLKYKVT CQSSELAKDI LVPSFDPKNK
  ChoTV    QVCQENQLIC EPSFFQHLNK EKDLLKYRVT CQSSELYKDI LVPSFYPKSK
MouseTV    QVCQESQLIC EPSFFQHLNK EKDLLKYKVT CQSSELYKDI LVPSFYPKSK
  RatTV    QVCQESQLIC EPSFFQHLNK EKDLLKYKVT CQSSELYKDI LVPSFYPKSK 701                                              742
HumanTV    HCVFQGDLLL FSCAGAHPRH QRVCPCRDFI KGQVALCKDC L*
  ChoTV    HCVLQGDLLL FSCAGAHPTH QRICPCRDFI KGQVALCKDC L*
MouseTV    HCVFQGDLLL FSCAGAHPTH QRICPCRDFI KGQVALCKDC L*
  RatTV    HCVFQGDLLL FSCAGAHPTH QRICPCRDFI KGQVALCKDC L*
```

FIG. 12B

SEQUENCE LISTING (1) GENERAL INFORMATION:

(iii) NUMBER OF SEQUENCES: 34

(2) INFORMATION FOR SEQ ID NO:1:

(i) SEQUENCE CHARACTERISTICS:
      (A) LENGTH: 12 amino acids
      (B) TYPE: amino acid
      (C) STRANDEDNESS: single
      (D) TOPOLOGY: linear (ii) MOLECULE TYPE: peptide (iii) HYPOTHETICAL: NO (iv) ANTI-SENSE: NO (v) FRAGMENT TYPE: internal (xi) SEQUENCE DESCRIPTION: SEQ ID NO:1:

Asn Thr Asp Phe Phe Ile Gly Lys Pro Thr Leu Arg
1          5                  10

(2) INFORMATION FOR SEQ ID NO:2:

(i) SEQUENCE CHARACTERISTICS:
      (A) LENGTH: 16 amino acids
      (B) TYPE: amino acid
      (C) STRANDEDNESS:
      (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:2:

Ala Ile Leu Asn Gln Lys Ile Glu Pro Tyr Met Pro Tyr Glu Phe Thr
1          5                  10               15

(2) INFORMATION FOR SEQ ID NO:3:

(i) SEQUENCE CHARACTERISTICS:
      (A) LENGTH: 12 amino acids
      (B) TYPE: amino acid
      (C) STRANDEDNESS:
      (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:3:

Val Leu Asp Ser Phe Gly Thr Glu Pro Glu Phe Asn
1               5                  10

(2) INFORMATION FOR SEQ ID NO:4:

(i) SEQUENCE CHARACTERISTICS:
           (A) LENGTH: 10 amino acids
           (B) TYPE: amino acid
           (C) STRANDEDNESS: single
           (D) TOPOLOGY: linear (ii) MOLECULE TYPE: peptide (iii) HYPOTHETICAL: NO (v) FRAGMENT TYPE: internal (xi) SEQUENCE DESCRIPTION: SEQ ID NO:4:

Ser Asp Pro Cys Tyr Ala Asp Tyr Glu Val
1               5                  10

(2) INFORMATION FOR SEQ ID NO:5:

(i) SEQUENCE CHARACTERISTICS:
           (A) LENGTH: 29 base pairs
           (B) TYPE: nucleic acid
           (C) STRANDEDNESS: single
           (D) TOPOLOGY: linear (ii) MOLECULE TYPE: other nucleic acid
           (A) DESCRIPTION: /desc = ""N is inosine at positions
                6 and 21.""

(iii) HYPOTHETICAL: NO (xi) SEQUENCE DESCRIPTION: SEQ ID NO:5:

AAYACNGAYT TYTTYATHGG NAARCCNAC                                            29

(2) INFORMATION FOR SEQ ID NO:6:

(i) SEQUENCE CHARACTERISTICS:
           (A) LENGTH: 29 base pairs
           (B) TYPE: nucleic acid
           (C) STRANDEDNESS: single
           (D) TOPOLOGY: linear (ii) MOLECULE TYPE: other nucleic acid
           (A) DESCRIPTION: /desc = ""N is inosine at positions
                3, 9 and 24.""

(iii) HYPOTHETICAL: NO (iv) ANTI-SENSE: YES (xi) SEQUENCE DESCRIPTION: SEQ ID NO:6:

GTNGGYTTNC CDATRAARAA RTCNGTRTT                                            29

(2) INFORMATION FOR SEQ ID NO:7:

(i) SEQUENCE CHARACTERISTICS:
           (A) LENGTH: 29 base pairs
           (B) TYPE: nucleic acid
           (C) STRANDEDNESS: single
           (D) TOPOLOGY: linear (ii) MOLECULE TYPE: other nucleic acid
        (A) DESCRIPTION: /desc = "I is inosine at positions
            3, 9 and 24."

(iii) HYPOTHETICAL: NO (iv) ANTI-SENSE: NO (xi) SEQUENCE DESCRIPTION: SEQ ID NO:7:

ATHGARCCNT AYATGCCNTA YGARTTYAC                              29

(2) INFORMATION FOR SEQ ID NO:8:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "I is inosine at positions 6
            and 15."

(iii) HYPOTHETICAL: NO (iv) ANTI-SENSE: YES (xi) SEQUENCE DESCRIPTION: SEQ ID NO:8:

TCRTANGGCA TRTANGGYTC DATYTTYTG                              29

(2) INFORMATION FOR SEQ ID NO:9:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:9:

GGGCCGATGA AGACTTCTGC G                                     21

(2) INFORMATION FOR SEQ ID NO:10:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:10:

GGGCTACTTC CTCTCGGTTA TTGAG                                 25

(2) INFORMATION FOR SEQ ID NO:11:

(i) SEQUENCE CHARACTERISTICS:
        (A) LENGTH: 23 base pairs
        (B) TYPE: nucleic acid
        (C) STRANDEDNESS: single
        (D) TOPOLOGY: linear

```
        (ii) MOLECULE TYPE: other nucleic acid (iii) HYPOTHETICAL: NO (iv) ANTI-SENSE: NO (xi) SEQUENCE DESCRIPTION: SEQ ID NO:11:

GCTCTAATAC GACTCACTAT AGG                                                23

(2) INFORMATION FOR SEQ ID NO:12:

(i) SEQUENCE CHARACTERISTICS:
              (A) LENGTH: 27 base pairs
              (B) TYPE: nucleic acid
              (C) STRANDEDNESS: single
              (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:12:

GGGTACGTGT GAATGATATC CAGGTAG                                            27

(2) INFORMATION FOR SEQ ID NO:13:

(i) SEQUENCE CHARACTERISTICS:
              (A) LENGTH: 29 base pairs
              (B) TYPE: nucleic acid
              (C) STRANDEDNESS: single
              (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:13:

CCCGTCGACG AGAGCCAAGG GAATGGTAC                                          29

(2) INFORMATION FOR SEQ ID NO:14:

(i) SEQUENCE CHARACTERISTICS:
              (A) LENGTH: 21 base pairs
              (B) TYPE: nucleic acid
              (C) STRANDEDNESS: single
              (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:14:

CCCAGCAGGT ACAGAGATGT G                                                  21

(2) INFORMATION FOR SEQ ID NO:15:

(i) SEQUENCE CHARACTERISTICS:
              (A) LENGTH: 2624 base pairs
              (B) TYPE: nucleic acid
              (C) STRANDEDNESS: double
              (D) TOPOLOGY: linear (ii) MOLECULE TYPE: cDNA to mRNA (iii) HYPOTHETICAL: NO
```

(iv) ANTI-SENSE: NO (ix) FEATURE:
    (A) NAME/KEY: CDS
    (B) LOCATION: 299..2521

(xi) SEQUENCE DESCRIPTION: SEQ ID NO:15:

```
TGACCCCGCT CCTGGCTGTG CCTGGGACCC CAGTTCCCAG GAGCACGGTT GCAGGAGAGT    60

GACCCCGACT GCTACTGATG GTGCTTCTGC TGCTCCTCTA CTAGCAGGAG TGACTCCTAC   120

CCAGAAGTGG ACTTGGAGGA GGGTCCGTTA GACCATCAGA ATGGAAGCCC GACAAGCAAG   180

TCAGCTGACT CAGGAACCAG AGTGAGGGCC ACGCACTCTC CGCCCCAGCC TGCACCATGA   240

ACTTGCCTTC CCCTTCTGCT TGTTGAGAGC CAAGGGAATG GTACATTACT AGAGAGAG    298

ATG GCT TTC TTT TCT CCC TGG AAG TTG TCC TCT CAG AAG CTG GGC TTT    346
Met Ala Phe Phe Ser Pro Trp Lys Leu Ser Ser Gln Lys Leu Gly Phe
 1               5                  10                  15

TTC TTG GTG ACT TTT GGC TTC ATA TGG GGG ATG ATG CTT CTA CAC TTC    394
Phe Leu Val Thr Phe Gly Phe Ile Trp Gly Met Met Leu Leu His Phe
                20                  25                  30

ACC ATC CAG CAG CGA ACT CAG CCT GAG AGC AGC TCC ATG TTG CGG GAG    442
Thr Ile Gln Gln Arg Thr Gln Pro Glu Ser Ser Ser Met Leu Arg Glu
        35                  40                  45

CAA ATC CTT GAC CTC AGC AAA AGG TAC ATT AAG GCA CTG GCA GAA GAG    490
Gln Ile Leu Asp Leu Ser Lys Arg Tyr Ile Lys Ala Leu Ala Glu Glu
     50                  55                  60

AAC AGG AAC GTG GTG GAT GGC CCG TAT GCC GGT GTC ATG ACA GCC TAT    538
Asn Arg Asn Val Val Asp Gly Pro Tyr Ala Gly Val Met Thr Ala Tyr
 65                  70                  75                  80

GAT CTG AAG AAA ACG CTC GCC GTG CTG CTG GAT AAC ATC TTG CAG CGC    586
Asp Leu Lys Lys Thr Leu Ala Val Leu Leu Asp Asn Ile Leu Gln Arg
                85                  90                  95

ATC GGC AAG CTG GAG TCC AAG GTG GAC AAT CTT GTC AAC GGC ACA GGA    634
Ile Gly Lys Leu Glu Ser Lys Val Asp Asn Leu Val Asn Gly Thr Gly
        100                 105                 110

GCG AAT TCT ACC AAC TCC ACC ACG GCT GTC CCC AGC TTG GTG TCA CTG    682
Ala Asn Ser Thr Asn Ser Thr Thr Ala Val Pro Ser Leu Val Ser Leu
     115                 120                 125

GAG AAA ATT AAT GTG GCA GAT ATC ATT AAT GGA GTT CAA GAA AAA TGT    730
Glu Lys Ile Asn Val Ala Asp Ile Ile Asn Gly Val Gln Glu Lys Cys
130                 135                 140

GTA TTG CCT CCT ATG GAT GGC TAC CCC CAC TGC GAG GGG AAA ATC AAG    778
Val Leu Pro Pro Met Asp Gly Tyr Pro His Cys Glu Gly Lys Ile Lys
145                 150                 155                 160

TGG ATG AAA GAC ATG TGG CGG TCA GAC CCC TGC TAC GCA GAC TAT GGA    826
Trp Met Lys Asp Met Trp Arg Ser Asp Pro Cys Tyr Ala Asp Tyr Gly
                165                 170                 175

GTG GAC GGG ACC TCC TGC TCC TTT TTT ATT TAC CTC AGT GAG GTT GAA    874
Val Asp Gly Thr Ser Cys Ser Phe Phe Ile Tyr Leu Ser Glu Val Glu
        180                 185                 190

AAT TGG TGT CCT CGT TTA CCT TGG AGA GCA AAA AAT CCC TAT GAA GAA    922
Asn Trp Cys Pro Arg Leu Pro Trp Arg Ala Lys Asn Pro Tyr Glu Glu
     195                 200                 205

GCT GAC CAT AAC TCA TTG GCA GAA ATC CGC ACG GAT TTT AAC ATT CTC    970
Ala Asp His Asn Ser Leu Ala Glu Ile Arg Thr Asp Phe Asn Ile Leu
210                 215                 220

TAC GGC ATG ATG AAG AAG CAT GAG GAG TTC CGG TGG ATG AGA CTT CGG   1018
Tyr Gly Met Met Lys Lys His Glu Glu Phe Arg Trp Met Arg Leu Arg
225                 230                 235                 240

ATC CGG CGA ATG GCT GAT GCA TGG ATC CAA GCA ATC AAG TCT CTG GCA   1066
```

```
Ile Arg Arg Met Ala Asp Ala Trp Ile Gln Ala Ile Lys Ser Leu Ala
            245                 250                 255

GAG AAA CAA AAC CTA GAG AAG AGG AAA CGG AAG AAA ATC CTT GTT CAC     1114
Glu Lys Gln Asn Leu Glu Lys Arg Lys Arg Lys Lys Ile Leu Val His
            260                 265                 270

CTG GGG CTC CTG ACC AAG GAA TCA GGC TTC AAG ATT GCA GAG ACA GCA     1162
Leu Gly Leu Leu Thr Lys Glu Ser Gly Phe Lys Ile Ala Glu Thr Ala
            275                 280                 285

TTC AGC GGT GGC CCT CTC GGC GAG CTC GTT CAG TGG AGT GAC TTA ATC     1210
Phe Ser Gly Gly Pro Leu Gly Glu Leu Val Gln Trp Ser Asp Leu Ile
    290                 295                 300

ACA TCT CTG TAC CTG CTG GGC CAT GAC ATC CGC ATC TCA GCC TCG CTG     1258
Thr Ser Leu Tyr Leu Leu Gly His Asp Ile Arg Ile Ser Ala Ser Leu
305             310                 315                 320

GCT GAG CTC AAG GAG ATT ATG AAG AAG GTT GTT GGA AAC CGG TCT GGC     1306
Ala Glu Leu Lys Glu Ile Met Lys Lys Val Val Gly Asn Arg Ser Gly
                325                 330                 335

TGT CCA ACT GTA GGA GAC AGA ATC GTT GAG CTT ATT TAT ATC GAT ATT     1354
Cys Pro Thr Val Gly Asp Arg Ile Val Glu Leu Ile Tyr Ile Asp Ile
                340                 345                 350

GTG GGA CTT GCT CAA TTC AAG AAA ACG CTA GGA CCA TCC TGG GTT CAT     1402
Val Gly Leu Ala Gln Phe Lys Lys Thr Leu Gly Pro Ser Trp Val His
            355                 360                 365

TAC CAG TGC ATG CTC CGG GTG CTG GAC TCC TTT GGA ACA GAA CCT GAG     1450
Tyr Gln Cys Met Leu Arg Val Leu Asp Ser Phe Gly Thr Glu Pro Glu
            370                 375                 380

TTC AAT CAC GCA AGT TAC GCC CAG TCG AAA GGC CAC AAG ACC CCC TGG     1498
Phe Asn His Ala Ser Tyr Ala Gln Ser Lys Gly His Lys Thr Pro Trp
385             390                 395                 400

GGA AAG TGG AAT CTG AAC CCG CAA CAG TTT TAC ACC ATG TTC CCT CAT     1546
Gly Lys Trp Asn Leu Asn Pro Gln Gln Phe Tyr Thr Met Phe Pro His
                405                 410                 415

ACC CCA GAC AAC AGC TTT CTG GGC TTC GTG GTC GAG CAG CAC CTG AAC     1594
Thr Pro Asp Asn Ser Phe Leu Gly Phe Val Val Glu Gln His Leu Asn
                420                 425                 430

TCC AGC GAC ATC CAC CAC ATT AAC GAG ATC AAA AGG CAG AAC CAG TCC     1642
Ser Ser Asp Ile His His Ile Asn Glu Ile Lys Arg Gln Asn Gln Ser
            435                 440                 445

CTT GTG TAT GGC AAA GTG GAT AGT TTC TGG AAG AAT AAG AAG ATC TAC     1690
Leu Val Tyr Gly Lys Val Asp Ser Phe Trp Lys Asn Lys Lys Ile Tyr
450                 455                 460

TTG GAC ATC ATT CAC ACG TAC ATG GAA GTG CAC GCC ACT GTT TAC GGC     1738
Leu Asp Ile Ile His Thr Tyr Met Glu Val His Ala Thr Val Tyr Gly
465                 470                 475                 480

TCC AGT ACC AAG AAC ATC CCC AGT TAC GTG AAA AAC CAT GGC ATT CTC     1786
Ser Ser Thr Lys Asn Ile Pro Ser Tyr Val Lys Asn His Gly Ile Leu
                485                 490                 495

AGC GGC CGT GAC CTA CAG TTT CTT CTC CGG GAA ACC AAG CTT TTT GTT     1834
Ser Gly Arg Asp Leu Gln Phe Leu Leu Arg Glu Thr Lys Leu Phe Val
            500                 505                 510

GGG CTT GGA TTC CCT TAT GAA GGT CCA GCT CCC CTG GAA GCC ATC GCG     1882
Gly Leu Gly Phe Pro Tyr Glu Gly Pro Ala Pro Leu Glu Ala Ile Ala
            515                 520                 525

AAT GGA TGT GCT TTC CTG AAC CCC AAG TTC AAC CCT CCT AAA AGC AGC     1930
Asn Gly Cys Ala Phe Leu Asn Pro Lys Phe Asn Pro Pro Lys Ser Ser
530                 535                 540

AAA AAC ACA GAC TTC TTC ATT GGC AAG CCA ACA CTG AGA GAG CTC ACA     1978
Lys Asn Thr Asp Phe Phe Ile Gly Lys Pro Thr Leu Arg Glu Leu Thr
545                 550                 555                 560

TCC CAG CAC CCG TAC GCA GAA GTC TTC ATC GGC CGG CCA CAC GTC TGG     2026
```

```
Ser Gln His Pro Tyr Ala Glu Val Phe Ile Gly Arg Pro His Val Trp
            565                 570                 575

ACC GTG GAC CTC AAT AAC CGA GAG GAA GTA GAA GAC GCA GTA AAA GCC        2074
Thr Val Asp Leu Asn Asn Arg Glu Glu Val Glu Asp Ala Val Lys Ala
            580                 585                 590

ATC TTA AAC CAG AAG ATT GAG CCG TAT ATG CCA TAT GAG TTC ACA TGT        2122
Ile Leu Asn Gln Lys Ile Glu Pro Tyr Met Pro Tyr Glu Phe Thr Cys
            595                 600                 605

GAA GGC ATG CTG CAG AGA ATC AAC GCT TTC ATC GAG AAA CAG GAC TTC        2170
Glu Gly Met Leu Gln Arg Ile Asn Ala Phe Ile Glu Lys Gln Asp Phe
        610                 615                 620

TGC CAC GGC CAA GTG ATG TGG CCG CCC CTT AGC GCC CTG CAG GTG AAG        2218
Cys His Gly Gln Val Met Trp Pro Pro Leu Ser Ala Leu Gln Val Lys
625                 630                 635                 640

CTG GCT GAG CCC GGG CAG TCC TGC AAA CAG GTG TGC CAG GAG AGC CAG        2266
Leu Ala Glu Pro Gly Gln Ser Cys Lys Gln Val Cys Gln Glu Ser Gln
                645                 650                 655

CTC ATC TGC GAG CCG TCC TTC TTC CAG CAC CTC AAC AAG GAA AAG GAC        2314
Leu Ile Cys Glu Pro Ser Phe Phe Gln His Leu Asn Lys Glu Lys Asp
            660                 665                 670

CTG CTG AAG TAT AAG GTA ATC TGC CAA AGC TCA GAA CTA TAC AAG GAC        2362
Leu Leu Lys Tyr Lys Val Ile Cys Gln Ser Ser Glu Leu Tyr Lys Asp
            675                 680                 685

ATC CTG GTG CCC TCC TTC TAC CCC AAG AGC AAG CAC TGT GTG TTC CAA        2410
Ile Leu Val Pro Ser Phe Tyr Pro Lys Ser Lys His Cys Val Phe Gln
            690                 695                 700

GGG GAT CTC CTG CTC TTC AGT TGT GCC GGG GCC CAC CCC ACA CAC CAG        2458
Gly Asp Leu Leu Leu Phe Ser Cys Ala Gly Ala His Pro Thr His Gln
705                 710                 715                 720

CGG ATC TGC CCC TGC CGG GAC TTC ATC AAG GGC CAA GTG GCC CTC TGC        2506
Arg Ile Cys Pro Cys Arg Asp Phe Ile Lys Gly Gln Val Ala Leu Cys
                725                 730                 735

AAA GAC TGC CTA TAG CATAGCCACC CTGGATTCAT TCAGATGGGA AAGACGTGGC        2561
Lys Asp Cys Leu  *
            740

TCCGCTGGGC AGGGCCGAGG GGCTGAAAGA CAGTCAGGGA CTCTGACCAG AGCCTGAAAT     2621

CTT                                                                    2624

(2) INFORMATION FOR SEQ ID NO:16:

(i) SEQUENCE CHARACTERISTICS:
        (A) LENGTH:  740 amino acids
        (B) TYPE: amino acid
        (D) TOPOLOGY: linear (ii) MOLECULE TYPE: protein (xi) SEQUENCE DESCRIPTION: SEQ ID NO:16:

Met Ala Phe Phe Ser Pro Trp Lys Leu Ser Ser Gln Lys Leu Gly Phe
 1               5                  10                  15

Phe Leu Val Thr Phe Gly Phe Ile Trp Gly Met Met Leu Leu His Phe
                20                  25                  30

Thr Ile Gln Gln Arg Thr Gln Pro Glu Ser Ser Ser Met Leu Arg Glu
            35                  40                  45

Gln Ile Leu Asp Leu Ser Lys Arg Tyr Ile Lys Ala Leu Ala Glu Glu
        50                  55                  60

Asn Arg Asn Val Val Asp Gly Pro Tyr Ala Gly Val Met Thr Ala Tyr
65                  70                  75                  80

Asp Leu Lys Lys Thr Leu Ala Val Leu Leu Asp Asn Ile Leu Gln Arg
                85                  90                  95
```

-continued

```
Ile Gly Lys Leu Glu Ser Lys Val Asp Asn Leu Val Asn Gly Thr Gly
            100                 105                 110
Ala Asn Ser Thr Asn Ser Thr Thr Ala Val Pro Ser Leu Val Ser Leu
        115                 120                 125
Glu Lys Ile Asn Val Ala Asp Ile Ile Asn Gly Val Gln Glu Lys Cys
    130                 135                 140
Val Leu Pro Pro Met Asp Gly Tyr Pro His Cys Glu Gly Lys Ile Lys
145                 150                 155                 160
Trp Met Lys Asp Met Trp Arg Ser Asp Pro Cys Tyr Ala Asp Tyr Gly
                165                 170                 175
Val Asp Gly Thr Ser Cys Ser Phe Phe Ile Tyr Leu Ser Glu Val Glu
            180                 185                 190
Asn Trp Cys Pro Arg Leu Pro Trp Arg Ala Lys Asn Pro Tyr Glu Glu
        195                 200                 205
Ala Asp His Asn Ser Leu Ala Glu Ile Arg Thr Asp Phe Asn Ile Leu
    210                 215                 220
Tyr Gly Met Met Lys Lys His Glu Glu Phe Arg Trp Met Arg Leu Arg
225                 230                 235                 240
Ile Arg Arg Met Ala Asp Ala Trp Ile Gln Ala Ile Lys Ser Leu Ala
                245                 250                 255
Glu Lys Gln Asn Leu Glu Lys Arg Lys Arg Lys Lys Ile Leu Val His
            260                 265                 270
Leu Gly Leu Leu Thr Lys Glu Ser Gly Phe Lys Ile Ala Glu Thr Ala
        275                 280                 285
Phe Ser Gly Gly Pro Leu Gly Glu Leu Val Gln Trp Ser Asp Leu Ile
    290                 295                 300
Thr Ser Leu Tyr Leu Leu Gly His Asp Ile Arg Ile Ser Ala Ser Leu
305                 310                 315                 320
Ala Glu Leu Lys Glu Ile Met Lys Lys Val Val Gly Asn Arg Ser Gly
                325                 330                 335
Cys Pro Thr Val Gly Asp Arg Ile Val Glu Leu Ile Tyr Ile Asp Ile
            340                 345                 350
Val Gly Leu Ala Gln Phe Lys Lys Thr Leu Gly Pro Ser Trp Val His
        355                 360                 365
Tyr Gln Cys Met Leu Arg Val Leu Asp Ser Phe Gly Thr Glu Pro Glu
    370                 375                 380
Phe Asn His Ala Ser Tyr Ala Gln Ser Lys Gly His Lys Thr Pro Trp
385                 390                 395                 400
Gly Lys Trp Asn Leu Asn Pro Gln Gln Phe Tyr Thr Met Phe Pro His
                405                 410                 415
Thr Pro Asp Asn Ser Phe Leu Gly Phe Val Glu Gln His Leu Asn
            420                 425                 430
Ser Ser Asp Ile His His Ile Asn Glu Ile Lys Arg Gln Asn Gln Ser
        435                 440                 445
Leu Val Tyr Gly Lys Val Asp Ser Phe Trp Lys Asn Lys Ile Tyr
    450                 455                 460
Leu Asp Ile Ile His Thr Tyr Met Glu Val His Ala Thr Val Tyr Gly
465                 470                 475                 480
Ser Ser Thr Lys Asn Ile Pro Ser Tyr Val Lys Asn His Gly Ile Leu
                485                 490                 495
Ser Gly Arg Asp Leu Gln Phe Leu Leu Arg Glu Thr Lys Leu Phe Val
            500                 505                 510
Gly Leu Gly Phe Pro Tyr Glu Gly Pro Ala Pro Leu Glu Ala Ile Ala
```

```
                515                 520                 525
Asn Gly Cys Ala Phe Leu Asn Pro Lys Phe Asn Pro Lys Ser Ser
    530                 535                 540

Lys Asn Thr Asp Phe Phe Ile Gly Lys Pro Thr Leu Arg Glu Leu Thr
545                 550                 555                 560

Ser Gln His Pro Tyr Ala Glu Val Phe Ile Gly Arg Pro His Val Trp
                565                 570                 575

Thr Val Asp Leu Asn Asn Arg Glu Glu Val Glu Asp Ala Val Lys Ala
            580                 585                 590

Ile Leu Asn Gln Lys Ile Glu Pro Tyr Met Pro Tyr Glu Phe Thr Cys
        595                 600                 605

Glu Gly Met Leu Gln Arg Ile Asn Ala Phe Ile Glu Lys Gln Asp Phe
    610                 615                 620

Cys His Gly Gln Val Met Trp Pro Pro Leu Ser Ala Leu Gln Val Lys
625                 630                 635                 640

Leu Ala Glu Pro Gly Gln Ser Cys Lys Gln Val Cys Gln Glu Ser Gln
                645                 650                 655

Leu Ile Cys Glu Pro Ser Phe Phe Gln His Leu Asn Lys Glu Lys Asp
            660                 665                 670

Leu Leu Lys Tyr Lys Val Ile Cys Gln Ser Ser Glu Leu Tyr Lys Asp
        675                 680                 685

Ile Leu Val Pro Ser Phe Tyr Pro Lys Ser Lys His Cys Val Phe Gln
    690                 695                 700

Gly Asp Leu Leu Phe Ser Cys Ala Gly Ala His Pro Thr His Gln
705                 710                 715                 720

Arg Ile Cys Pro Cys Arg Asp Phe Ile Lys Gly Gln Val Ala Leu Cys
                725                 730                 735

Lys Asp Cys Leu
            740

(2) INFORMATION FOR SEQ ID NO:17:

(i) SEQUENCE CHARACTERISTICS:
        (A) LENGTH: 2367 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 145..2367

(xi) SEQUENCE DESCRIPTION: SEQ ID NO:17:

AGCAGAATGG AAGCCAGGCA AGGAAATCAG CTGACTCAGG AGCCGGAGTG AGAGCGACAC      60

ACCCTCCGCC CCAGCCTGCA CCATGAACTT GCCTTCACCT TCTGCACGTT GAGAGCCAAG     120

GGAGGGGTAC ATTGCCAGAG AGAG ATG GCT TTC TTT ACT CCC TGG AAG TTG       171
                              Met Ala Phe Phe Thr Pro Trp Lys Leu
                                  745                 750

TCC TCT CAG AAG CTA GGC TTT TTC TTG GTG ACT TTT GGC TTT ATA TGG      219
Ser Ser Gln Lys Leu Gly Phe Phe Leu Val Thr Phe Gly Phe Ile Trp
            755                 760                 765

GGG ATG ATG CTT CTG CAC TTC ACC ATC CAG CAG CGG ACT CAG CCT GAG      267
Gly Met Met Leu Leu His Phe Thr Ile Gln Gln Arg Thr Gln Pro Glu
    770                 775                 780

AGC AGC TCC ATG TTG CGG GAG CAA ATC CTG GAT CTC AGC AAA AGG TAC      315
Ser Ser Ser Met Leu Arg Glu Gln Ile Leu Asp Leu Ser Lys Arg Tyr
785                 790                 795
```

```
ATC AAA GCA CTG GCA GAA GAA AAC AGA AAC GTG GTG GAT GGA CCA TAC       363
Ile Lys Ala Leu Ala Glu Glu Asn Arg Asn Val Val Asp Gly Pro Tyr
    800                 805                 810

GCT GGC GTC ATG ACA GCT TAT GAT CTG AAG AAA ACA CTT GCT GTA CTA       411
Ala Gly Val Met Thr Ala Tyr Asp Leu Lys Lys Thr Leu Ala Val Leu
815                 820                 825                 830

CTA GAT AAC ATC TTG CAA CGC ATT GGC AAG CTC GAG TCG AAG GTG GAC       459
Leu Asp Asn Ile Leu Gln Arg Ile Gly Lys Leu Glu Ser Lys Val Asp
                835                 840                 845

AAT CTC GTC AAT GGC ACA GGA GCA AAT TCT ACC AAC TCC ACC ACA GCT       507
Asn Leu Val Asn Gly Thr Gly Ala Asn Ser Thr Asn Ser Thr Thr Ala
    850                 855                 860

GTC CCC AGC TTG GTA TCG CTT GAA AAA ATT AGT GTG GCA GAT ATC ATT       555
Val Pro Ser Leu Val Ser Leu Glu Lys Ile Ser Val Ala Asp Ile Ile
865                 870                 875

AAT GGA GTT CAA GAA AAA TGT GTA TTG CCT CCT ATG GAT GGC TAC CCC       603
Asn Gly Val Gln Glu Lys Cys Val Leu Pro Pro Met Asp Gly Tyr Pro
                880                 885                 890

CAC TGC GAG GGG AAA ATC AAG TGG ATG AAA GAC ATG TGG CGC TCG GAT       651
His Cys Glu Gly Lys Ile Lys Trp Met Lys Asp Met Trp Arg Ser Asp
895                 900                 905                 910

CCC TGC TAC GCA GAC TAT GGA GTG GAC GGC ACC TCC TGC TCC TTT TTT       699
Pro Cys Tyr Ala Asp Tyr Gly Val Asp Gly Thr Ser Cys Ser Phe Phe
                915                 920                 925

ATT TAC CTC AGT GAG GTT GAA AAT TGG TGT CCT CGT TTA CCT TGG AGA       747
Ile Tyr Leu Ser Glu Val Glu Asn Trp Cys Pro Arg Leu Pro Trp Arg
        930                 935                 940

GCA AAA AAT CCC TAT GAA GAA GCT GAT CAT AAC TCA TTG GCG GAA ATC       795
Ala Lys Asn Pro Tyr Glu Glu Ala Asp His Asn Ser Leu Ala Glu Ile
    945                 950                 955

CGT ACG GAT TTT AAC ATT CTC TAC AGC ATG ATG AAG AAG CAT GAG GAG       843
Arg Thr Asp Phe Asn Ile Leu Tyr Ser Met Met Lys Lys His Glu Glu
960                 965                 970

TTC CGG TGG ATG AGA CTT CGG ATC CGG CGA ATG GCT GAT GCG TGG ATC       891
Phe Arg Trp Met Arg Leu Arg Ile Arg Arg Met Ala Asp Ala Trp Ile
975                 980                 985                 990

CAA GCA ATC AAG TCT CTG GCA GAG AAA CAA AAC CTG GAA AAG AGA AAA       939
Gln Ala Ile Lys Ser Leu Ala Glu Lys Gln Asn Leu Glu Lys Arg Lys
        995                 1000                1005

CGG AAG AAA ATC CTT GTT CAC CTG GGG CTC CTG ACC AAG GAA TCT GGC       987
Arg Lys Lys Ile Leu Val His Leu Gly Leu Leu Thr Lys Glu Ser Gly
    1010                1015                1020

TTC AAG ATT GCA GAG ACG GCA TTC AGT GGT GGC CCT CTT GGC GAA CTG      1035
Phe Lys Ile Ala Glu Thr Ala Phe Ser Gly Gly Pro Leu Gly Glu Leu
        1025                1030                1035

GTT CAG TGG AGT GAC TTA ATT ACA TCT CTC TAC CTA CTG GGC CAT GAC      1083
Val Gln Trp Ser Asp Leu Ile Thr Ser Leu Tyr Leu Leu Gly His Asp
    1040                1045                1050

ATC CGG ATC TCG GCT TCA CTG GCT GAG CTA AAG GAG ATT ATG AAG AAG      1131
Ile Arg Ile Ser Ala Ser Leu Ala Glu Leu Lys Glu Ile Met Lys Lys
1055                1060                1065                1070

GTT GTT GGA AAT CGG TCT GGC TGT CCC ACT GTA GGA GAC AGA ATC GTT      1179
Val Val Gly Asn Arg Ser Gly Cys Pro Thr Val Gly Asp Arg Ile Val
        1075                1080                1085

GAG CTT ATT TAT ATT GAT ATT GTG GGA CTT GCT CAA TTT AAG AAA ACT      1227
Glu Leu Ile Tyr Ile Asp Ile Val Gly Leu Ala Gln Phe Lys Lys Thr
    1090                1095                1100

CTA GGA CCA TCC TGG GTT CAC TAC CAG TGC ATG CTC CGA GTG CTA GAT      1275
Leu Gly Pro Ser Trp Val His Tyr Gln Cys Met Leu Arg Val Leu Asp
        1105                1110                1115
```

```
TCC TTT GGA ACA GAA CCT GAG TTC AAT CAT GCA AGT TAT GCC CAG TCG    1323
Ser Phe Gly Thr Glu Pro Glu Phe Asn His Ala Ser Tyr Ala Gln Ser
1120                    1125                1130

AAA GGC CAC AAG ACC CCC TGG GGA AAA TGG AAT CTG AAC CCG CAG CAG    1371
Lys Gly His Lys Thr Pro Trp Gly Lys Trp Asn Leu Asn Pro Gln Gln
1135                1140                1145                1150

TTT TAC ACC ATG TTC CCT CAC ACC CCA GAT AAC AGC TTC CTG GGC TTC    1419
Phe Tyr Thr Met Phe Pro His Thr Pro Asp Asn Ser Phe Leu Gly Phe
                1155                1160                1165

GTG GTC GAG CAG CAC CTG AAC TCT AGC GAC ATC CAC CAC ATT AAT GAG    1467
Val Val Glu Gln His Leu Asn Ser Ser Asp Ile His His Ile Asn Glu
1170                1175                1180

ATC AAA AGG CAG AAC CAG TCC CTT GTG TAT GGC AAA GTG GAT AGT TTC    1515
Ile Lys Arg Gln Asn Gln Ser Leu Val Tyr Gly Lys Val Asp Ser Phe
            1185                1190                1195

TGG AAG AAT AAG AAA ATC TAC TTG GAT ATC ATT CAC ACG TAC ATG GAA    1563
Trp Lys Asn Lys Lys Ile Tyr Leu Asp Ile Ile His Thr Tyr Met Glu
1200                1205                1210

GTT CAT GCC ACT GTT TAC GGC TCC AGC ACA AAG AAC ATT CCC AGT TAC    1611
Val His Ala Thr Val Tyr Gly Ser Ser Thr Lys Asn Ile Pro Ser Tyr
1215                1220                1225                1230

GTG AAA AAT CAT GGC ATT CTC AGT GGG CGT GAC CTG CAG TTT CTT CTC    1659
Val Lys Asn His Gly Ile Leu Ser Gly Arg Asp Leu Gln Phe Leu Leu
                1235                1240                1245

CGG GAA ACA AAG CTG TTT GTT GGG CTG GGA TTC CCT TAT GAG GGT CCA    1707
Arg Glu Thr Lys Leu Phe Val Gly Leu Gly Phe Pro Tyr Glu Gly Pro
            1250                1255                1260

GCT CCC CTA GAG GCC ATT GCA AAT GGA TGT GCT TTC CTG AAC CCC AAG    1755
Ala Pro Leu Glu Ala Ile Ala Asn Gly Cys Ala Phe Leu Asn Pro Lys
1265                1270                1275

TTC AGC CCT CCC AAG AGC AGC AAA AAT ACA GAC TTC TTC ATT GGC AAG    1803
Phe Ser Pro Pro Lys Ser Ser Lys Asn Thr Asp Phe Phe Ile Gly Lys
1280                1285                1290

CCG ACC CTG AGA GAG CTG ACG TCT CAG CAC CCT TAT GCA GAA GTC TTC    1851
Pro Thr Leu Arg Glu Leu Thr Ser Gln His Pro Tyr Ala Glu Val Phe
1295                1300                1305                1310

ATC GGC CGG CCA CAC GTC TGG ACC GTG GAT CTG AAC AAT CGA GAG GAA    1899
Ile Gly Arg Pro His Val Trp Thr Val Asp Leu Asn Asn Arg Glu Glu
                1315                1320                1325

GTA GAG GAT GCC GTG AAA GCC ATC TTA AAC CAG AAG ATT GAG CCG TAT    1947
Val Glu Asp Ala Val Lys Ala Ile Leu Asn Gln Lys Ile Glu Pro Tyr
            1330                1335                1340

ATG CCG TAT GAG TTC ACA TGT GAA GGG ATG CTG CAG AGA ATC AAC GCG    1995
Met Pro Tyr Glu Phe Thr Cys Glu Gly Met Leu Gln Arg Ile Asn Ala
1345                1350                1355

TTC ATA GAG AAG CAG GAC TTC TGC CAT GGC CAG GTG ATG TGG CCT CCC    2043
Phe Ile Glu Lys Gln Asp Phe Cys His Gly Gln Val Met Trp Pro Pro
1360                1365                1370

CTG AGC GCC TTG CAG GTG AAG CTG GCT GAG CCT GGG CAG TCC TGC AAG    2091
Leu Ser Ala Leu Gln Val Lys Leu Ala Glu Pro Gly Gln Ser Cys Lys
1375                1380                1385                1390

CAA GTG TGC CAG GAG AAC CAG CTC ATC TGT GAG CCA TCC TTC TTC CAG    2139
Gln Val Cys Gln Glu Asn Gln Leu Ile Cys Glu Pro Ser Phe Phe Gln
            1395                1400                1405

CAC CTC AAC AAG GAA AAG GAC TTG CTG AAG TAC AGA GTG ACC TGC CAA    2187
His Leu Asn Lys Glu Lys Asp Leu Leu Lys Tyr Arg Val Thr Cys Gln
1410                1415                1420

AGC TCA GAA CTG TAC AAG GAC ATC CTG GTG CCA TCC TTC TAC CCC AAG    2235
Ser Ser Glu Leu Tyr Lys Asp Ile Leu Val Pro Ser Phe Tyr Pro Lys
1425                1430                1435
```

```
AGC AAG CAC TGT GTG CTC CAA GGG GAT CTC CTG CTC TTC AGT TGT GCC    2283
Ser Lys His Cys Val Leu Gln Gly Asp Leu Leu Leu Phe Ser Cys Ala
    1440                1445                1450

GGG GCC CAC CCC ACA CAC CAG AGG ATC TGC CCC TGC CGG GAC TTC ATC    2331
Gly Ala His Pro Thr His Gln Arg Ile Cys Pro Cys Arg Asp Phe Ile
1455                1460                1465                1470

AAG GGC CAA GTG GCC CTA TGC AAA GAC TGC CTA TAG                    2367
Lys Gly Gln Val Ala Leu Cys Lys Asp Cys Leu  *
                1475                1480
```

(2) INFORMATION FOR SEQ ID NO:18:

(i) SEQUENCE CHARACTERISTICS:
        (A) LENGTH: 740 amino acids
        (B) TYPE: amino acid
        (D) TOPOLOGY: linear (ii) MOLECULE TYPE: protein (xi) SEQUENCE DESCRIPTION: SEQ ID NO:18:

```
Met Ala Phe Phe Thr Pro Trp Lys Leu Ser Ser Gln Lys Leu Gly Phe
 1               5                  10                  15

Phe Leu Val Thr Phe Gly Phe Ile Trp Gly Met Met Leu Leu His Phe
             20                  25                  30

Thr Ile Gln Gln Arg Thr Gln Pro Glu Ser Ser Ser Met Leu Arg Glu
         35                  40                  45

Gln Ile Leu Asp Leu Ser Lys Arg Tyr Ile Lys Ala Leu Ala Glu Glu
 50                  55                  60

Asn Arg Asn Val Val Asp Gly Pro Tyr Ala Gly Val Met Thr Ala Tyr
 65                  70                  75                  80

Asp Leu Lys Lys Thr Leu Ala Val Leu Leu Asp Asn Ile Leu Gln Arg
                 85                  90                  95

Ile Gly Lys Leu Glu Ser Lys Val Asp Asn Leu Val Asn Gly Thr Gly
                100                 105                 110

Ala Asn Ser Thr Asn Ser Thr Thr Ala Val Pro Ser Leu Val Ser Leu
            115                 120                 125

Glu Lys Ile Ser Val Ala Asp Ile Ile Asn Gly Val Gln Glu Lys Cys
130                 135                 140

Val Leu Pro Pro Met Asp Gly Tyr Pro His Cys Glu Gly Lys Ile Lys
145                 150                 155                 160

Trp Met Lys Asp Met Trp Arg Ser Asp Pro Cys Tyr Ala Asp Tyr Gly
                165                 170                 175

Val Asp Gly Thr Ser Cys Ser Phe Phe Ile Tyr Leu Ser Glu Val Glu
                180                 185                 190

Asn Trp Cys Pro Arg Leu Pro Trp Arg Ala Lys Asn Pro Tyr Glu Glu
            195                 200                 205

Ala Asp His Asn Ser Leu Ala Glu Ile Arg Thr Asp Phe Asn Ile Leu
            210                 215                 220

Tyr Ser Met Met Lys Lys His Glu Glu Phe Arg Trp Met Arg Leu Arg
225                 230                 235                 240

Ile Arg Arg Met Ala Asp Ala Trp Ile Gln Ala Ile Lys Ser Leu Ala
                245                 250                 255

Glu Lys Gln Asn Leu Glu Lys Arg Lys Arg Lys Lys Ile Leu Val His
            260                 265                 270

Leu Gly Leu Leu Thr Lys Glu Ser Gly Phe Lys Ile Ala Glu Thr Ala
            275                 280                 285

Phe Ser Gly Gly Pro Leu Gly Glu Leu Val Gln Trp Ser Asp Leu Ile
```

```
            290                 295                 300
Thr Ser Leu Tyr Leu Leu Gly His Asp Ile Arg Ile Ser Ala Ser Leu
305                 310                 315                 320

Ala Glu Leu Lys Glu Ile Met Lys Lys Val Val Gly Asn Arg Ser Gly
                325                 330                 335

Cys Pro Thr Val Gly Asp Arg Ile Val Glu Leu Ile Tyr Ile Asp Ile
                340                 345                 350

Val Gly Leu Ala Gln Phe Lys Lys Thr Leu Gly Pro Ser Trp Val His
                355                 360                 365

Tyr Gln Cys Met Leu Arg Val Leu Asp Ser Phe Gly Thr Glu Pro Glu
                370                 375                 380

Phe Asn His Ala Ser Tyr Ala Gln Ser Lys Gly His Lys Thr Pro Trp
385                 390                 395                 400

Gly Lys Trp Asn Leu Asn Pro Gln Gln Phe Tyr Thr Met Phe Pro His
                405                 410                 415

Thr Pro Asp Asn Ser Phe Leu Gly Phe Val Val Glu Gln His Leu Asn
                420                 425                 430

Ser Ser Asp Ile His His Ile Asn Glu Ile Lys Arg Gln Asn Gln Ser
                435                 440                 445

Leu Val Tyr Gly Lys Val Asp Ser Phe Trp Lys Asn Lys Lys Ile Tyr
450                 455                 460

Leu Asp Ile Ile His Thr Tyr Met Glu Val His Ala Thr Val Tyr Gly
465                 470                 475                 480

Ser Ser Thr Lys Asn Ile Pro Ser Tyr Val Lys Asn His Gly Ile Leu
                485                 490                 495

Ser Gly Arg Asp Leu Gln Phe Leu Leu Arg Glu Thr Lys Leu Phe Val
                500                 505                 510

Gly Leu Gly Phe Pro Tyr Glu Gly Pro Ala Pro Leu Glu Ala Ile Ala
                515                 520                 525

Asn Gly Cys Ala Phe Leu Asn Pro Lys Phe Ser Pro Pro Lys Ser Ser
                530                 535                 540

Lys Asn Thr Asp Phe Phe Ile Gly Lys Pro Thr Leu Arg Glu Leu Thr
545                 550                 555                 560

Ser Gln His Pro Tyr Ala Glu Val Phe Ile Gly Arg Pro His Val Trp
                565                 570                 575

Thr Val Asp Leu Asn Asn Arg Glu Glu Val Glu Asp Ala Val Lys Ala
                580                 585                 590

Ile Leu Asn Gln Lys Ile Glu Pro Tyr Met Pro Tyr Glu Phe Thr Cys
                595                 600                 605

Glu Gly Met Leu Gln Arg Ile Asn Ala Phe Ile Glu Lys Gln Asp Phe
                610                 615                 620

Cys His Gly Gln Val Met Trp Pro Pro Leu Ser Ala Leu Gln Val Lys
625                 630                 635                 640

Leu Ala Glu Pro Gly Gln Ser Cys Lys Gln Val Cys Gln Glu Asn Gln
                645                 650                 655

Leu Ile Cys Glu Pro Ser Phe Phe Gln His Leu Asn Lys Glu Lys Asp
                660                 665                 670

Leu Leu Lys Tyr Arg Val Thr Cys Gln Ser Ser Glu Leu Tyr Lys Asp
                675                 680                 685

Ile Leu Val Pro Ser Phe Tyr Pro Lys Ser Lys His Cys Val Leu Gln
                690                 695                 700

Gly Asp Leu Leu Leu Phe Ser Cys Ala Gly Ala His Pro Thr His Gln
705                 710                 715                 720
```

```
                Arg Ile Cys Pro Cys Arg Asp Phe Ile Lys Gly Gln Val Ala Leu Cys
                                725                 730                 735

Lys Asp Cys Leu
                        740

(2) INFORMATION FOR SEQ ID NO:19:

(i) SEQUENCE CHARACTERISTICS:
        (A) LENGTH: 2564 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 38..2263

(xi) SEQUENCE DESCRIPTION: SEQ ID NO:19:

GTTAAGAGCC AAGGACAGGT GAAGTTGCCA GAGAGCA ATG GCT CTC TTC ACT CCG        55
                                        Met Ala Leu Phe Thr Pro
                                                            745

TGG AAG TTG TCC TCT CAG AAG CTG GGC TTT TTC CTG GTG ACT TTT GGC        103
Trp Lys Leu Ser Ser Gln Lys Leu Gly Phe Phe Leu Val Thr Phe Gly
        750                 755                 760

TTC ATT TGG GGT ATG ATG CTT CTG CAC TTT ACC ATC CAG CAG CGA ACT        151
Phe Ile Trp Gly Met Met Leu Leu His Phe Thr Ile Gln Gln Arg Thr
765                 770                 775

CAG CCT GAA AGC AGC TCC ATG CTG CGC GAG CAG ATC CTG GAC CTC AGC        199
Gln Pro Glu Ser Ser Ser Met Leu Arg Glu Gln Ile Leu Asp Leu Ser
780                 785                 790                 795

AAA AGG TAC ATC AAG GCA CTG GCA GAA GAA AAC AGG AAT GTG GTG GAT        247
Lys Arg Tyr Ile Lys Ala Leu Ala Glu Glu Asn Arg Asn Val Val Asp
                800                 805                 810

GGG CCA TAC GCT GGA GTC ATG ACA GCT TAT GAT CTG AAG AAA ACC CTT        295
Gly Pro Tyr Ala Gly Val Met Thr Ala Tyr Asp Leu Lys Lys Thr Leu
            815                 820                 825

GCT GTG TTA TTA GAT AAC ATT TTG CAG CGC ATT GGC AAG TTG GAG TCG        343
Ala Val Leu Leu Asp Asn Ile Leu Gln Arg Ile Gly Lys Leu Glu Ser
        830                 835                 840

AAG GTG GAC AAT CTT GTT GTC AAT GGC ACC GGA ACA AAC TCA ACC AAC        391
Lys Val Asp Asn Leu Val Val Asn Gly Thr Gly Thr Asn Ser Thr Asn
845                 850                 855

TCC ACT ACA GCT GTT CCC AGC TTG GTT GCA CTT GAG AAA ATT AAT GTG        439
Ser Thr Thr Ala Val Pro Ser Leu Val Ala Leu Glu Lys Ile Asn Val
860                 865                 870                 875

GCA GAT ATC ATT AAC GGA GCT CAA GAA AAA TGT GTA TTG CCT CCT ATG        487
Ala Asp Ile Ile Asn Gly Ala Gln Glu Lys Cys Val Leu Pro Pro Met
                880                 885                 890

GAC GGC TAC CCT CAC TGT GAG GGA AAG ATC AAG TGG ATG AAA GAC ATG        535
Asp Gly Tyr Pro His Cys Glu Gly Lys Ile Lys Trp Met Lys Asp Met
            895                 900                 905

TGG CGT TCA GAT CCC TGC TAC GCA GAC TAT GGA GTG GAT GGA TCC ACC        583
Trp Arg Ser Asp Pro Cys Tyr Ala Asp Tyr Gly Val Asp Gly Ser Thr
        910                 915                 920

TGC TCT TTT TTT ATT TAC CTC AGT GAG GTT GAA AAT TGG TGT CCT CAT        631
Cys Ser Phe Phe Ile Tyr Leu Ser Glu Val Glu Asn Trp Cys Pro His
925                 930                 935

TTA CCT TGG AGA GCA AAA AAT CCC TAC GAA GAA GCT GAT CAT AAT TCA        679
Leu Pro Trp Arg Ala Lys Asn Pro Tyr Glu Glu Ala Asp His Asn Ser
940                 945                 950                 955

TTG GCG GAA ATT CGT ACA GAT TTT AAT ATT CTC TAC AGT ATG ATG AAA        727
```

-continued

```
                Leu Ala Glu Ile Arg Thr Asp Phe Asn Ile Leu Tyr Ser Met Met Lys
                                960                 965                 970

AAG CAT GAA GAA TTC CGG TGG ATG AGA CTA CGG ATC CGG CGA ATG GCT                775
Lys His Glu Glu Phe Arg Trp Met Arg Leu Arg Ile Arg Arg Met Ala
            975                 980                 985

GAC GCA TGG ATC CAA GCA ATC AAG TCC CTG GCA GAA AAG CAG AAC CTT                823
Asp Ala Trp Ile Gln Ala Ile Lys Ser Leu Ala Glu Lys Gln Asn Leu
            990                 995                 1000

GAA AAG AGA AAG CGG AAG AAA GTC CTC GTT CAC CTG GGA CTC CTG ACC                871
Glu Lys Arg Lys Arg Lys Lys Val Leu Val His Leu Gly Leu Leu Thr
        1005                1010                1015

AAG GAA TCT GGA TTT AAG ATT GCA GAG ACA GCT TTC AGT GGT GGC CCT                919
Lys Glu Ser Gly Phe Lys Ile Ala Glu Thr Ala Phe Ser Gly Gly Pro
1020                1025                1030                1035

CTT GGT GAA TTA GTT CAA TGG AGT GAT TTA ATT ACA TCT CTG TAC TTA                967
Leu Gly Glu Leu Val Gln Trp Ser Asp Leu Ile Thr Ser Leu Tyr Leu
                1040                1045                1050

CTG GGC CAT GAC ATT AGG ATT TCA GCT TCA CTG GCT GAG CTC AAG GAA                1015
Leu Gly His Asp Ile Arg Ile Ser Ala Ser Leu Ala Glu Leu Lys Glu
                1055                1060                1065

ATC ATG AAG AAG GTT GTA GGA AAC CGA TCT GGC TGC CCA ACT GTA GGA                1063
Ile Met Lys Lys Val Val Gly Asn Arg Ser Gly Cys Pro Thr Val Gly
1070                1075                1080

GAC AGA ATT GTT GAG CTC ATT TAC ATT GAT ATT GTA GGA CTT GCT CAA                1111
Asp Arg Ile Val Glu Leu Ile Tyr Ile Asp Ile Val Gly Leu Ala Gln
        1085                1090                1095

TTC AAG AAA ACT CTT GGA CCA TCC TGG GTT CAT TAC CAG TGC ATG CTC                1159
Phe Lys Lys Thr Leu Gly Pro Ser Trp Val His Tyr Gln Cys Met Leu
1100                1105                1110                1115

CGA GTC CTT GAT TCA TTT GGT ACT GAA CCC GAA TTT AAT CAT GCA AAT                1207
Arg Val Leu Asp Ser Phe Gly Thr Glu Pro Glu Phe Asn His Ala Asn
                1120                1125                1130

TAT GCC CAA TCG AAA GGC CAC AAG ACC CCT TGG GGA AAA TGG AAT CTG                1255
Tyr Ala Gln Ser Lys Gly His Lys Thr Pro Trp Gly Lys Trp Asn Leu
                1135                1140                1145

AAC CCT CAG CAG TTT TAT ACC ATG TTC CCT CAT ACC CCA GAC AAC AGC                1303
Asn Pro Gln Gln Phe Tyr Thr Met Phe Pro His Thr Pro Asp Asn Ser
            1150                1155                1160

TTT CTG GGG TTT GTG GTT GAG CAG CAC CTG AAC TCC AGT GAT ATC CAC                1351
Phe Leu Gly Phe Val Val Glu Gln His Leu Asn Ser Ser Asp Ile His
1165                1170                1175

CAC ATT AAT GAA ATC AAA AGG CAG AAC CAG TCC CTT GTG TAT GGC AAA                1399
His Ile Asn Glu Ile Lys Arg Gln Asn Gln Ser Leu Val Tyr Gly Lys
1180                1185                1190                1195

GTG GAT AGC TTC TGG AAG AAT AAG AAG ATC TAC TTG GAC ATT ATT CAC                1447
Val Asp Ser Phe Trp Lys Asn Lys Lys Ile Tyr Leu Asp Ile Ile His
                1200                1205                1210

ACA TAC ATG GAA GTG CAT GCA ACT GTT TAT GGC TCC AGC ACA AAG AAT                1495
Thr Tyr Met Glu Val His Ala Thr Val Tyr Gly Ser Ser Thr Lys Asn
                1215                1220                1225

ATT CCC AGT TAC GTG AAA AAC CAT GGT ATC CTC AGT GGA CGG GAC CTG                1543
Ile Pro Ser Tyr Val Lys Asn His Gly Ile Leu Ser Gly Arg Asp Leu
            1230                1235                1240

CAG TTC CTT CTT CGA GAA ACC AAG TTG TTT GTT GGA CTT GGG TTC CCT                1591
Gln Phe Leu Leu Arg Glu Thr Lys Leu Phe Val Gly Leu Gly Phe Pro
        1245                1250                1255

TAC GAG GGC CCA GCT CCC CTG GAA GCT ATC GCA AAT GGA TGT GCT TTT                1639
Tyr Glu Gly Pro Ala Pro Leu Glu Ala Ile Ala Asn Gly Cys Ala Phe
1260                1265                1270                1275

CTG AAT CCC AAG TTC AAC CCA CCC AAA AGC AGC AAA AAC ACA GAC TTT                1687
```

-continued

```
Leu Asn Pro Lys Phe Asn Pro Lys Ser Ser Lys Asn Thr Asp Phe
            1280                1285                1290

TTC ATT GGC AAG CCA ACT CTG AGA GAG CTG ACA TCC CAG CAT CCT TAC    1735
Phe Ile Gly Lys Pro Thr Leu Arg Glu Leu Thr Ser Gln His Pro Tyr
                1295                1300                1305

GCT GAA GTT TTC ATC GGG CGG CCA CAT GTG TGG ACT GTT GAC CTC AAC    1783
Ala Glu Val Phe Ile Gly Arg Pro His Val Trp Thr Val Asp Leu Asn
            1310                1315                1320

AAT CAG GAG GAA GTA GAG GAT GCA GTG AAA GCA ATT TTA AAT CAG AAG    1831
Asn Gln Glu Glu Val Glu Asp Ala Val Lys Ala Ile Leu Asn Gln Lys
        1325                1330                1335

ATT GAG CCA TAC ATG CCA TAT GAA TTT ACG TGC GAG GGG ATG CTA CAG    1879
Ile Glu Pro Tyr Met Pro Tyr Glu Phe Thr Cys Glu Gly Met Leu Gln
1340                1345                1350                1355

AGA ATC AAT GCT TTC ATT GAA AAA CAG GAC TTC TGC CAT GGG CAA GTG    1927
Arg Ile Asn Ala Phe Ile Glu Lys Gln Asp Phe Cys His Gly Gln Val
            1360                1365                1370

ATG TGG CCA CCC CTC AGC GCC CTA CAG GTC AAG CTT GCT GAG CCC GGG    1975
Met Trp Pro Pro Leu Ser Ala Leu Gln Val Lys Leu Ala Glu Pro Gly
                1375                1380                1385

CAG TCC TGC AAG CAG GTG TGC CAG GAG AGC CAG CTC ATC TGC GAG CCT    2023
Gln Ser Cys Lys Gln Val Cys Gln Glu Ser Gln Leu Ile Cys Glu Pro
            1390                1395                1400

TCT TTC TTC CAG CAC CTC AAC AAG GAC AAG GAC ATG CTG AAG TAC AAG    2071
Ser Phe Phe Gln His Leu Asn Lys Asp Lys Asp Met Leu Lys Tyr Lys
        1405                1410                1415

GTG ACC TGC CAA AGC TCA GAG CTG GCC AAG GAC ATC CTG GTG CCC TCC    2119
Val Thr Cys Gln Ser Ser Glu Leu Ala Lys Asp Ile Leu Val Pro Ser
1420                1425                1430                1435

TTT GAC CCT AAG AAT AAG CAC TGT GTG TTT CAA GGT GAC CTC CTG CTC    2167
Phe Asp Pro Lys Asn Lys His Cys Val Phe Gln Gly Asp Leu Leu Leu
            1440                1445                1450

TTC AGC TGT GCA GGC GCC CAC CCC AGG CAC CAG AGG GTC TGC CCC TGC    2215
Phe Ser Cys Ala Gly Ala His Pro Arg His Gln Arg Val Cys Pro Cys
                1455                1460                1465

CGG GAC TTC ATC AAG GGC CAG GTG GCT CTC TGC AAA GAC TGC CTA TAG    2263
Arg Asp Phe Ile Lys Gly Gln Val Ala Leu Cys Lys Asp Cys Leu  *
            1470                1475                1480

CAGCTACCTG CTCAGCCCTG CACCATGCTG CTGGGGAAGA CAGTGGCCCC AGCCCCCTCA    2323

GGCAGGGCCA GGGACAGAAG TCATGCAGGG ACTCTGGCAA GAGCCTGAAC TTTTTCGTAG    2383

AAGGTTCTGA ATTGGCATTG CCCTTGCTGC ACTCCGAGCA ACCCAGTGGA GTCTTCACCA    2443

AAACAAAACA AGAGCGTATG TCAGGCCAGG AGCCTGGCCT GTCCCTGGCA CAACATCATT    2503

TCTGTTTCTC AAGGAGCAAC TGTGGGAAGA CTGTCACTGC AGCTGCTCCA GGGCAAAAGA    2563

A                                                                   2564
```

(2) INFORMATION FOR SEQ ID NO:20:

(i) SEQUENCE CHARACTERISTICS:
        (A) LENGTH:   741 amino acids
        (B) TYPE: amino acid
        (D) TOPOLOGY: linear (ii) MOLECULE TYPE: protein (xi) SEQUENCE DESCRIPTION: SEQ ID NO:20:

```
Met Ala Leu Phe Thr Pro Trp Lys Leu Ser Ser Gln Lys Leu Gly Phe
1                5                  10                  15

Phe Leu Val Thr Phe Gly Phe Ile Trp Gly Met Met Leu Leu His Phe
                20                  25                  30
```

```
Thr Ile Gln Gln Arg Thr Gln Pro Glu Ser Ser Ser Met Leu Arg Glu
        35                  40                  45

Gln Ile Leu Asp Leu Ser Lys Arg Tyr Ile Lys Ala Leu Ala Glu Glu
    50                  55                  60

Asn Arg Asn Val Val Asp Gly Pro Tyr Ala Gly Val Met Thr Ala Tyr
65                  70                  75                  80

Asp Leu Lys Lys Thr Leu Ala Val Leu Leu Asp Asn Ile Leu Gln Arg
                85                  90                  95

Ile Gly Lys Leu Glu Ser Lys Val Asp Asn Leu Val Val Asn Gly Thr
                100                 105                 110

Gly Thr Asn Ser Thr Asn Ser Thr Thr Ala Val Pro Ser Leu Val Ala
            115                 120                 125

Leu Glu Lys Ile Asn Val Ala Asp Ile Ile Asn Gly Ala Gln Glu Lys
        130                 135                 140

Cys Val Leu Pro Pro Met Asp Gly Tyr Pro His Cys Glu Gly Lys Ile
145                 150                 155                 160

Lys Trp Met Lys Asp Met Trp Arg Ser Asp Pro Cys Tyr Ala Asp Tyr
                165                 170                 175

Gly Val Asp Gly Ser Thr Cys Ser Phe Phe Ile Tyr Leu Ser Glu Val
                180                 185                 190

Glu Asn Trp Cys Pro His Leu Pro Trp Arg Ala Lys Asn Pro Tyr Glu
            195                 200                 205

Glu Ala Asp His Asn Ser Leu Ala Glu Ile Arg Thr Asp Phe Asn Ile
        210                 215                 220

Leu Tyr Ser Met Met Lys Lys His Glu Glu Phe Arg Trp Met Arg Leu
225                 230                 235                 240

Arg Ile Arg Arg Met Ala Asp Ala Trp Ile Gln Ala Ile Lys Ser Leu
                245                 250                 255

Ala Glu Lys Gln Asn Leu Glu Lys Arg Lys Arg Lys Val Leu Val
                260                 265                 270

His Leu Gly Leu Leu Thr Lys Glu Ser Gly Phe Lys Ile Ala Glu Thr
            275                 280                 285

Ala Phe Ser Gly Gly Pro Leu Gly Glu Leu Val Gln Trp Ser Asp Leu
        290                 295                 300

Ile Thr Ser Leu Tyr Leu Leu Gly His Asp Ile Arg Ile Ser Ala Ser
305                 310                 315                 320

Leu Ala Glu Leu Lys Glu Ile Met Lys Lys Val Val Gly Asn Arg Ser
                325                 330                 335

Gly Cys Pro Thr Val Gly Asp Arg Ile Val Glu Leu Ile Tyr Ile Asp
            340                 345                 350

Ile Val Gly Leu Ala Gln Phe Lys Lys Thr Leu Gly Pro Ser Trp Val
        355                 360                 365

His Tyr Gln Cys Met Leu Arg Val Leu Asp Ser Phe Gly Thr Glu Pro
        370                 375                 380

Glu Phe Asn His Ala Asn Tyr Ala Gln Ser Lys Gly His Lys Thr Pro
385                 390                 395                 400

Trp Gly Lys Trp Asn Leu Asn Pro Gln Gln Phe Tyr Thr Met Phe Pro
                405                 410                 415

His Thr Pro Asp Asn Ser Phe Leu Gly Phe Val Val Glu Gln His Leu
                420                 425                 430

Asn Ser Ser Asp Ile His His Ile Asn Glu Ile Lys Arg Gln Asn Gln
            435                 440                 445

Ser Leu Val Tyr Gly Lys Val Asp Ser Phe Trp Lys Asn Lys Lys Ile
```

```
                    450                 455                 460
Tyr Leu Asp Ile Ile His Thr Tyr Met Glu Val His Ala Thr Val Tyr
465                 470                 475                 480

Gly Ser Ser Thr Lys Asn Ile Pro Ser Tyr Val Lys Asn His Gly Ile
                485                 490                 495

Leu Ser Gly Arg Asp Leu Gln Phe Leu Arg Glu Thr Lys Leu Phe
                500                 505                 510

Val Gly Leu Gly Phe Pro Tyr Glu Gly Pro Ala Pro Leu Glu Ala Ile
            515                 520                 525

Ala Asn Gly Cys Ala Phe Leu Asn Pro Lys Phe Asn Pro Pro Lys Ser
530                 535                 540

Ser Lys Asn Thr Asp Phe Phe Ile Gly Lys Pro Thr Leu Arg Glu Leu
545                 550                 555                 560

Thr Ser Gln His Pro Tyr Ala Glu Val Phe Ile Gly Arg Pro His Val
                565                 570                 575

Trp Thr Val Asp Leu Asn Asn Gln Glu Val Glu Asp Ala Val Lys
                580                 585                 590

Ala Ile Leu Asn Gln Lys Ile Glu Pro Tyr Met Pro Tyr Glu Phe Thr
            595                 600                 605

Cys Glu Gly Met Leu Gln Arg Ile Asn Ala Phe Ile Glu Lys Gln Asp
610                 615                 620

Phe Cys His Gly Gln Val Met Trp Pro Pro Leu Ser Ala Leu Gln Val
625                 630                 635                 640

Lys Leu Ala Glu Pro Gly Gln Ser Cys Lys Gln Val Cys Gln Glu Ser
                645                 650                 655

Gln Leu Ile Cys Glu Pro Ser Phe Phe Gln His Leu Asn Lys Asp Lys
                660                 665                 670

Asp Met Leu Lys Tyr Lys Val Thr Cys Gln Ser Ser Glu Leu Ala Lys
                675                 680                 685

Asp Ile Leu Val Pro Ser Phe Asp Pro Lys Asn Lys His Cys Val Phe
            690                 695                 700

Gln Gly Asp Leu Leu Phe Ser Cys Ala Gly Ala His Pro Arg His
705                 710                 715                 720

Gln Arg Val Cys Pro Cys Arg Asp Phe Ile Lys Gly Gln Val Ala Leu
                725                 730                 735

Cys Lys Asp Cys Leu
            740

(2) INFORMATION FOR SEQ ID NO:21:

(i) SEQUENCE CHARACTERISTICS:
        (A) LENGTH: 1692 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 2..1366

(xi) SEQUENCE DESCRIPTION: SEQ ID NO:21:

G ACA GCA TTC AGC GGT GGC CCT CTG GGT GAA CTC GTT CAG TGG AGT      46
  Thr Ala Phe Ser Gly Gly Pro Leu Gly Glu Leu Val Gln Trp Ser
                745                 750                 755

GAC TTA ATC ACA TCT CTG TAC CTG CTG GGC CAT GAC ATC CGG ATC TCG    94
Asp Leu Ile Thr Ser Leu Tyr Leu Leu Gly His Asp Ile Arg Ile Ser
                760                 765                 770
```

-continued

| | | |
|---|---|---|
| GCC TCA CTG GCT GAG CTC AAG GAG ATA ATG AAG AAG GTT GTT GGA AAC<br>Ala Ser Leu Ala Glu Leu Lys Glu Ile Met Lys Lys Val Val Gly Asn<br>775                  780                     785 | 142 |
| CGG TCT GGC TGT CCA ACT GTA GGA GAC AGA ATC GTT GAG CTG ATT TAT<br>Arg Ser Gly Cys Pro Thr Val Gly Asp Arg Ile Val Glu Leu Ile Tyr<br>790                  795                     800                   805 | 190 |
| ATC GAT ATT GTG GGA CTT GCT CAA TTT AAG AAA ACA CTA GGG CCA TCC<br>Ile Asp Ile Val Gly Leu Ala Gln Phe Lys Lys Thr Leu Gly Pro Ser<br>810                  815                 820 | 238 |
| TGG GTT CAT TAC CAG TGC ATG CTC CGG GTG CTA GAC TCC TTT GGA ACA<br>Trp Val His Tyr Gln Cys Met Leu Arg Val Leu Asp Ser Phe Gly Thr<br>825                 830                   835 | 286 |
| GAA CCT GAG TTC AAT CAT GCG AGC TAT GCC CAG TCA AAA GGC CAC AAG<br>Glu Pro Glu Phe Asn His Ala Ser Tyr Ala Gln Ser Lys Gly His Lys<br>840                  845                 850 | 334 |
| ACC CCC TGG GGA AAG TGG AAT CTG AAC CCG CAG CAG TTT TAC ACC ATG<br>Thr Pro Trp Gly Lys Trp Asn Leu Asn Pro Gln Gln Phe Tyr Thr Met<br>855                 860                 865 | 382 |
| TTC CCT CAT ACC CCA GAC AAC AGC TTT CTG GGC TTC GTG GTG GAG CAG<br>Phe Pro His Thr Pro Asp Asn Ser Phe Leu Gly Phe Val Val Glu Gln<br>870                 875                    880                   885 | 430 |
| CAC CTG AAC TCC AGC GAC ATT CAC CAC ATC AAC GAG ATC AAA AGG CAG<br>His Leu Asn Ser Ser Asp Ile His His Ile Asn Glu Ile Lys Arg Gln<br>890                  895                 900 | 478 |
| AAC CAG TCC CTT GTG TAT GGC AAA GTG GAT AGT TTC TGG AAG AAT AAG<br>Asn Gln Ser Leu Val Tyr Gly Lys Val Asp Ser Phe Trp Lys Asn Lys<br>905                 910                 915 | 526 |
| AAA ATC TAC CTG GAT ATC ATT CAC ACG TAC ATG GAA GTG CAC GCC ACT<br>Lys Ile Tyr Leu Asp Ile Ile His Thr Tyr Met Glu Val His Ala Thr<br>920                 925                 930 | 574 |
| GTT TAT GGC TCC AGT ACC AAG AAC ATT CCC AGT TAC GTG AAA AAC CAT<br>Val Tyr Gly Ser Ser Thr Lys Asn Ile Pro Ser Tyr Val Lys Asn His<br>935                 940                 945 | 622 |
| GGC ATT CTC AGT GGA CGT GAC CTG CAG TTT CTT CTC CGG GAA ACC AAG<br>Gly Ile Leu Ser Gly Arg Asp Leu Gln Phe Leu Leu Arg Glu Thr Lys<br>950                 955                 960                   965 | 670 |
| CTG TTC GTT GGG CTC GGA TTC CCT TAT GAA GGC CCA GCT CCC CTG GAG<br>Leu Phe Val Gly Leu Gly Phe Pro Tyr Glu Gly Pro Ala Pro Leu Glu<br>970                 975                 980 | 718 |
| GCC ATC GCG AAT GGA TGT GCT TTC CTG AAC CCC AAG TTC AAC CCT CCC<br>Ala Ile Ala Asn Gly Cys Ala Phe Leu Asn Pro Lys Phe Asn Pro Pro<br>985                 990                 995 | 766 |
| AAA AGC AGC AAA AAC ACA GAC TTC TTC ATT GGC AAG CCA ACA CTG AGA<br>Lys Ser Ser Lys Asn Thr Asp Phe Phe Ile Gly Lys Pro Thr Leu Arg<br>1000                1005              1010 | 814 |
| GAG CTG ACA TCC CAG CAT CCT TAC GCA GAA GTC TTC ATC GGC CGG CCA<br>Glu Leu Thr Ser Gln His Pro Tyr Ala Glu Val Phe Ile Gly Arg Pro<br>1015                1020              1025 | 862 |
| CAC GTC TGG ACT GTG GAT CTC AAT AAC CGA GAG GAA GTA GAA GAT GCA<br>His Val Trp Thr Val Asp Leu Asn Asn Arg Glu Glu Val Glu Asp Ala<br>1030                1035              1040              1045 | 910 |
| GTA AAA GCC ATC TTA AAC CAG AAG ATT GAG CCG TAT ATG CCA TAT GAG<br>Val Lys Ala Ile Leu Asn Gln Lys Ile Glu Pro Tyr Met Pro Tyr Glu<br>1050                1055              1060 | 958 |
| TTC ACA TGT GAA GGC ATG CTG CAG AGA ATC AAC GCT TTC ATT GAA AAA<br>Phe Thr Cys Glu Gly Met Leu Gln Arg Ile Asn Ala Phe Ile Glu Lys<br>1065                1070              1075 | 1006 |
| CAG GAC TTC TGC CAT GGC CAA GTG ATG TGG CCG CCC CTC AGC GCC CTG<br>Gln Asp Phe Cys His Gly Gln Val Met Trp Pro Pro Leu Ser Ala Leu<br>1080                1085              1090 | 1054 |

-continued

```
CAG GTT AAG CTG GCT GAG CCA GGG CAG TCC TGC AAA CAG GTG TGC CAG      1102
Gln Val Lys Leu Ala Glu Pro Gly Gln Ser Cys Lys Gln Val Cys Gln
    1095                1100                1105

GAG AGC CAG CTC ATC TGC GAG CCA TCC TTC TTT CAA CAC CTC AAC AAG      1150
Glu Ser Gln Leu Ile Cys Glu Pro Ser Phe Phe Gln His Leu Asn Lys
1110                1115                1120                1125

GAA AAG GAC CTG CTG AAG TAT AAG GTG ACC TGC CAA AGC TCA GAA CTG      1198
Glu Lys Asp Leu Leu Lys Tyr Lys Val Thr Cys Gln Ser Ser Glu Leu
                1130                1135                1140

TAC AAG GAC ATC CTG GTG CCC TCC TTC TAC CCC AAG AGC AAG CAC TGT      1246
Tyr Lys Asp Ile Leu Val Pro Ser Phe Tyr Pro Lys Ser Lys His Cys
            1145                1150                1155

GTG TTC CAA GGG GAC CTC CTG CTC TTC AGT TGT GCC GGA GCC CAT CCC      1294
Val Phe Gln Gly Asp Leu Leu Leu Phe Ser Cys Ala Gly Ala His Pro
        1160                1165                1170

ACA CAC CAG CGG ATC TGC CCC TGC CGG GAC TTC ATC AAG GGC CAA GTG      1342
Thr His Gln Arg Ile Cys Pro Cys Arg Asp Phe Ile Lys Gly Gln Val
    1175                1180                1185

GCC CTC TGC AAA GAC TGC CTA TAG CATCGCTGCC CTGAATTAAC TCAGACGGGA      1396
Ala Leu Cys Lys Asp Cys Leu  *
1190                1195

AAGACGTGGC TCCACTGGGC AGGGCCAAGG GGCACAAAGA CATTCAGGGA CTCTGACCAG     1456

AGCCTGAGAT CTTTGGTCCA GGGCTTGAGT TTAGTACCGC TCCAGCCACA GCCAGTGCAT     1516

CCCAGTTTAC ACCAAAACCA CAAGGGAACA GGTTAGAACA GGAACCTGGG TTCTCCTCAG     1576

TGTAAGGAAT GTCCTCTCTG TCTGGGAGAT CGAGCGACTG TAGGGAAAGG ATCCAGGCAG     1636

TTGCTCCCGG GAATTTTTTT TTTTTTTTTT TTTAAAGAAG GGATAAAAGT CCGGAG         1692

(2) INFORMATION FOR SEQ ID NO:22:

(i) SEQUENCE CHARACTERISTICS:
        (A) LENGTH: 454 amino acids
        (B) TYPE: amino acid
        (D) TOPOLOGY: linear (ii) MOLECULE TYPE: protein (xi) SEQUENCE DESCRIPTION: SEQ ID NO:22:

Thr Ala Phe Ser Gly Gly Pro Leu Gly Glu Leu Val Gln Trp Ser Asp
  1               5                  10                  15

Leu Ile Thr Ser Leu Tyr Leu Leu Gly His Asp Ile Arg Ile Ser Ala
                 20                  25                  30

Ser Leu Ala Glu Leu Lys Glu Ile Met Lys Lys Val Val Gly Asn Arg
             35                  40                  45

Ser Gly Cys Pro Thr Val Gly Asp Arg Ile Val Glu Leu Ile Tyr Ile
         50                  55                  60

Asp Ile Val Gly Leu Ala Gln Phe Lys Lys Thr Leu Gly Pro Ser Trp
 65                  70                  75                  80

Val His Tyr Gln Cys Met Leu Arg Val Leu Asp Ser Phe Gly Thr Glu
                 85                  90                  95

Pro Glu Phe Asn His Ala Ser Tyr Ala Gln Ser Lys Gly His Lys Thr
            100                 105                 110

Pro Trp Gly Lys Trp Asn Leu Asn Pro Gln Gln Phe Tyr Thr Met Phe
        115                 120                 125

Pro His Thr Pro Asp Asn Ser Phe Leu Gly Phe Val Val Glu Gln His
    130                 135                 140

Leu Asn Ser Ser Asp Ile His His Ile Asn Glu Ile Lys Arg Gln Asn
145                 150                 155                 160
```

```
Gln Ser Leu Val Tyr Gly Lys Val Asp Ser Phe Trp Lys Asn Lys Lys
                165                 170                 175

Ile Tyr Leu Asp Ile Ile His Thr Tyr Met Glu Val His Ala Thr Val
            180                 185                 190

Tyr Gly Ser Ser Thr Lys Asn Ile Pro Ser Tyr Val Lys Asn His Gly
        195                 200                 205

Ile Leu Ser Gly Arg Asp Leu Gln Phe Leu Leu Arg Glu Thr Lys Leu
    210                 215                 220

Phe Val Gly Leu Gly Phe Pro Tyr Glu Gly Pro Ala Pro Leu Glu Ala
225                 230                 235                 240

Ile Ala Asn Gly Cys Ala Phe Leu Asn Pro Lys Phe Asn Pro Pro Lys
                245                 250                 255

Ser Ser Lys Asn Thr Asp Phe Phe Ile Gly Lys Pro Thr Leu Arg Glu
                260                 265                 270

Leu Thr Ser Gln His Pro Tyr Ala Glu Val Phe Ile Gly Arg Pro His
            275                 280                 285

Val Trp Thr Val Asp Leu Asn Asn Arg Glu Val Glu Asp Ala Val
        290                 295                 300

Lys Ala Ile Leu Asn Gln Lys Ile Glu Pro Tyr Met Pro Tyr Glu Phe
305                 310                 315                 320

Thr Cys Glu Gly Met Leu Gln Arg Ile Asn Ala Phe Ile Glu Lys Gln
                325                 330                 335

Asp Phe Cys His Gly Gln Val Met Trp Pro Pro Leu Ser Ala Leu Gln
                340                 345                 350

Val Lys Leu Ala Glu Pro Gly Gln Ser Cys Lys Gln Val Cys Gln Glu
            355                 360                 365

Ser Gln Leu Ile Cys Glu Pro Ser Phe Phe Gln His Leu Asn Lys Glu
    370                 375                 380

Lys Asp Leu Leu Lys Tyr Lys Val Thr Cys Gln Ser Ser Glu Leu Tyr
385                 390                 395                 400

Lys Asp Ile Leu Val Pro Ser Phe Tyr Pro Lys Ser Lys His Cys Val
                405                 410                 415

Phe Gln Gly Asp Leu Leu Leu Phe Ser Cys Ala Gly Ala His Pro Thr
            420                 425                 430

His Gln Arg Ile Cys Pro Cys Arg Asp Phe Ile Lys Gly Gln Val Ala
        435                 440                 445

Leu Cys Lys Asp Cys Leu
    450                 455

(2) INFORMATION FOR SEQ ID NO:23:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:23:

GCTATAGGCA GTCTTTGC                                                                 18

(2) INFORMATION FOR SEQ ID NO:24:
```

```
        (i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:24:

TGTAGGAGAC AGAATCGTTG AGC                                          23

(2) INFORMATION FOR SEQ ID NO:25:

(i) SEQUENCE CHARACTERISTICS:
            (A) LENGTH: 21 base pairs
            (B) TYPE: nucleic acid
            (C) STRANDEDNESS: single
            (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:25:

CCGGCACAAC TGAAGAGCAG G                                            21

(2) INFORMATION FOR SEQ ID NO:26:

(i) SEQUENCE CHARACTERISTICS:
            (A) LENGTH: 24 base pairs
            (B) TYPE: nucleic acid
            (C) STRANDEDNESS: single
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:26:

CGCGTAATAC GACTCACTAT AGGG                                         24

(2) INFORMATION FOR SEQ ID NO:27:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:27:

GTTGTCTGGG GTATGAGGGA AC                                           22

(2) INFORMATION FOR SEQ ID NO:28:

(i) SEQUENCE CHARACTERISTICS:
            (A) LENGTH: 23 base pairs
            (B) TYPE: nucleic acid
            (C) STRANDEDNESS: single
```

(D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:28:

GACTTGATTG CTTGGATCCA TGC                                               23

(2) INFORMATION FOR SEQ ID NO:29:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:29:

GTTAAGAGCC AAGGACAGGT GAAG                                              24

(2) INFORMATION FOR SEQ ID NO:30:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:30:

AGGGTAGCCG TCCATAGGAG GC                                                22

(2) INFORMATION FOR SEQ ID NO:31:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:31:

CCATGGTATC CTCAGTGGAC GG                                                22

(2) INFORMATION FOR SEQ ID NO:32:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: other nucleic acid -continued (iii) HYPOTHETICAL: NO (iv) ANTI-SENSE: YES (xi) SEQUENCE DESCRIPTION: SEQ ID NO:32:

GCGCAATTAA CCCTCACTAA AGGG                                              24

(2) INFORMATION FOR SEQ ID NO:33:

(i) SEQUENCE CHARACTERISTICS:
            (A) LENGTH: 111 base pairs
            (B) TYPE: nucleic acid
            (C) STRANDEDNESS: single
            (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:33:

CGCGCTCTAG ATGCAAAGAT GAAATACACC TCTTACATTT TGGCTTTCCA ATTGTGTATT        60

GTTTTGGGTT CTTTGGGTTG TTACTGTCAG GATGGCCCGT ATGCCGGTGT C                 111

(2) INFORMATION FOR SEQ ID NO:34:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (ii) MOLECULE TYPE: other nucleic acid (iii) HYPOTHETICAL: NO (iv) ANTI-SENSE: YES (xi) SEQUENCE DESCRIPTION: SEQ ID NO:34:

GCGGTCGACC TACTATAGGC AGTCTTTGCA GAGGG                                   35

N-ACETYLGLUCOSAMINYLTRANSFERASE V PROTEINS AND CODING SEQUENCES

This application is a continuation-in-part of U.S. Ser. No. 08/016,863, filed Feb. 10, 1993, now U.S. Pat. No. 5,602,003, which application is a continuation-in-part of U.S. Ser. No. 07/905,795, filed Jun. 29, 1992, now abandoned.

FIELD OF THE INVENTION

The field of this invention is the area of protein glycosylation, specifically the area of the particular enzyme, UDP N-acetylglucosaminyltransferase V, involved in the expression of the β(1,6) branch structure found in tri- and tetraantennary N-linked oligosaccharides. The field relates to purified active enzyme, the amino acid sequences of rat, human and hamster GlcNAc T-V proteins, genes encoding active enzyme and cell lines genetically engineered to express a nucleotide sequence encoding active enzyme.

BACKGROUND OF THE INVENTION

UDP-N-acetylglucosamine: α-6-D-mannoside β1,6-N-acetylglucosaminyltransferase V (EC 2.4.1.155) is the Golgi enzyme responsible for the synthesis of the β(1,6) branch structure of tri- and tetraantennary N-linked oligosaccharides. For brevity, this enzyme is abbreviated GlcNAc T-V herein. GlcNAc T-V activity has been found in many tissues and cell types.

Altered glycosylation of membrane glycoproteins and glycolipids is observed in mammalian cells transformed with diverse tumor viruses, carcinogens, or transfection with certain oncogenes. In some cases, there is a quantitative increase in a particular substituent, e.g., sialylation. In other instances, there is the reappearance of an oligosaccharide structure in the tumor which is normally only found in fetal tissue; for instance, certain Lewis histo-blood group antigens have been detected in adenocarcinomas.

Qualitative differences in oligosaccharides may also be observed in certain transformed cells. BHK fibroblasts transformed with polyoma virus or with Rous sarcoma virus display more highly branched complex N-linked oligosaccharides than do the corresponding normal cells. The expression of the β1,6 branch structure (-[GlcNAc-β(1,6)Man-α(1,6)Man]-) found in tri- and tetraantennary N-linked oligosaccharides is increased in the transformed cells. This has been correlated with a 2 to 3-fold increase in the specific activity of GlcNAc T-V. Transformation of murine cells with polyoma viruses, adenovirus, tumorigenic DNA and either the ras or the fps/fes oncogenes also resulted in increased GlcNAc T-V activity. By contrast, several other glycosyl transferases involved in N-linked glycosylation are unchanged in the transformed cells. The mechanism for the increased specific activity of GlcNAc T-V in transformed cells is not known.

The increase in the β(1,6) branching of the cell surface-bound oligosaccharides has been associated, at least in some cases, with capacity for metastasis. Increased levels of β-1,6 branching over the level in normal tissue has been observed for some human breast tumor tissues.

Certain mammalian glycosyltransferases from the N-linked glycosylation pathway have been purified and characterized. The enzymatic machinery for the glycosylation of proteins in mammalian cells is generally located in the membranes of the Golgi apparatus. α(1,3) mannoside β(1,2) UDP-N-acetylglucosaminyltransferase I (GlcNAc T-I) (EC 2.4.1.101) and UDP-N-acetylglucosaminyltransferase II (GlcNAc T-II) (EC 2.4.1.143) have been purified from rabbit liver and rat liver, respectively. GlcNAc T-I has been purified 7000-fold from a Triton X-100 extract of rabbit liver acetone powder by two rounds of affinity chromatography over UDP-hexanolamine agarose, in the first round by elution with NaCl, and in the second round by elution with UDP (Oppenheimer and Hill (1981) *J. Biol. Chem.* 256:799–804). GlcNAc T-II (UDP-N-acetylglucosaminyl: α-D-mannoside β(1,2) N-acetylglucosaminyltransferase II) was purified 60,000-fold from rat liver by Triton X-100 extraction of rat liver membranes, followed by chromatography over carboxymethyl-cellulose, hydroxylapatite, and sequential elutions using NaCl, UDP-GlcNAc and EDTA from 5-mercuri-UDP-GlcNAc-thiopropyl-SEPHAROSE, Affi-Gel (Bio-Rad Laboratories, Richmond, Calif.) blue affinity chromatography and finally UDP-GlcNAc-SEPHAROSE (Bendiak and Schachter (1987) *J. Biol. Chem.* 262:5775–5783).

The cDNA encoding a rat liver Golgi sialyltransferase (β-galactoside α(2,6)-sialyltransferase (EC 2.4.99.1) has been cloned and sequenced (Weinstein et al. (1987) *J. Biol. Chem.* 262:17735–17743). The corresponding enzyme has been purified 23,000-fold from Triton CF-54 extracts of rat liver membranes by three rounds of affinity chromatography over CDP-hexanolamineagarose (Weinstein et al. (1982) *J. Biol. Chem.* 257:13835–13844). Soluble recombinant glycosyltranferases are described in U.S. Pat. No. 5,032,519, issued Jul. 16, 1991, incorporated by reference herein.

A portion of the work related to this invention has been published (Shoreibah et al. (1992) *J. Biol. Chem.* 267:2920–2927; Shoreibah et al. (1993) *J. Biol. Chem.* 268:15381–15385).

SUMMARY OF THE INVENTION

An object of this invention is a substantially pure N-acetylglucosaminyltransferase V enzyme. GlcNAc T-V can be substantially purified from a detergent (e.g., Triton X-100) extract of acetone-insoluble protein prepared from a biological material such as rat kidney by affinity chromatography over a solid support to which a substrate analog ligand is covalently linked, preferably UDP-hexanolamine-agarose, followed by affinity chromatography over an enzyme inhibitor of GlcNAc T-V (e.g., the oligosaccharide inhibitor disclosed herein) linked to a solid support via bovine serum albumin and a further purification step of affinity chromatography using a matrix to which a substrate analog ligand is attached, e.g., over UDP-hexanolamine-agarose. The substantially pure enzyme prepared from rat kidney has a specific activity of at least about 18 µmol/(min·mg) in the assay disclosed herein, and migrates as a doublet of 69 and 75 kDa on SDS-PAGE as described herein; only these two bands are visible by silver staining. The substantially pure GlcNAc T-V of this invention will be useful in in vitro enzymatic reactions of this enzyme.

Additional aspects of the present invention are genetically engineered, soluble GlcNAc T-V enzymatically active proteins, as exemplified herein by a soluble GlcNAc T-V derived from the rat sequence, which has Gln at the N-terminus, followed by an amino acid sequence as given in SEQ ID NO:16, amino acid 70 through amino acid 741. Also within the present invention are nucleic acid molecules genetically engineered to produce soluble GlcNAc T-V proteins from cell-free culture media. Preferably, EDTA is present during purification steps to prevent proteolytic degradation; preferred purification steps are copper chelating column chromatography and CM Sephadex chromatography.

Also embodied in the invention are genomic and cDNA sequences encoding glcNAc T-V, the amino acid sequences of GlcNAc T-V enzymes, and recombinant host cells genetically engineered to express sequences encoding active GlcNAc T-V enzymes.

Also provided by this invention are polyclonal and monoclonal antibodies specific for GlcNAc T-V. These antibodies will also bind to and be useful for detection and isolation of GlcNAc T-V from mammalian and other sources. It is understood that the molecular weight, kinetic parameters and primary amino acid sequence of GlcNAc T-V from a source other than rat kidney may vary from those values disclosed herein for the rat kidney enzyme.

Also provided in this invention is GlcNAc T-V produced by recombinant DNA technology in prokaryotic or eukaryotic host cells. Disclosed in this invention are the complete amino acid sequences for rat, human and hamster (e.g., Chinese Hamster Ovary (CHO) cells) GlcNAc T-V and nucleotide sequences encoding rat, human and hamster GlcNAc T-V. Examples of methods of producing recombinant active GlcNAc T-V by recombinant DNA technology are disclosed. The exemplified amino acid sequences and the nucleotide sequences encoding GlcNAc T-V, and subsequences within, as understood in the art, will be useful for isolating GlcNAc T-V coding sequences from a wide range of species and for producing useful quantities of GlcNAc T-V by recombinant DNA technology.

Further objects of this invention are cDNA clones encoding GlcNAc T-V and genomic clones encoding GlcNAc T-V. The antibodies raised against rat kidney GlcNAc T-V (or other GlcNAc T-V's or peptide-specific antibodies for GlcNAc T-V) can be used to detect expression of GlcNAc T-V from sources other than rat kidney by virtue of cross-reactivity with those other GlcNAc T-V enzymes; alternatively, these antibodies can be used to screen cDNA expression libraries. Sequences encoding GlcNAc T-V from rat, human and hamster (i.e., Chinese hamster ovary) cells and a partial coding sequence from mouse are presented herein. Similarly, the degenerate oligonucleotide probes and/or the coding sequence and/or the amplimer sequences of the present invention can be used to screen genomic or cDNA libraries constructed using nucleic acids from sources other than those exemplified herein, or these can be used to prepare primers to amplify sequences encoding GlcNAc T-V from mRNA populations prepared from rat kidney or from other animal cells. The cDNA and/or genomic sequences encoding GlcNAc T-V will be useful in directing the recombinant expression of GlcNAc T-V.

Further objects of this invention are nucleotide sequences encoding rat GlcNAc T-V, and nucleotide sequences encoding GlcNAc T-V from other vertebrate, preferably mammalian, sources, including cDNA and genomic sequences. The nucleotide sequence encoding rat GlcNac T-V is provided herein as SEQ ID NO:15, from an ATG translation start codon beginning at nucleotide 299 through a translation stop codon ending at nucleotide 2521. The nucleotide sequence encoding human GlcNac T-V is provided herein as SEQ ID NO:19, from an ATG translation start codon beginning at nucleotide 38 through a translation stop codon ending at nucleotide 2263. The nucleotide sequence encoding hamster (i.e., CHO cells) GlcNac T-V is provided herein as SEQ ID NO:17, from an ATG translation start codon beginning at nucleotide 145 through a translation stop codon ending at nucleotide 2367. A partial mouse cDNA sequence is given in SEQ ID NO:21.

The skilled artisan recognizes that there will be more than one nucleotide sequence capable of encoding the same amino acid sequence due to the degeneracy of the genetic code. Exemplary GlcNAc T-V amino acid sequences are given in SEQ ID NOs 16, 18 and 20. These sequences, and sequence variants thereof which encode functionally equivalent GlcNAc T-V, can be used to express GlcNAc T-V in a desired recombinant host cell. The GlcNAc T-V coding sequences from other vertebrate species, preferably from mammals, will be highly homologous at the nucleotide sequence level to the exemplified rat, hamster and human GlcNAc T-V coding sequence disclosed herein. Functionally equivalent GlcNAc T-V coding sequences with at least 70%, preferably at least 80%, more preferably at least 90% nucleotide sequence homology to the exemplified rat, human and/or hamster (CHO) GlcNAc T-V coding sequences can be identified and isolated from cDNA libraries prepared from mRNA sources other than rat, human and CHO cells, using well-known DNA-DNA hybridization technology and the exemplified GlcNAc T-V coding sequences provided herein. Also contemplated are genomic clones encoding GlcNAc T-V, which clones comprise the natural regulatory sequences. It is understood that any intron sequences in genomic GlcNAc T-V are not to be included in sequence comparisons to the exemplified full-length coding sequence, and gaps may be introduced to maximize homology.

Additional objects of this invention are DNA molecules containing a first nucleotide sequence encoding an enzymatically active GlcNAc T-V and a second nucleotide sequence not found associated with the GlcNAc T-V coding sequence in nature, termed an exogenous nucleotide sequence herein. Preferably the first nucleotide sequence encodes a polypeptide sequence with GlcNAc T-V activity, said polypeptide having an amino acid sequence as given in FIG. 12 and in SEQ ID NOS:16, 20 and 18 (from rat, human and CHO cells, respectively).

Still further objects of the invention are cells genetically engineered to contain a DNA molecule containing a first nucleotide sequence encoding an enzymatically active GlcNAc T-V and a second nucleotide sequence not found associated with the GlcNAc T-V coding sequence in nature. Mammalian cells are preferred for recombinant expression of GlcNAc T-V coding sequences. Particularly preferred are COS-7 cells and CHO (Chinese Hamster Ovary) cells. The exemplified rat, CHO and human GlcNAc T-V amino acid sequences are particularly preferred, preferably encoded by the exemplified nucleotide coding sequences as in FIG. 11 or SEQ ID NO:15 from nucleotide 299 through nucleotide 2521, in SEQ ID NO:17 from nucleotide 145 through nucleotide 2367, and in SEQ ID NO:19 from nucleotide 38 through nucleotide 2263.

BRIEF DESCRIPTION OF THE DRAWINGS

FIG. 6 is a reproduction of an autoradiogram resulting from a Northern hybridization experiment in which rat kidney mRNA was size-separated by agarose gel electrophoresis and probed with radioactive HindIII/BglI fragment of the mouse partial GlcNAc T-V clone.

FIGS. 10A–10E, taken together in sequence, presents the cDNA sequence encoding rat GlcNAc T-V and the deduced amino acid sequence which correspond to SEQ ID NO:15 and SEQ ID NO:16, respectively.

FIG. 11A–11F, taken in sequence, presents a comparison of the nucleotide sequences encoding human (SEQ ID NO:19), CHO (SEQ ID NO:17), mouse (SEQ ID NO:21) and rat (SEQ ID NO:15) GlcNAc T-V. The rat coding region extends from an ATG starting at nucleotide 299 (bold) to a stop codon ending at nucleotide 2524 (bold). The mouse sequence represents the analysis of a partial cDNA clone starting at nucleotide 1159 according to the numbering for SEQ ID NO:15.

FIG. 12A–12B, taken in sequence, presents a comparison of the deduced amino acid sequences of human (SEQ ID NO:20), CHO (SEQ ID NO:18), mouse (SEQ ID NO:22) and rat (SEQ ID NO:16) GlcNAc T-V. The human sequence contains an insertion of a valine at amino acid 109 as compared to the CHO and rat sequences. The mouse sequence represents the analysis of a partial cDNA clone starting at amino acid 288 according to the numbering in SEQ ID NO:16. The asterisks signify the end of the protein.

DETAILED DESCRIPTION OF THE INVENTION

Figure 1:
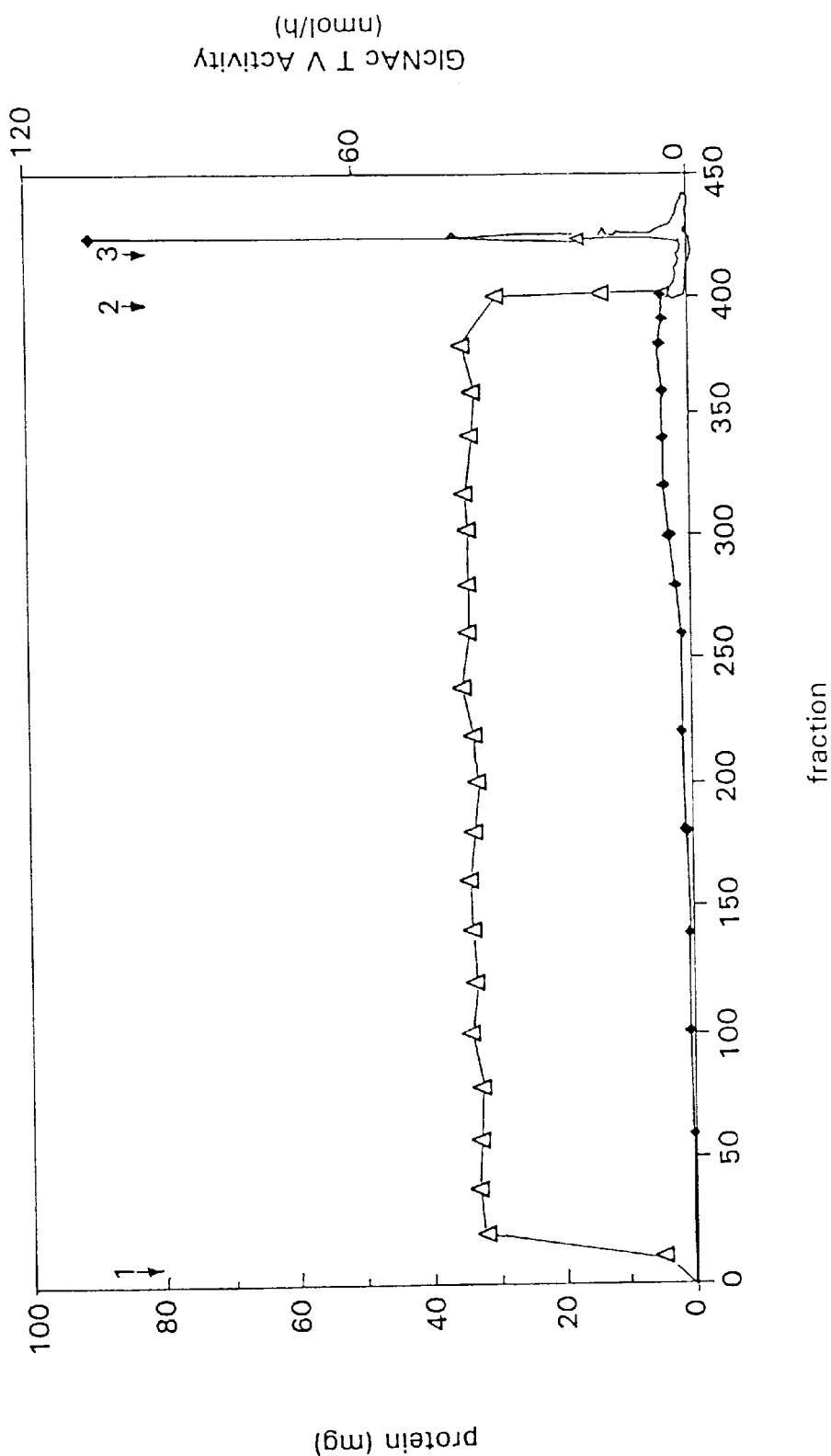
FIG. 1 illustrates the elution profile for rat kidney GlcNAc T-V from UDP-hexanolamine SEPHAROSE. At the first arrow, 3 L of freshly prepared and dialyzed Triton extract of acetone powder from rat kidney was applied to a 1.2×7 cm column of UDP-hexanolamine (14 $\mu$mol/ml of gel) SEPHAROSE. At the arrow labeled "2, " the column was washed with about 400 ml of loading buffer. At the third arrow, the column was eluted with loading buffer, further containing NaCl at a final concentration of 500 mM. Fractions were collected after elution and assayed for protein content ($\Delta$) and for GlcNAc T-V activity ($\blacklozenge$).
Figure 2:
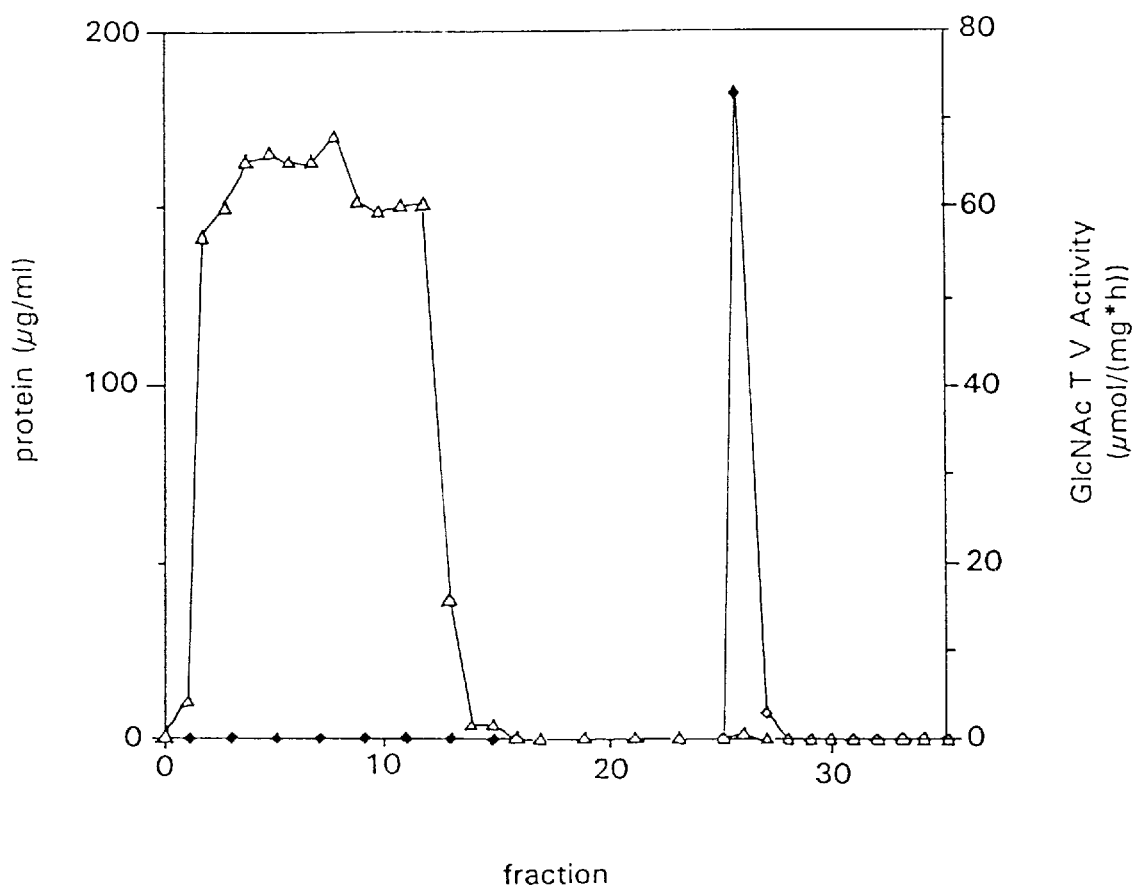
FIG. 2 illustrates the chromatography of rat kidney GlcNAc T-V over an inhibitor-BSA SEPHAROSE column. Pooled and dialyzed fractions from the UDP-hexanolamine column (about 100 ml) were brought to 1 mM UDP-GlcNAc and (at the first arrow) loaded onto a 1.2×3 cm column of inhibitor-BSA-SEPHAROSE pre-equilibrated with loading buffer (50 mM sodium cacodylate pH 6.5, 0.1% Triton X-100, 20% glycerol, 0.05% sodium azide). At the second arrow, the column was washed with about 20 ml of loading buffer. At the third arrow, the column was brought to room temperature and eluted with loading buffer which was made 500 mM NaCl and adjusted to a pH of 8.0. Fractions were collected and assayed for protein content (Δ) and for GlcNAc T-V activity (♦).

In general, the terminology used herein is standard, as understood by those of ordinary skill in the fields of molecular biology, biochemistry, protein chemistry, and cell biology. For added clarity, certain terms are defined herein. Standard abbreviations are used; these abbreviations are consistent with those used and approved by scientific journals in the field (e.g., Journal of Biological Chemistry, Science, Nature, etc.).

Methods used herein are either specifically referenced or are sufficiently well known as to be available in at least one of several readily accessible published collections of methodologies (See, e.g., Sambrook et al. (1989) *Molecular Cloning, A Laboratory Manual* (2nd ed.), Cold Spring Harbor Laboratory, Cold Spring Harbor, N.Y., Innis et al. (1990) *PCR Protocols: A Guide to Methods and Applications*, Academic Press, New York, N.Y., and references cited therein, all incorporated herein by reference).

Complementary DNA (cDNA) synthesis involves the in vitro synthesis of a double stranded DNA sequence by enzymatic reverse transcription of mRNA isolated from donor cells. In the present invention, polyadenylated RNA is prepared from rat 1-EJ cultured cells (described in Peles et al. (1992) *Cell* 69:205–216). Rat 1-EJ cells are Rat 1 fibroblasts which have been transfected with the human EJ gene, an activated Harvey ras gene, which is believed to elevate expression levels for GlcNAc T-V. cDNA molecules and/or libraries can be used for isolating a DNA sequence encoding a selected protein when the entire amino acid sequence of that protein is not known. Isolating a gene from a cDNA library is made much easier when at least a partial amino acid sequence is known, and is further facilitated when a complete coding sequence from at least one species is known. Procedures for the preparation of cDNA sequences in plasmid libraries derived from the reverse transcription of mRNA are well-known to the art.

The polymerase chain reaction (PCR) provides a powerful alternative to cDNA cloning for the amplification of sequences encoding a selected protein when at least a partial sequence of the selected protein is known. A degenerate oligonucleotide sequence is prepared according to the complement of the sequence encoding the partial amino acid sequence, and this degenerate oligonucleotide (i.e., a family of sequences) is used to prime PCR synthesis using cDNA derived from polyadenylated RNA as template. Further oligonucleotides for priming PCR are derived from unique (i.e., known) nucleotide sequences.

Expression refers to the transcription and translation of a structural gene (coding sequence) so that a protein (i.e., expression product) having the biological activity of GlcNAc T-V is synthesized. It is understood that post-translational modification(s) may remove portions of the polypeptide which are not essential to enzymatic activity and that glycosylation processes may also occur.

The term expression control sequences refer to DNA sequences that control and regulate the transcription and translation of another DNA sequence (i.e., a coding sequence). A coding sequence is operatively linked to an expression control sequence when the expression control sequence controls and regulates the transcription and translation of that coding sequence. Expression control sequences include, but are not limited to, promoters, enhancers, promoter-associated regulatory sequences, transcription termination and polyadenylation sequences, and their positioning and use is well understood by the ordinary skilled artisan. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene. The combination of the expression control sequences and the GlcNAc T-V coding sequences form the GlcNAc T-V expression cassette.

As used herein, an exogenous nucleotide sequence is one which is not in nature covalently linked to a particular nucleotide sequence, e.g., a GlcNAc T-V coding sequence. Examples of exogenous nucleotide sequences include, but are not limited to, plasmid vector sequences, expression control sequences not naturally associated with particular GlcNAc T-V coding sequences, and viral vector sequences. A non-naturally occurring DNA molecule is one which does not occur in nature, and it is thus distinguished from a chromosome, for example. As used herein, a non-naturally occurring DNA molecule comprising a sequence encoding an expression product with GlcNAc T-V activity is one which comprises said coding sequence and sequences which are not associated therewith in nature.

Similarly, as used herein an exogenous gene is one which does not naturally occur in a particular recombinant host cell but has been introduced in using genetic engineering techniques well known in the art. An exogenous gene as used herein can comprise a GlcNAc T-V coding sequence expressed under the control of an expression control sequence not associated in nature with said coding sequence.

Another feature of this invention is the expression of the sequences encoding GlcNAc T-V. As is well-known in the art, DNA sequences may be expressed by operatively linking them to an expression control sequence in an appropriate expression vector and employing that expression vector to transform an appropriate host cell.

A wide variety of host/expression vector combinations may be employed in expressing the DNA sequences of this invention. Useful expression vectors, for example, may consist of segments of chromosomal, nonchromosomal and synthetic DNA sequences. Suitable vectors include derivatives of SV40 and known bacterial plasmids, e.g., *Escherichia coli* plasmids colE1, pCR1, pBR322, pMB9 and their derivatives, plasmids such as RP4; phage DNAs, e.g., M13 derivatives, the numerous derivatives of phage λ, e.g., λgt11, and other phage DNA; yeast plasmids derived from the 2 μ circle; vectors useful in eukaryotic cells, such as insect or mammalian cells; vectors derived from combinations of plasmids and phage DNAs, such as plasmids that have been modified to employ phage DNA or other expression control sequences; baculovirus derivatives; and the like. For mammalian cells there are a number of well-known expression vectors available to the art.

Any of a wide variety of expression control sequences may be used in these vectors to express the DNA sequences of this invention. Such useful expression control sequences include, for example, the early and late promotes of SV40 or adenovirus for expression in mammalian cells, the lac system, the trp system, the TAC or TRC system, the major operator and promoter regions of phage λ, the control regions of fd coat protein, the promoter for 3-phosphoglycerate kinase of phosphatase (e.g., pho5), the promoters of the yeast α-mating factors, and other sequences know to control the expression of genes of prokaryotic or eukaryotic cells or their viruses, and various combinations thereof. The skilled artisan understands which expression control sequences are appropriate to particular vectors and host cells.

A wide variety of unicellular host cells are also useful in expressing the DNA sequences of this invention. These hosts may include well-known eukaryotic and prokaryotic hosts, such as strains of *E. coli*, Pseudomonas, Bacillus, Streptomyces, fungi such as yeasts, and animal cells, such as Chinese Hamster Ovary (CHO), R1.1, B-W and L-M cells, African Green Monkey kidney cells (e.g., COS 1, COS-7, BSC1, BSC40, and BMT10), insect cells (e.g., Sf9), and human cells and plant cells in culture.

It is understood that not all combinations of vector, expression control sequence and host cell will function equally well to express the DNA sequences of this invention. However, one skilled in the art will be able to select the proper vector, expression control sequence, and host cell combination without undue experimentation to accomplish the desired expression without departing from the scope of this invention.

In selecting a suitable expression control sequence, a variety of factors will normally be considered. These include, for example, the relative strength of the promoter, its controllability, and its compatibility with the particular DNA sequence or gene to be expressed, e.g., with regard to potential secondary structure. Suitable unicellular hosts will be selected by consideration of factors including compatibility with the chosen vector, secretion characteristics, ability to fold proteins correctly, and fermentation requirements, as well as any toxicity to the host of the product encoded by the DNA sequences to be expressed, and the ease of purification of the expression products. The practitioner will be able to select the appropriate host cells and expression mechanisms for a particular purpose.

Several strategies are available for the isolation and purification of recombinant GlcNAc T-V after expression in a host system. One method involves expressing the proteins in bacterial cells, lysing the cells, and purifying the protein by conventional means. Alternatively, one can engineer the DNA sequences for secretion from cells. See Example 11 and/or Colley et al. (1989) *J. Biol. Chem.* 264:17619–17622, and U.S. Pat. No. 5,032,519, issued Jul. 16, 1991, which references describe purifying a sialyltransferase by engineering the cleavable signal peptide of human gamma-interferon onto the DNA sequence for the transferase. Larsen et al. (1990) *Proc. Natl. Acad. Sci. USA* 87:6674–6678, fused the DNA sequence for protein A to the amino-terminal end of a fucosyl transferase gene and expressed it as an excreted fusion protein. In these constructions, one can optionally remove the transmembrane region of these proteins that exists near the amino-terminus. After secretion the proteins are purified from the medium. Similar strategies are available for bacterial expression systems.

N-acetylglucosaminyltransferase V (GlcNAc T-V) denotes the enzyme UDP-N-acetylglucosamine: α-6-D-mannoside β(1,6)-N-acetylglucosaminyltransferase (EC 2.4.1.155). This enzyme is responsible for the synthesis of β1,6 branch structure (-[GlcNAc-β-(1,6)Man-α(1,6)Man]-) found in both tri- and tetraantennary N-linked oligosaccharides.

It is understood by those skilled in the art that the exemplified rat GlcNAc T-V coding sequence, provided herein in FIG. 10 and in SEQ ID NO:15 from nucleotide 299 through nucleotide 2521, is representative of GlcNAc T-V from other vertebrate sources, especially of other mammalian sources, including humans. SEQ ID NO:17 and SEQ ID NO:19 provide the CHO and human sequences, respectively, encoding GlcNAc T-V, and SEQ ID NO:21 provides a partial mouse sequence encoding GlcNAc T-V. The coding sequences for GlcNAc T-V provided herein are suitable for use in preparing or deriving PCR primers for identifying and/or amplifying sequences encoding human or other animal GlcNAc T-V, and/or for use as hybridization probes to identify clones encoding human, hamster, rat, other mammalian or other vertebrate GlcNAc T-V in appropriate genomic or cDNA libraries.

The techniques for the purification of the rat kidney GlcNAc T-V disclosed herein will be understood to be applicable to the purification of human or other GlcNAc T-V to a level comparable to that of rat kidney GlcNAc T-V. The skilled artisan recognizes that routine modifications of the procedures disclosed herein may provide improved results in isolating nonexemplified GlcNAc T-V enzymes.

Species other than rat, mouse, hamster and human contain genes encoding proteins which catalyze the same enzymatic reaction as rat GlcNAc T-V, which genes have significant sequence homology to the rat, hamster, mouse and human sequences encoding GlcNAc T-V. One can isolate these homologous cDNAs and/or genes using the DNA sequences of this invention as probes or primers under standard hybridization conditions. This invention specifically contemplates and encompasses such sequences.

A comparison of the human, CHO, rat and partial mouse GlcNAc T-V nucleotide sequences is presented in FIGS. 11A–11F (SEQ ID NOS:19, 17, 15 and 21, respectively). The coding region of SEQ ID NO:15 extends from an ATG starting at nucleotide 299 to a stop codon ending at nucleotide 2524. The rat sequence contains 298 bp of upstream 5' untranslated sequence. The human and the CHO sequences contain 136 bp and 243 bp of 5' untranslated sequence respectively. The partial mouse sequence is presented starting within the coding region at the nucleotide numbered 1159 of SEQ ID NO:15. In addition, approximately 300 bp of the human, 100 bp of the rat and 325 bp of the mouse 3' untranslated regions are provided. Analysis of the coding regions of these sequences indicates that there is approximately 89% homology of the human sequence compared with the rat sequence. The CHO sequence shares an approximately 93% homology with the rat sequence. In a comparison of the partial mouse coding region with the corresponding portion of the rat sequence, approximately 96% nucleotide sequence homology is obtained.

In FIGS. 12A–12B the human (SEQ ID NO:20), CHO (SEQ ID NO:18), rat (SEQ ID NO:16) and partial mouse (SEQ ID NO:22) GlcNAc T-V deduced amino acid sequences are compared. The partial mouse sequence is presented starting at amino acid 288 of SEQ ID NO:16. The human GlcNAc T-V sequence contains an additional valine at amino acid 109 compared to the rat and CHO sequences. The available mouse sequence does not extend to this region. The additional amino acid in the human sequence occurs at the site of the first potential N-linked glycosylation site, although the potential glycosylation sequence is maintained. The human, CHO and rat sequences all contain the same six potential N-glycosylation sites. The mouse sequence also shares the three potential N-glycosylation sites that are located within the available GlcNAc T-V sequence. There is approximately 98% amino acid sequence identity between human and rat amino acid sequences. The CHO amino acid sequence is approximately 99% identical with the rat, and the mouse amino acid sequence is greater than 99% identical with the rat over the region for which the mouse sequence was obtained.

Thus, GlcNAc T-V coding sequences from vertebrate sources have significant sequence homology to the exemplified rat, human and hamster GlcNAc T-V coding sequences and the encoded GlcNAc T-V enzymes have a high degree of amino acid sequence identity as disclosed herein. It is obvious to one normally skilled in the art that human, rat and CHO GlcNAc T-V cDNA clones, genomic clones and PCR ampliners can be readily isolated using standard procedures and the sequence information provided herein. There would be no need to practice these examples exactly, but rather the sequence information provided herein (SEQ ID NOs 15–22) enables the isolation of rat, CHO, mouse, human and other GlcNAc T-V nucleic acid coding sequences and amino acid sequences. It is further obvious to one normally skilled in the art that, as demonstrated in Examples 12 and 13, GlcNAc T-V cDNA and genomic clones, cDNA and genomic gene sequences, and amino acid sequences can be readily obtained and used for GlcNAc T-V from any mammalian species using standard procedures and the sequence information provided herein. The ordinary skilled artisan can utilize the exemplified sequences provided herein, or portions thereof, preferably at least 25–30 bases in length, in hybridization probes to identify cDNA (or genomic) clones encoding GlcNAc T-V, where there is at least 70% sequence homology to the probe sequence using appropriate art-known hybridization techniques. The skilled artisan understands that the capacity of a cloned cDNA to encode functional GlcNAc T-V enzyme can be readily tested as taught herein (See Example 11).

Hybridization conditions appropriate for detecting various extents of nucleotide sequence homology between probe and target sequences and theoretical and practical consideration are given, for example in B. D. Hames and S. J. Higgins (1985) *Nucleic Acid Hybridization*, IRL Press, Oxford, and in Sambrook et al. (1989) supra. Under particular hybridization conditions the DNA sequences of this invention will hybridize to other DNA sequences having sufficient homology, including homologous sequences from different species. It is understood in the art that the stringency of hybridization conditions is a factor in the degree of homology required for hybridization. The skilled artisan knows how to manipulate the hybridization conditions so that the stringency of hybridization is at the desired level (high, medium, low). If attempts to identify and isolate the GlcNAc T-V gene from another mammalian source fail using high stringency conditions, the skilled artisan will understand how to decrease the stringency of the hybridization conditions so that a sequence with a lower degree of sequence homology will hybridize to the sequence used as a probe. The choice of the length and sequence of the probe is readily understood by the skilled artisan.

When a cDNA library is used as a source of GlcNAc T-V coding sequences, the skilled artisan will take steps to insure that the library is of high quality, i.e., that rare mRNAs will be represented and that large mRNAs (larger than about 3 kb) will be present as full length cDNA clones. If the artisan uses one of the commercially available or otherwise accessible cDNA libraries, he will choose one that meets the criteria taught herein. Providing for rare and/or large message representation is within the skill of the art.

The DNA sequences of this invention refer to DNA sequences prepared or isolated using recombinant DNA techniques. These include cDNA sequences, sequences isolated using PCR, DNA sequences isolated from their native genome, and synthetic DNA sequences. As used herein, this term is not intended to encompass naturally-occurring chromosomes or genomes. Sequences derived from the GlcNAc T-V gene can be used in studying the regulation of GlcNAc T-V expression in normal cells, in transformed cells and in metastatic tumor cells, and can be used in designing mechanisms, e.g., via antisense RNA or DNA, for inhibiting metastasis of tumor cells. These sequences can also be used to direct recombinant synthesis of GlcNAc T-V.

Expression of recombinant DNA molecules according to this invention may involve post-translational modification of a resultant polypeptide by the host cell. For example, in mammalian cells expression might include, among other things, glycosylation, lipidation or phosphorylation of a polypeptide, or proteolytic cleavage of a signal sequence to produce a "mature" protein. Accordingly, as used herein, the term "GlcNAc T-V" encompasses full-length polypeptides and modifications or derivatives thereof, such as glycosylated versions of such polypeptides, mature proteins, polypeptides retaining a signal peptide, truncated polypeptides having comparable biological activity, and the like. Expression of GlcNAc T-V in eukaryotic cell lines expressing biologically active glycoproteins will allow efficient branch structure initiation directed by GlcNAc T-V, where desired.

Rat kidney was the source of the GlcNAc T-V for purification because of the commercial availability of relatively large quantities of the tissue. The purification of rat kidney GlcNAc T-V is described in Shoreibah et al. (1992) supra. A survey of mouse, hamster and rat tissues had revealed that kidney was one of the most abundant sources of the enzyme in these rodents. Purified GlcNAc T-V from rat kidney migrates predominantly as a doublet of 69 and 75 kDa on 10% SDS-polyacrylamide gels. However, addition of EDTA to the buffers throughout the extraction and purification procedure results in isolation of an enzymatically active protein of an apparent molecular weight of about 95 kDa as estimated by SDS-PAGE. It is postulated that EDTA inhibits an endogenous protease in the extracts or in cell-free conditioned culture medium in the case where soluble secreted GlcNAc T-V is produced. Alternatively, a cocktail of protease inhibitors can be used as described in Shoreibah et al. (1992 supras, or preferably, the cocktail of protease inhibitors at a five-fold greater concentration than disclosed therein.

The first step in the exemplified GlcNAc T-V purification was the preparation of an acetone powder from rat kidney. The acetone powder is thrice extracted with Triton X-100, resulting in the solubilization of over 95% of the activity from the acetone powder. Chromatography over UDP-hexanolamine-SEPHAROSE results in 145-fold purification. Inclusion of EDTA in the column buffer prevents galactosyltransferase and GlcNAc T-I from binding to the support. The substitution of the SEPHAROSE (Pharmacia, Piscataway, N.J.; agarose) at a level of 14 μmoles of UDP-hexanolamine per ml of settled gel is critical; substitution levels of 6 and 9 μmoles per ml gave essentially no GlcNAc T-V yield.

The next step of the purification was chromatography over a synthetic oligosaccharide inhibitor-BSA-affinity column. The ligand in the column is an active site inhibitor which mimics the natural oligosaccharide acceptor of GlcNAc T-V, but contains a hydrogen in place of the reactive 6'-hydroxyl. Chromatography over this resin and elution of bound material with a step gradient of UDP resulted in an additional 2000-fold purification. The purification of rat kidney GlcNAc T-V is summarized in Table 1. The material resulting from these two chromatographic steps resulted in substantially pure enzyme, having a specific activity of approximately 18 μmol/min·mg protein under the assay conditions disclosed herein. This enzyme preparation is stable in the presence of 20% glycerol for several months when stored at 4° C.

TABLE 1

PURIFICATION OF RAT KIDNEY N-ACETYLGLUCOSAMINYLTRANSFERASE V
Results described below are based on a preparation of the enzyme from 300 g of frozen rat kidneys

| Step | Volume ml | Protein mg | Total Activity nmol/h | Specific Activity nmol/ (mg · h) | Yield % | Purification-fold |
|---|---|---|---|---|---|---|
| Rat kidney acetone powder Triton X-100 extract | 3,300 | 13,900 | 2,221 | 0.16 | 100 | 1 |
| UDP-hexanolamine- | 96 | 38.0 | 889 | 23.2 | 40 | 145 |

TABLE 1-continued

PURIFICATION OF RAT KIDNEY N-ACETYLGLUCOSAMINYLTRANSFERASE V
Results described below are based on a preparation of the enzyme from 300 g
of frozen rat kidneys

| Step | Volume ml | Protein mg | Total Activity nmol/h | Specific Activity nmol/ (mg · h) | Yield % | Purification- fold |
|---|---|---|---|---|---|---|
| Sepharose Inhibitor-BSA- Sepharose | 6 | 0.0078 | 568 | 73,000 | 26 | 450,000 |

To confirm that the two major SDS-PAGE protein bands (69 and 75 kDa) resulting from the two column purification scheme comprised GlcNAc T-V, an aliquot of the purified enzyme preparation was re-chromatographed on a 1 ml UDP-hexanolamine-agarose column. The bound material was eluted using several stepwise elutions of the ligand UDP, instead of the single concentration of NaCl, as used in the first chromatographic step. Almost no activity was detected in either the fractions eluted using a UDP concentration of 10 or 20 mM. Fifty mM UDP displaced the majority of the GlcNAc T-V activity from the column. A small peak was eluted using 50 mM UDP plus 150 mM NaCl. As judged by the silver staining pattern, rechromatography did not result in further increases in purity of the GlcNAc T-V. Similar results were obtained when a sample material resulting from the two column purification scheme were re-chromatographed on the inhibitor-BSA affinity column.

Once the GlcNAc T-V was substantially purified, the assay conditions were optimized. Enzymatic activity was stabilized and enhanced by the inclusion of 20% glycerol and 0.5 mg/ml IgG. The optimal pH range for the substantially pure GlcNAc T-V was 6.5 to 7.0; optimal Triton X-100 concentration was in the range of about 1.0 to about 1.5%. Enzyme activity was maximal at about 0.2 M NaCl, and was inhibited at higher salt concentrations. Divalent cations had a minimal effect on apparent enzyme activity when added as $MnCl_2$, $CaCl_2$ or $MgCl_2$, and the addition of 20 mM EDTA did not appear to be inhibitory.

Using the optimized assay conditions, kinetic parameters were determined for the substantially pure GlcNAc T-V enzyme. The apparent $K_m$ for the oligosaccharide acceptor ($\beta$GlcNAc(1,2) $\alpha$Man(1,6) $\beta$Man-O-$(CH_2)_8COOCH_3$) was 87 $\mu$M, and the apparent $K_m$ for UDP-GlcNAc was 11.0 mM. The apparent $V_{max}$ was 18.8 $\mu$mol/(mg·min).

For amino acid sequence analysis, the enzyme was further purified by preparative SDS-PAGE using an Applied Biosystems High Performance Electrophoresis Apparatus (Applied Biosystems, Foster city, Calif.) which elutes samples from a tube gel and collects fractions. The fractions containing enzyme were pooled and concentrated. The enzyme protein was then precipitated by ethanol addition and lowering the temperature [−20° C.]. The precipitate was collected by centrifugation, washed and dried.

Figure 3:
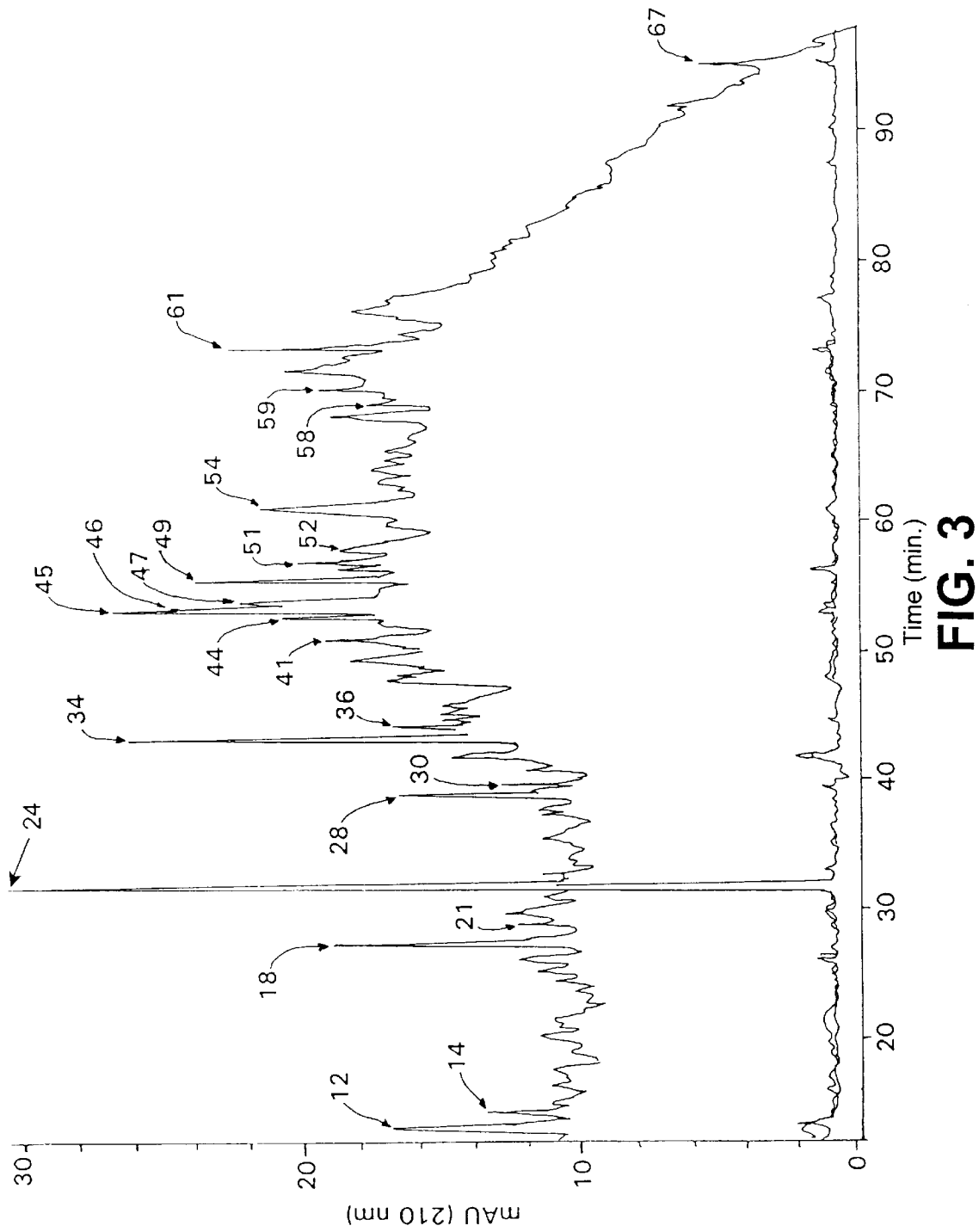
FIG. 3 is a profile of the tryptic peptide digest components resolved by reverse phase HPLC. The vertical axis represents protein content as measured by absorbance at 210 nm and the horizontal axis represents retention time on the column. The peptides of peaks 28, 34, 49 and 61 were selected as candidates for gas phase peptide sequencing.

Initial $NH_2$-terminal amino acid sequencing results indicated that the N-terminus of the protein was blocked. A sample of the substantially purified GlcNAc T-V from rat kidney was then digested using immobilized trypsin, separated from the immobilized trypsin and the peptides within the digest were then separated by reverse phase HPLC using a 2.1×150 mm VYDAC C18 column, eluted with a gradient of acetonitrile. The elution profile is shown in FIG. 3. Four peaks were chosen for gas phase sequencing (FIG. 3, peaks 29, 34, 49, 61). The results were as follows:

Peak #34 AsnThrAspPhePheIleGlyLysProThrLeuArg (SEQ ID NO:1)

Peak #49 AlaIleLeuAsnGlnLysIleGluPro-TyrMetProTyrGluPheThr (SEQ ID NO:2)

Peak #28 ValLeuAspSerPheGlyThrGluProGluPheAsn (SEQ ID NO:3)

Peak #61 SerAspProCysTyrAlaAspTyrGluVal (SEQ ID NO:4)

These amino acid sequences were confirmed by comparison with the deduced amino acid sequence of the rat GlcNAc T-V, and it was deduced that the Glu residue of SEQ ID NO:4 should be Gly. The amino acid sequences obtained from the four peaks were searched within the Swiss Protein Data Bank and deduced degenerate coding sequences were searched in the Genbank database. No significantly homologous sequences were found.

The determination of a partial amino acid sequence for GlcNAc T-V allows the production of sets of degenerate oligonucleotide probes or primers, thus, enabling the cloning of the corresponding cDNA and genomic clones. Those oligonucleotides can also be used to study the transcriptional and/or translational mechanisms which control the level of expression of the gene encoding GlcNAc T-V.

From the amino acid sequences for the internal peptides corresponding to peaks 34 and 49, corresponding degenerate oligonucleotides were designed for use as primers for PCR amplification of cDNA sequences encoding GlcNAc T-V. The degenerate 29 base oligonucleotide designed from the sequence of first ten amino acids of the Peak 34 peptide is presented as Primer 1 (SEQ ID NO:5). The antisense counterpart (SEQ ID NO:6) of Primer 1, termed antiprimer 1 herein, will be useful as a primer in the PCR amplification of sequences encoding GlcNAc T-V present within polyadenylated mRNA populations, prepared from cells including, but not limited to, rat kidney, mouse lymphoma BW5147 cells and ascites-grown rat mammary gland tumor MAT C1 cells.

Primer 1: AAYACIGAYTTYTTYATHGGIAARCCNAC (SEQ ID NO:5)

AntiPrimer 1: GTIGGYTTICCDATRAARAARTCIGTRTT (SEQ ID NO:6) (antisense)

A second degenerate 29 base oligonucleotide was designed using the sequence of the last ten amino acids of the peptide corresponding to Peak 49:

Primer 2: ATHGARCCITAYATGCCITAYGARTTYAC (SEQ ID NO:7)

AntiPrimer 2: TCRTAIGGCATRTAIGGYTCDATYT-TYTG (SEQ ID NO:8) (antisense)

The antisense primers given above can also be used to amplify mRNA encoding GlcNAc T-V in polymerase chain reactions. Other oligonucleotide primers and "antiprimers"

may be designed using the peptide sequences and/or GlcNAc T-V sequences disclosed herein by one of ordinary skill in the art for use in priming PCR synthesis of GlcNAc T-V coding sequences.

The sequences of the antisense primers (AntiPrimers 1 and 2; SEQ ID NO:6 and SEQ ID NO:8) are complementary to those of the corresponding Primers 1 and 2, respectively (SEQ ID NO:5 and SEQ ID NO:7). Either the sense or the antisense primers, or preferably the PCR amplification product of Primer 1 and AntiPrimer 2, can be used as hybridization probes or as PCR primers for screening a rat kidney cDNA library, a rat genomic library or mouse libraries for clones encoding GlcNAc T-V. The primers and antisense primers in appropriate combination can be used to prime PCR reactions using cDNA prepared, for example, from rat kidney cell poly(A)+ RNA. Sequences amplifiable with these primers and antisense primers in PCR reactions will be those encoding portions of GlcNAc T-V.

Figure 4:
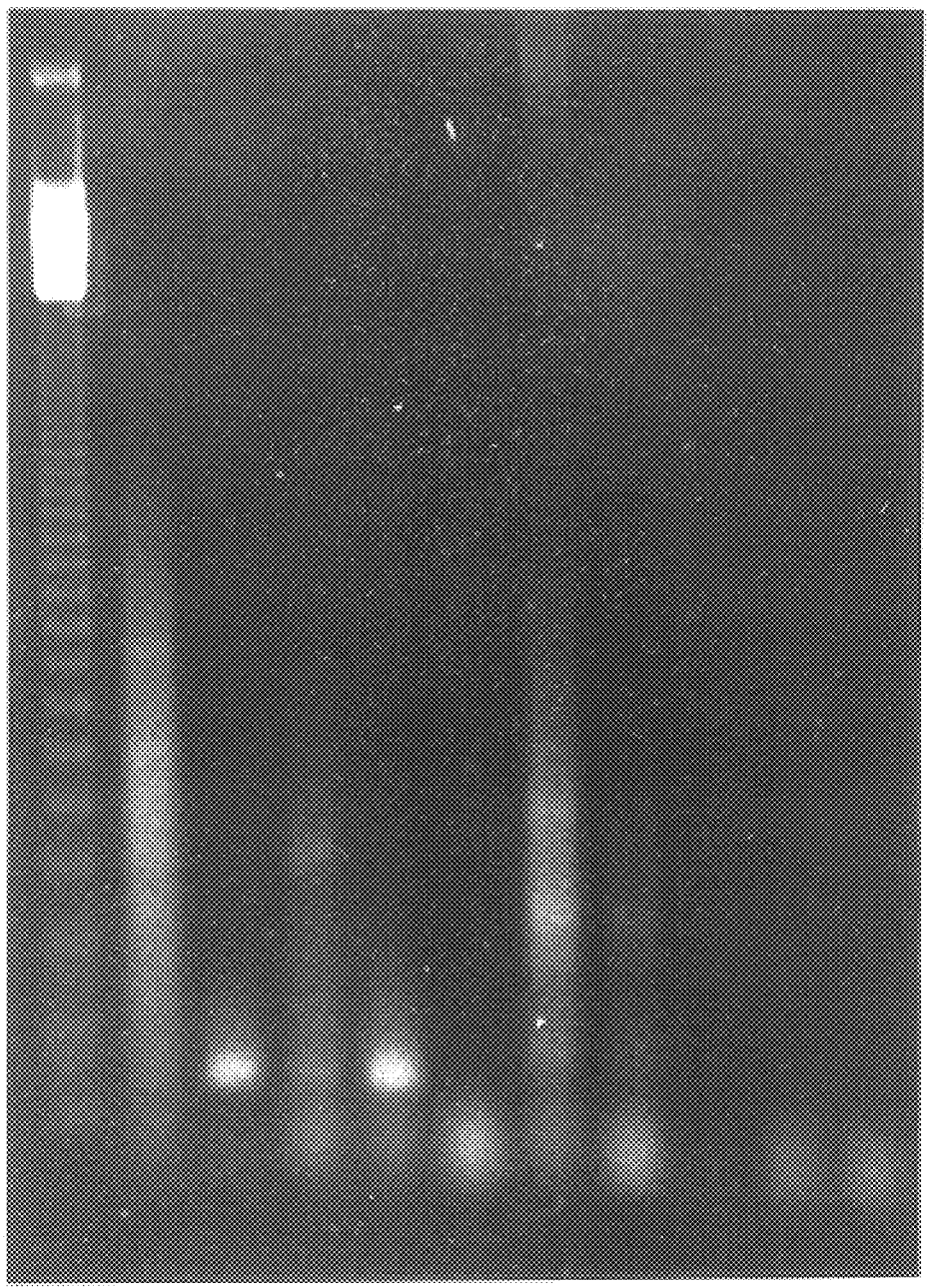
FIG. 4 is a reproduction of an ethidium bromide-stained agarose gel, showing the reaction products of the results of PCR amplification of GlcNAc T-V coding sequences. Lane 1 contains molecular weight standards (123 ladder); Lanes 2 and 7 were the results of reactions containing mouse lymphoma cell line BW5147 cDNA from total RNA as a template; Lanes 3 and 8 were the results of reactions containing mouse lymphoma cell line BW5147 cDNA from poly(A)+ RNA as template; Lanes 4 and 9 were the results of reactions containing rat mammary tumor cell line MAT C1 cDNA from total RNA as template; Lanes 5 and 10 were the results of reactions containing rat mammary tumor cell line MAT C1 cDNA from poly(A)+ RNA as template; and Lanes 6 and 11 were the results for reactions without added template. The reactions run in Lanes 2–6 were carried out with Primer 1 (SEQ ID NO:5) and Antiprimer 2 (SEQ ID NO:8) as the primers for PCR. In the reactions run in Lanes 7–11 were carried out with Primer 2 (SEQ ID NO:7) and Antiprimer 1 (SEQ ID NO:6).
Figure 5A:
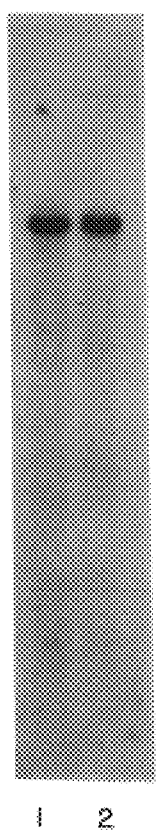
FIG. 5A shows the results for BglII-digestion, FIG. 5B the results for NcoI/XhaI digestion, FIG. 5C for NcoI digestion and FIG. 5D for BamHI/BglII digestion. In each panel, lane 1 contains digested MAT C1 genomic DNA and lane 2 contains digested rat liver genomic DNA.
Figure 5B:
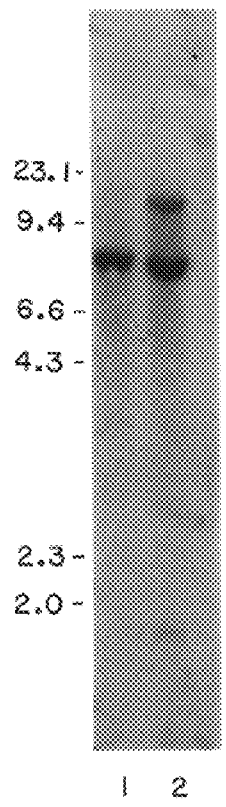
FIG. 5 illustrates autoradiograms resulting from Southern hybridizations using radiolabelled 200 amplimer (PCR product) prepared using rat mammary tumor cell line MAT C1 cDNA from poly(A)+ RNA as template and Primer 1 (SEQ ID NO:5) and Antiprimer 2 (SEQ ID NO:8) as primers.
Figure 5C:
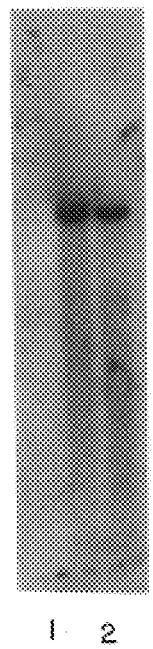
Figure 5D:
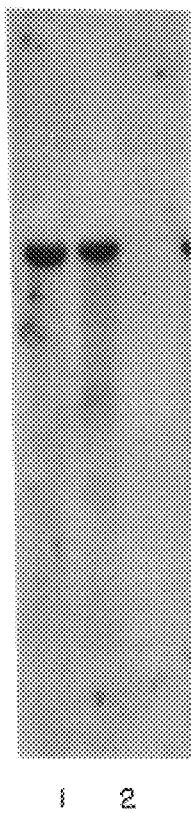

For PCR amplification of sequences encoding GlcNAc T-V, Primer 1 and AntiPrimer 2 cDNA were used to prime PCR-directed DNA synthesis. The combination of Primer 2 (SEQ ID NO:7) and AntiPrimer 1 (SEQ ID NO:6) did not yield an amplification product from either cell line. Using cDNA prepared from poly(A)+ RNA from either the rat mammary tumor line MAT C1 or from the mouse lymphoma cell line BW5147 with Primer 1 and AntiPrimer 2, an amplification product of about 200 bp was obtained, as shown in FIG. 4. These results indicate that the peak 34 sequence (SEQ ID NO:1) is located about 60 amino acids toward the amino end of the protein as compared with the peak 49 amino acid sequence. Background signal was reduced substantially by using 55° C. rather than 50° C. as the annealing temperature in the PCR reactions. The results also indicate a high degree of homology between the GlcNAc T-V coding sequences in mouse and rat. Thus, the primer/antiprimer sequences disclosed herein will be useful in identifying GlcNAc T-V genes and coding sequences of mammals other than rat.

The amplimer made by PCR with cDNA from MAT C1 poly(A)+ RNA as template and Primer 1 (SEQ ID NO:5) and AntiPrimer 2 (SEQ ID NO:8) was $^{32}$P-labelled for use as a hybridization probe. Rat MAT C1 genomic DNA and rat liver genomic DNA were digested in separate restriction endonuclease reactions, the fragments were separated in parallel using agarose gel electrophoresis, blotted to support and DNA-DNA hybridization was carried out under standard hybridization conditions of low stringency. Hybridization patterns were consistent with a single genetic locus encoding GlcNAc T-V in each. FIG. 5 illustrates the autoradiogram obtained for Southern hybridization with rat mammary tumor cell line MAT C1 and for rat liver genomic DNA. With BglII, BamHI/BglII and NcoI digestion, the size of the unique hybridizing genomic band is between 2 and 10 kbp. With NcoI/XhaI digestion, the size of the hybridizing band is between roughly 6 and 9 kb. Routine experimentation will allow size estimation with more precision. The 200 bp amplimer used in this experiment can be used to screen cDNA or genomic libraries to identify GlcNAc T-V sequences. Standard "walking" experiments can be performed to obtain the sequences which flank the hybridizing fragment(s) after cloning of that fragment so that the entire gene can be isolated.

Labelled oligonucleotides having sequences of Primers 1 and 2 (SEQ ID NO: 5 and 7) or AntiPrimers 1 and 2 (SEQ ID NO:6 and SEQ ID NO:8), or preferably the PCR amplification product (amplimer) made using Primer 1 and AntiPrimer 2 as primers, can be successfully used as hybridization probes for screening cDNA libraries prepared from sources including mouse lymphoma BW5147 cells, mouse 3T3 cells and ascites-grown rat mammary gland MAT-C1 cells for sequences encoding GlcNAc T-V.

Figure 6:
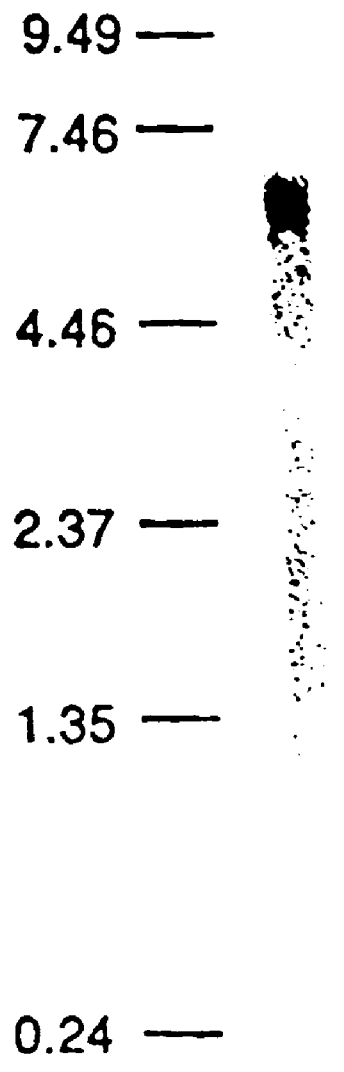

When a restriction fragment from within the coding region of a partial mouse cDNA clone was used as a hybridization probe in a Northern blot of rat kidney mRNA, a band of about 7 kb, along with apparent degradation products, was displayed (See FIG. 6). Thus, the size of the GlcNAc T-V MRNA is large, and care must be taken in preparing (or in choosing) a cDNA library from which to isolate a full length GlcNAc T-V coding sequence.

Examples 7–9 describe the steps in the successful identification and cloning of the rat GlcNAc T-V coding sequence using a PCR-cDNA strategy. In other experiments, an amplimer of about 170–200 bases was prepared by PCR. This amplimer was used to screen a mouse cDNA library, and a partial clone of about 1.7 kb was isolated. Sequence analysis revealed that the long open reading frame did not contain a start codon, and about 300 amino acids were determined by the open reading frame. A series of PCR amplification and screening steps were carried out using plasmid DNA prepared from pools of cDNA clones from subsets of a cDNA library prepared from Rat 1-EJ cell mRNA.

A rat cDNA clone of about 4.8 kb, carrying the full length GlcNAc T-V coding sequence was isolated. A portion of the cDNA was sequenced; that DNA sequence is presented in FIG. 10A–10E and in SEQ ID NO:15. The coding sequence extends from an ATG start codon beginning at nucleotide 299 through a stop codon ending at nucleotide 2521.

The deduced rat GlcNAc T-V amino acid sequence is given in FIG. 12A–12B and in SEQ ID NO:16. The predicted molecular weight of the encoded GlcNAc T-V, 84,561, is larger than the protein bands observed in and isolated from SDS-PAGE gels. A recent experiment has demonstrated that when GlcNAc T-V is purified from rat kidney by in the presence of a cocktail of protease inhibitors in vast excess, a band of about 95 kDa, in addition to the 69 and 75 kDa bands, is observed. When a radioactive photoaffinity active site label was used to tag active enzyme, all three bands were labelled. These observations suggest that the 75 and 69 kDa bands represent proteolytic fragments of the larger protein. The 95 kDa band is likely to represent a glycosylated form of the polypeptide encoded in SEQ ID NO:15. Six potential sites for N-linked glycosylation were identified: Asn residues at amino acid positions 109, 114, 117, 333, 432 and 446 in SEQ ID NO:16. A putative transmembrane domain, extending from amino acids 14–30, was identified by hydrophobicity analysis using Kyte and Doolittle methodology. This proposed transmembrane domain is characteristic of type II membrane proteins, and is similar to other enzymes of the lumen of the Golgi apparatus.

Within the deduced amino acid sequence of rat GlcNAc T-V (SEQ ID NO:16), the sequences corresponding to the Peak #s 34, 49 and 28 peptide sequences (SEQ ID NOs:1–3) were at amino acids 546–557, 592–607 and 375–386, respectively. The amino acid sequence of Peak #61 (SEQ ID NO:4) occurs at amino acids 168–177 in SEQ ID NO:16. The identities of the cysteine and aspartate residues are confirmed, and the amino acid at the ninth position in SEQ ID NO:4 was deduced to be glycine rather than glutamate, based on the nucleotide sequence in SEQ ID NO:15.

It is well-known in the biological arts that certain amino acid substitutions can be made within a protein without affecting the functioning of that protein. Preferably such substitutions are of amino acids similar in size and/or charge properties. For example, Dayhoff et al. (1978) in *Atlas of Protein Sequence and Structure*, Volume 5, Supplement 3, Chapter 22, pages 345–352, which is incorporated by reference herein, provides frequency tables for amino acid substitutions which can be employed as a measure of amino acid similarity. Dayhoff et al.'s frequency tables are based on comparisons of amino acid sequences for proteins having the same function from a variety of evolutionarily different sources.

The 4.8 kb rat cDNA insert determined by partial DNA sequence analysis to contain an apparently full length GlcNAc T-V coding sequence was subcloned into the pJT-2 expression vector and electroporated into COS-7 cells (See Example 11). After 3 or 4 days incubation after the electroporation, the transfected cells were harvested, frozen and subsequently assayed for GlcNAc T-V activity. Parallel preparations of cells transfected with pJT-2 without insert DNA served as controls. It was estimated that about 3% of the cells were effectively electroporated. From the data in Table 2, it is clear that the cloned rat cDNA fragment encodes a functional GlcNAc T-V enzyme.

TABLE 2

GlcNAc T-V Activity in the Transient Expression Assay

| Sample | Hrs incubation after electroporation | Specific activity (pmol/mg*hr) |
| --- | --- | --- |
| COS-7 (pJT-2) | 68 | 38 |
|  | 92 | 65 |
| COS-7 (pJT-2-TV) | 68 | 624 |
|  | 92 | 499 |

It will be a matter of routine experimentation for the ordinary skilled artisan to use the DNA sequence information presented herein to optimize GlcNAc T-V expression in a particular expression vector and cell line for a desired purpose. A cell line genetically engineered to contain and express a GlcNAc T-V coding sequence will be useful for the recombinant expression of protein products with the characteristic glycosylation dependent on GlcNAc T-V modification of glycoproteins. Any means known to the art can be used to introduce an expressible GlcNAc T-V coding sequence into a cell to produce a recombinant host cell, i.e., to genetically engineer such a recombinant host cell. Recombinant host cell lines which express high levels of GlcNAc T-V will be useful as sources for the purification of GlcNAc T-V, e.g., for studies of inhibitors of GlcNAc T-V activity for preventing or slowing metastasis of tumors. The coding sequence of GlcNAc T-V will be useful in preparing an antisense construct specific for GlcNAc T-V for inhibiting GlcNAc T-V expression where that is desired, for example, in metastasizing tumor cells.

Soluble secreted GlcNAc T-V enzyme proteins can be produced using the disclosure provided herein. A soluble GlcNA T-V is one which lacks the sequences in the amino terminal region of the protein which localize it to and bind it within the cell membrane, particularly within the Golgi apparatus. When the coding region of the enzymatically active portion of GlcNAc T-V, but not including the transmembrane region, is fused downstream of and in frame with a signal sequence coding sequence, and operably linked to transcriptional control sequences, and expressed in a suitable host cell, such as a mammalian cell, soluble GlcNAc T-V is expressed and secreted into the culture medium after the signal peptide portion is removed by specific protease cleavage. As specifically exemplified herein, a soluble, secreted GlcNAc T-V was engineered from the rat cDNA clone encoding GlcNAc T-V as described in U.S. Pat. 5,032,519 (Paulson et al., issued Jul. 16, 1991) with removal of the N-terminal 69 amino acids of rat GlcNAc T-V (see Example 14 for description of cloning). The DNA encoding the remainder of GlcNAc T-V was fused to the human gamma-interferon signal sequence coding region, and there is a Gln residue derived from the gamma-interferon at the N-terminus of the soluble GlcNAc T-V. The ordinary skilled artisan can readily produce soluble GlcNAc T-V derivations using the sequences provided herein, taken with what is well known to the art. Spent medium from cells expressing the soluble rat GlcNAc T-V was chromatographed over a copper chelating column and over CM fast flow Sepharose to yield purified soluble GlcNAc T-V. Table 3 summarizes the results of soluble GlcNAc T-V purification as described in Example 15 herein. It was determined that there were protein bands of 95, 75 and 60 kDa which appeared to have enzymatic activity, although the 60 kDa band appeared to be less active. When EDTA (5 mM) is incorporated in the CM Sepharose column step, nearly all the protein is of about 95 kDa. Alternatively, a cocktail of protease inhibitors for maximizing the amount of 95 kDa protein can be added to the culture medium, removed for the copper chelation column, and provided again before the CM Sepharose cation exchange chromatography step. When no EDTA is used in the second column purification step, the predominant protein band revealed by SDS-PAGE is about 60 kDa, with minor bands at around 75 and 95 kDa. The N-terminal amino acid sequence analysis of the 60 kDa protein (purified by FPLC, gel filtration) is consistent with proteolytic cleavage between amino acids 283 and 284 of SEQ ID NO:16.

TABLE 3

Purification of Soluble GNT-V

| Step | Protein (mg) | Activity (nmole/min) | Specific act. (µmole/min/mg) | Yield (%) | Fold |
| --- | --- | --- | --- | --- | --- |
| Crude media | 37.92 | 793.4 | 20.9 | 100 | 1 |
| Copper chelating | 7.77 | 723.1 | 93.1 | 91 | 4.5 |
| CM Sepharose | 1.20 | 531.3 | 427.8 | 67 | 20.5 |

The $K_m$ of the soluble GlcNAc T-V (95 kDa) for the UDP-GlcNAc and acceptor appear to be 20 mM and 1 mM, respectively, and the calculated $V_{MAX}$ is 453 nmol/min/mg protein.

Gu et al., *J. Biochem.* (1993) 113:614–619, reported that GlcNAc T-V purified from the QC human lung cancer cell line exhibited a molecular weight of 73 kDa with an additional component of 60 kDa when SDS-PAGE was carried out under reducing conditions, and suggested that the 60 kDa component was a proteolytic product of the 73 kDa protein.

The following examples are provided for illustrative purposes as well as for enablement. These examples are not intended to limit the scope of the invention. The examples use many techniques well known and accessible to those skilled in the arts of molecular biology and biochemistry. It will be readily apparent to the skilled artisan that modifications of the methods disclosed herein may be made, and that there will be DNA sequence modifications which can be made with the maintenance of the desired result. It will be readily apparent to one of ordinary skill in the art that the nucleotide sequences and amino acid sequences disclosed herein make it unnecessary to repeat many of the examples to practice the invention. All references cited in this application are expressly incorporated by reference herein.

EXAMPLES

Example 1
Preparation of UDP-Hexanolamine-Agarose

UDP-hexanolamine was prepared and linked to CNBr-activated SEPHAROSE 4B according to the procedure in Barker et al. (1972) *J. Biol. Chem.* 247:7135–7147.

Example 2
Purification of GlcNAc T-V from Rat Kidney

Frozen rat kidneys were purchased from Pel-Freez Biological, Inc. (Rogers, Ark.).

300 g of frozen rat kidneys were homogenized in 3 liters of cold acetone in a Waring blender at 4° C. All subsequent steps were also performed at 4° C. unless otherwise noted. The acetone-insoluble material was collected on Whatman filter paper no. 4. The acetone insoluble material was re-homogenized in acetone and refiltered. The resulting powder was stirred in 1.8 liters Buffer A (0.1 M sodium acetate (pH 6.0), 0.2 M NaCl, 0.01 M EDTA) for 30 min. The residue was collected by centrifugation for 15 min at 7100×g. The pellet was again extracted with Buffer A and centrifuged again.

The resulting pellet was then stirred in 2 liters water and collected by centrifugation. To the washed residue was then added the following protease inhibitors: 0.1 mM PMSF, 0.05 mg/ml aprotonin, 0.5 mg/ml soybean trypsin inhibitor, 0.5 μg/ml leupeptin, and 1 μg/ml pepstatin. This mixture was then homogenized in 1 liter Buffer B (0.01 M Tris-HCl (pH 7.8), 0.4 M KCl,.

The resulting homogenate was brought to 1% Triton X-100 (w/v) and stirred 30 min. The suspension was centrifuged for 20 min at 7100×g to give the first extract (the supernatant). The pellet was twice again homogenized, solubilized with Triton X-100, and clarified by centrifugation to yield the second and third extracts.

The three extracts were pooled and dialyzed against 20 liters Buffer C (50 mM MES pH 6.5, 0.2% (w/v) Triton X-100, 5 mM EDTA, 0.05% sodium azide, over a 72 hr period with a single change of dialysis buffer. The resulting dialysate was clarified by centrifugation and then assayed for protein concentration and enzymatic activity.

In the first affinity chromatography step, 3 l of acetone powder Triton extract was applied to a 1.2×7 cm column of UDP-hexanolamine Sepharose pre-equilibrated with Buffer C. The column was then washed with about 400 ml Buffer C. The column was then eluted with Buffer C plus 0.5 M NaCl. Fractions were collected and assayed for GlcNAc T-V activity.

Pooled fractions (about 100 ml) eluted from the UDP-hexanolamine SEPHAROSE column were dialyzed against Buffer C. The dialyzate was brought to 1 mM UDP-GlcNAc and 20% glycerol and was loaded on a 1.2×3 cm column of inhibitor-BSA-Sepharose pre-equilibrated with Buffer D (50 mM MES pH 6.5, 0.1% Triton X-100, 20% glycerol, 0.05% sodium azide,. The column was then washed with 20 ml Buffer D without UDP-GlcNAc. Finally the column was stopped, brought to room temperature, and then eluted with the inclusion of 500 mM NaCl in Buffer D in which the pH had been adjusted to 8.0. Fractions were collected and assayed for GlcNAc T-V activity.

An aliquot (0.1 ml) of the pooled active fractions from the inhibitor-BSA affinity column was then dialyzed against Buffer C and applied to a 0.4×8 cm column of UDP-hexanolamine Sepharose pre-equilibrated with Buffer D. The column was then eluted with buffers comprising increasing amounts of UDP in Buffer D: 10 mM UDP, 20 mM UDP, 50 mM UDP, 50 mM UDP with 120 mM NaCl and finally 100 mM UDP with 150 mM NaCl. Fractions were collected and assayed for GlcNAc T-V activity. (For this purification step either Buffer D can be used or 50 mM sodium cacodylate pH 6.5, 0.1% Triton X-100, 20% glycerol, 0.05% sodium azide can be used, with incremental increases in NaCl concentration for elution as described for Buffer D.)

Equal volumes from each set of fractions were concentrated under reduced pressure and elevated temperature with a Speed Vac. SDS-polyacrylamide gel electrophoresis of various fractions was carried out on 10% SDS-polyacrylamide gels after the concentrated samples were boiled in 1×gel sample buffer to reduce and denature the proteins (Laemmli (1970) *Nature* 227:680–685). The gels were silver-stained as described in Morrisey (1981) *Anal. Biochem.* 117:307–310 in order to visualize the material.

Example 3
Assay of GlcNAc T-V Activity

A typical radiochemical assay for determining activity during purification contained the following reagents which were dried in vacuo in a 1.5 ml conical centrifuge tube: 2 mM ADP (pyrophosphatase inhibitor, 2.5 mM Bmethyl-GlcNAc (β-hexosaminidase inhibitor), $10^6$ cpm UDP-[6-$^3$H]-GlcNAc (10 cpm/pmol) and 1 mM of the synthetic acceptor (β-D-GlcNAc)-(1,2)-α-D-Man-(1,6)-β-D-Man-O-$(CH_2)_8CO_2Me$ in a total volume of 10 microliters.

To initiate the reaction, 0.01 ml of sample, in a buffer containing 50 mM MES pH 6.0, 0.1% Surfact-Amps (Triton) X-100 (Pierce, Rockford, Ill.), was added to the dried reagents and incubated at 37° C. for several hrs.

To terminate the assay, 0.5 ml water was added to each tube, vortexed thoroughly, and the contents of the tubes were centrifuged. The supernatant was then loaded onto a pellicular C18 Sep-Pak column (Millipore, Bedford, Mass.) activated with methanol and pre-equilibrated with water. The columns were washed with 200 ml water to remove water-soluble radioactivity resulting from unreacted substrate and degradation products. The radiolabeled product of the GlcNAc T-V reaction was then eluted with a 0–100% step gradient of methanol, and radioactivity was quantitated by liquid scintillation counting. All assays were conducted in duplicate, and the results were averaged. In tabulating the results for Table I, assays were done in at least two separate experiments and averaged. The variation between the values derived from duplicates or from separate experiments did not exceed ±10% and typically were less than ±2% of the averaged values.

Radiolabeled product was then separated from the unreacted acceptor and radiolabeled UDP-GlcNAc by virtue of the hydrophobic moiety using C-18 chromatography.

Once the GlcNAc T-V protein was purified, the parameters in the assay were optimized: 20% glycerol, near physiological levels of NaCl (about 200 mM), 0.5 mg/ml IgG, pH about 6.5–7.0, and Triton X-100 concentration about 1.0–1.5%.

GlcNAc T-V protein was measured using the enzyme-linked immunosorbent assay described in Crawely et al. (1990) Analytical Biochem 185:112–117. The ELISA uses unlabeled UDP-GlcNAc and a trisaccharide acceptor (β-D-GlcNAc)-(1,2)-α-D-Man-(1,6)-β-O-Man-D-$(CH_2)_8CO_2Me$ coupled to BSA. This assay relied on the use of a polyclonal antibody specific for the tetrasaccharide-BSA product of the GlcNAc T-V reaction. Due to the extreme sensitivity of the ELISA, column fractions containing an inhibitory amount of NaCl, for example, could be assayed without prior dialysis by simply diluting the samples. Standard calibration curves were generated in each assay and absorbance (or relative activity) was correlated to a specific activity by comparison to values obtained for a sample of known GlcNAc activity, as measured in the radiochemical assay.

Example 4
Measurement of Small Amounts of Protein

The BCA protein assay (Pierce, Rockford, Illinois) was adapted for use in a microtiter plate format using standard polystyrene 96 well plates (Pierce, Rockford, Ill.) to assay column fractions for protein content during purifications. BSA served as the standard protein.

Example 5
Preparation of Inhibitors, Acceptors, Substrates and Affinity Adsorbents UDP hexanolamine was synthesized and linked to CNBr-activated agarose support (SEPHAROSE 4B) as described in Barker et al. (1972) *J. Biol. Chem.* 247:7135–7147. The concentration of the ligand relative to the support was 14 $\mu$moles per ml of settled gel.

The deoxy oligosaccharide inhibitor of GlcNAc T-V activity (n-octyl 6-O-[2-O-(2-acetamido-2-deoxy-$\beta$-D-glucopyranosyl)-6-deoxy-$\alpha$-D-mannopyranosyl]-$\beta$-D-glucopyranoside) was synthesized as described in Palcic et al. (1990) *J. Biol. Chem.* 265:6759–6769, and used in assays.

A similar GlcNAc T-V oligosaccharide inhibitor ($\beta$GlcNAc(1,2) 6-deoxy-$\alpha$-Man(1,6) $\beta$Man-O-(CH$_2$)$_8$COOCH$_3$ was coupled to BSA according to the method of Pinto et al. (1983) *Carbohydr. Res.* 124:313–318 for use as an affinity chromatography ligand. The inhibitor oligosaccharide (4.1 mg) was converted to the acyl azide as a 25 mM solution in DMF (dimethyl formamide) at −15° C. and then 222.2 mg BSA (Sigma Chemical Co., St. Louis, Mo.) was added in 2 ml of 0.35 M KHCO$_3$ and 0.07 M Na$_2$B$_4$O$_7$ (pH 9.0). The resulting solution was held at 4° C. for 24 h, and then extensively dialyzed against distilled water on a Amicon PM-10 ultrafiltration membrane (Amicon, Inc., Division of WR Grace, Danvers, Mass.). The dialysate was then lyophilized, and redissolved. Protein content was measured using the Bradford assay (Bradford (1976) *Analyt. Biochem.* 72:248–254) with BSA as a standard. Carbohydrate content was measured using the phenol-sulfuric acid method (Dubois et al. (1956) *Analyt. Chem.* 28:350–356,. The results indicated that 13 oligosaccharide molecules were incorporated per molecule of BSA (67% coupling).

The coupling of 3.6 mg of the inhibitor-protein complex to 3 ml of periodate-oxidized agarose (SEPHADEX CL-6B, Pharmacia, Piscataway, N.J.) was carried out as described in Stults et al. (1989) *Analyt. Biochem.* 180:114–119 with NH$_2$(CH)$_2$OH-HCl as the final blocking reagent. A coupling of 34% of the oligosaccharide-BSA complex to the agarose gave a final incorporation of 0.07 $\mu$mol of ligand oligosaccharide per ml of settled gel as estimated by the Bradford protein assay.

Trisaccharide oligosaccharide acceptors and their syntheses are described in Palcic et al. (1990) supra; Pierce et al. (1987) *Biochem. Biophys. Res. Commun.* 146:679–684; Arango et al. (1988) *J. Cell. Biochem.* 37:225–231; and Srivastava et al. (1988) *Carbohydr. Res.* 179:137–161.

Example 6
Production of Antibodies specific for GlcNAc T-V

GlcNAc T-V is precipitated from storage buffer by adding 3 volumes of absolute ethanol and left to stand for 30 min at 4° C. The precipitated protein is collected by centrifugation (10,000×G for 10 min), resuspended in 0.3 ml of Buffer D, and mixed with 1.0 ml of Freund's complete adjuvant. The resulting emulsion is administered to two rabbits by injecting intradermally in the back with 50–75 $\mu$l/site or about 75 $\mu$g protein per site. Each rabbit receives booster injections of 150 $\mu$g per dose, prepared in the same way, 14 days after the initial dose, and each rabbit receives 75 $\mu$g at 21, 34, 57 and 64 days after the initial injection. 10–20 ml of blood is collected from an ear vein of each rabbit at weekly intervals, and serum is prepared and stored at −20° C. Relative levels of antibody specific for GlcNAc T-V are estimated by determining the amount of serum required to inhibit 50% of the activity in the assay using the artificial substrate as acceptor. Serum samples with the highest activity are pooled.

Monoclonal antibodies specific for rat kidney GlcNAc T-V are prepared according to standard procedures (e.g., Campbell (1984) *Monoclonal Antibody Technology: Laboratory Techniques in Biochemistry and Molecular Biology* (Burdon and van Knippenberg, eds.) Vol. 13, Elsevier, Amsterdam; Harlow and Lane (1988) *Antibodies: A Laboratory Manual*, Cold Spring Harbor Laboratory, Cold Spring Harbor, N.Y.) after immunization of mice with purified rat kidney GlcNAc T-V.

Example 7
Isolation of PCR Fragment Containing Rat GlcNAc T-V Sequences

A. Rat 1-EJ cDNA Library Construction

The Rat 1-EJ cDNA library had been previously constructed. Messenger RNA was isolated by standard procedures (Maniatis et al., 1982) from Rat 1 cells which had been transfected with the human EJ gene, an activated Harvey ras gene (Peles et al. (1992) *Cell* 69:205–216). Poly (A)+ mRNA was selected using an mRNA separator kit (Clontech Lab, Inc., Palo Alto, Calif.) and cDNA was synthesized with the Superscript kit (BRL Life Technologies, Inc., Bethesda, Md.). Column-fractionated double-stranded cDNA was ligated into SalI and NotI-digested pSPORT-1 plasmid vector (BRL Life Technologies, Inc., Bethesda, Md.) and transformed into *Escherichia coli* DH10B cells by electroporation (Dower et al. (1988) *Nucl. Acids Res.* 16:6127–6145) The SalI site is on the 5' side and the NotI site is on the 3' side of the cDNA sequence of each clone. Transformed *E. coli* DH10B cells were propagated as 43 individual pools and plasmid DNA was isolated from each pool.

B. Design and Construction of Oligonucleotides

The approximately 200 bp PCR amplimer sequences from mouse, rat and human were analyzed, and specific oligonucleotides were designed covering areas where the mouse, rat and human sequences were identical.

Primer A:474-14 GGGCCGATGAAGACTTCTGCG (SEQ ID NO: 9) (antisense)

Primer B:474-16 GGGCTACTTCCTCTCGGTTATTGAG (SEQ ID NO: 10) (antisense)

In addition, an oligonucleotide was designed using the T7 promoter sequence of the cloning vector pSPORT-1.

Primer T7:476-30 GCTCTAATACGACTCACTATAGG (SEQ ID NO: 11) (sense)

C. PCR Amplification of Rat 1-EJ cDNA Library Sequences

An aliquot of plasmid DNA from each pool of the Rat 1-EJ cDNA library was combined to form a Rat 1-EJ cDNA library DNA mixture (Rat 1-EJ cDNA pool). PCR was carried out on the Rat 1-EJ cDNA pool using primers T7:476-30 (SEQ ID NO: 11) and B:474-16 (SEQ ID NO: 10). The T7 sequence of pSPORT-1 lies upstream from the 5' SalI cloning site used in the cDNA synthesis. Therefore, PCR priming using the oligonucleotide T7:476-30 (SEQ ID NO: 11) synthesizes an amplimer covering the extreme 5' end of the cDNA and extending in the direction of the 3' end of the coding sequence. The PCR product extends into the coding sequence to the primer B:474-16 (SEQ ID NO: 10) which lies within the approximately 200 bp amplimer.

PCR was carried out using a GeneAmp DNA Amplification Kit (Perkin Elmer Cetus, Norwalk, Conn.) according to the manufacturer's instructions. Briefly, a 100 µl reaction consisted of the following:

8 µl MgCl$_2$ 25 mM

10 µl 10×PCR buffer 70.8 µl sterile H$_2$O

2 µl dGTP 10 mM

2 µl dATP 10 mM

2 µl dTTP 10 mM

2 µl dCTP 10 mM

1 µl T7:476-30 primer 15 µM

1 µl B:474-16 primer 15 µM 500 ng Rat 1-EJ cDNA library pool DNA

The reaction mix was overlayered with mineral oil (Sigma, St. Louis, Mo.) and placed in a DNA thermal cycler (Perkin Elmer Cetus). Taq polymerase (0.5 µl, 2.5 U) was added in a hot start procedure and the thermal cycler was programmed as follows:

| 1 min | 94° C. | |
|---|---|---|
| 1 min | 59° C. | ] 40 cycles |
| 2 min | 72° C. | |
| 10 min | 72° C. | |
| soak | 4° C. | |

Figure 7:
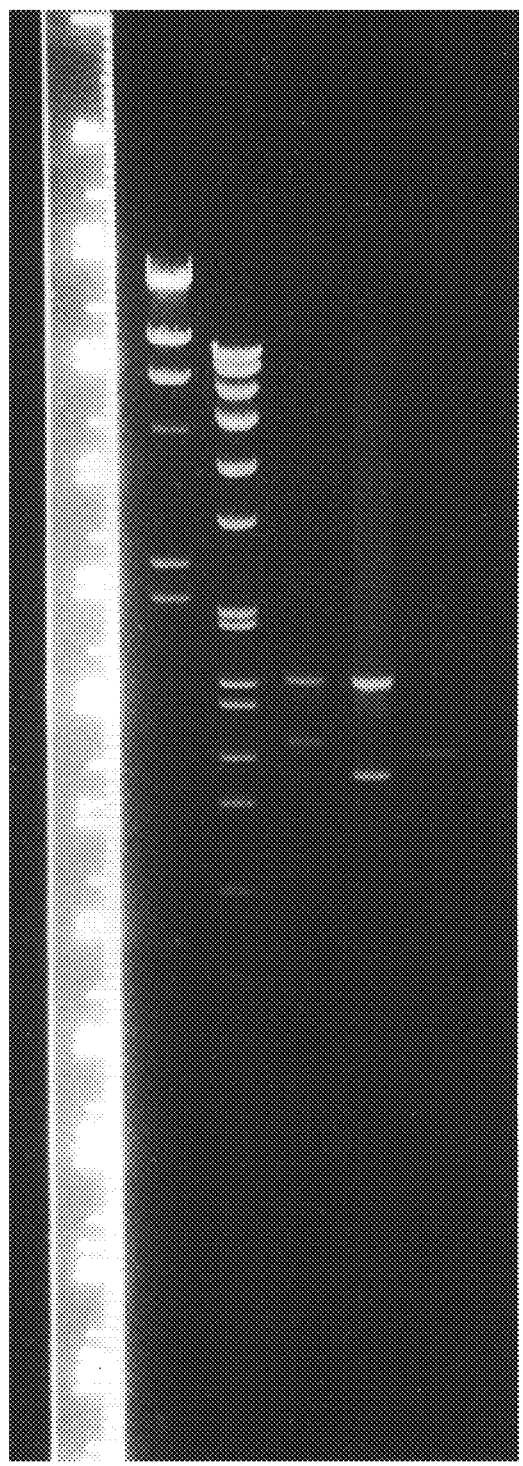
FIG. 7 is a reproduction of an ethidium bromide-stained agarose gel, showing the products obtained after PCR amplification of Rat 1-EJ library cDNA sequences. Lane 1 contains molecular weight standards (Molecular Weight Marker II, Boehringer Mannheim, Indianapolis, Ind.); Lane 2 contains molecular weight standards (Molecular Weight Marker VII, Boehringer Mannheim); Lane 3 contains an aliquot of PCR reaction products resulting from amplification of Rat 1-EJ cDNA using primer T7:476-30 (SEQ ID NO: 11) and primer B:474-16 (SEQ ID NO:10).

An aliquot of the reaction products was analyzed by agarose gel electrophoresis (0.8% agarose in Tris Borate EDTA buffer (TBE) containing ethidium bromide) and the gel was photographed (FIG. 7). One major band at approximately 1200 bp and several smaller minor species were visible on the ethidium bromide-stained gel.

D. Southern Hybridization of PCR Products

After PCR, products from Example 7, Part C, were separated by agarose gel electrophoresis and analyzed by a standard Southern blot procedure. Briefly, the gel was denatured by soaking in 1.5 M NaCl, 0.5 N NaOH for 30 min. The gel was then neutralized by soaking in 1.5 M NaCl, 0.5 M Tris-HCL (pH 7.5) for 30 minutes. The DNA in the gel was transferred to nitrocellulose by capillary action in 10×SSC overnight. After transfer, the nitrocellulose was rinsed in 6×SSC, air dried and crosslinked in a UV Stratalinker (Stratagene, La Jolla, Calif.).

The nitrocellulose was prehybridized, hybridized and probed using an Enhanced Chemiluminescence 3' oligolabelling and Detection System kit (Amersham, Arlington Heights, Ill.) according to the manufacturer's instructions. Prehybridization was carried out at 50° C. for 30 min. Hybridization was carried out for about one and a half hours at 50° C. with approximately 8 ng/ml of oligonucleotide probe A: 474-14 (SEQ ID NO: 9).

After hybridization, the nitrocellulose was washed twice in 5×SSC, 0.1% SDS at room temperature for 5 min each time. Then the nitrocellulose was washed twice in 1×SSC, 0.1% SDS at 50° C. for 15 min each time. Horse Radish Peroxidase Antibody development and ECL detection were carried out according to kit instructions.

Figure 8:
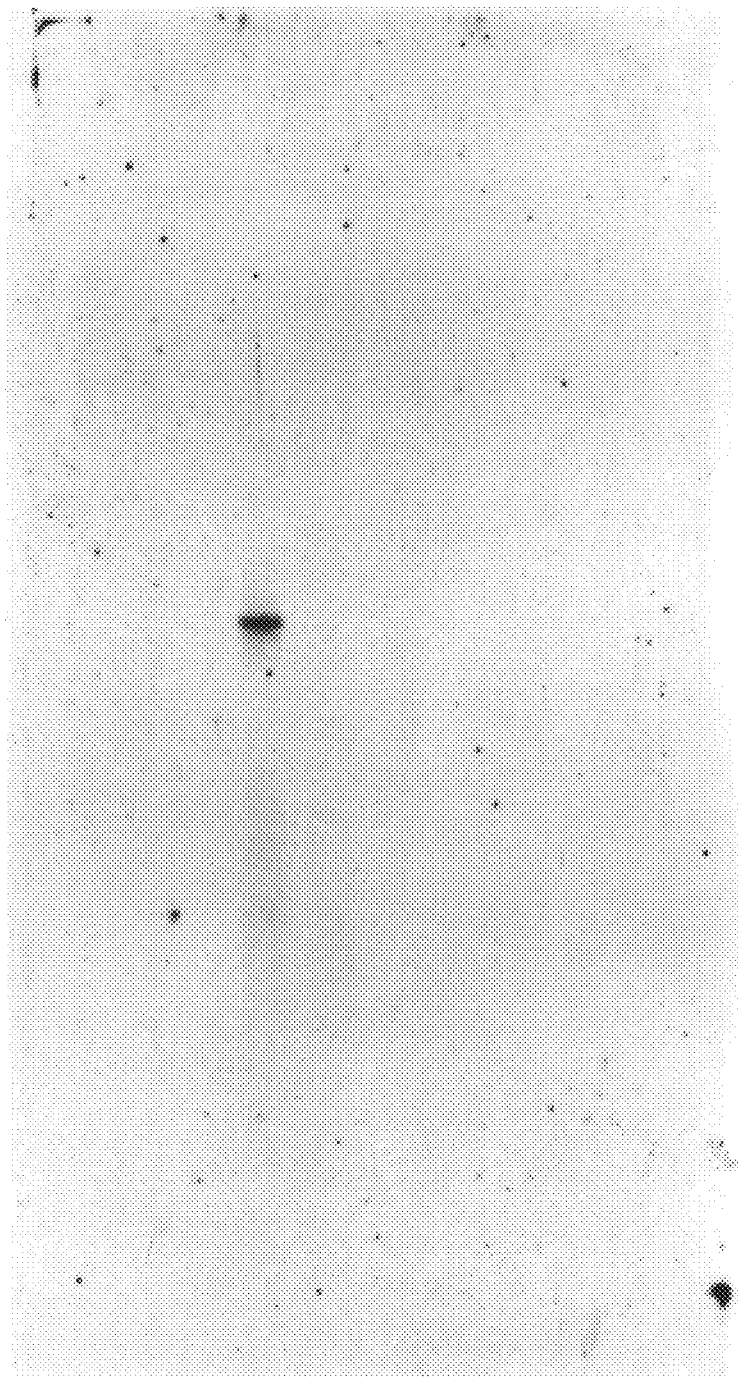
FIG. 8 is a reproduction of an autoradiogram resulting from the Southern hybridization of the DNA transferred from the gel illustrated in FIG. 7 in reverse orientation after it was probed with primer A:474-14 (SEQ ID NO: 9).

The nitrocellulose was exposed to x-ray film at room temperature for 20 minutes. Autoradiography of the nitrocellulose revealed a single band of approximately 2.1 kb (FIG. 8). This specific, but rare, PCR product was not visible on the ethidium bromide-stained gel (FIG. 7).

E. Amplification of Specific PCR Product

Since the specific 2.1 kb PCR product described in Example 7, Part D was present in such minute quantities that it could only be detected by autoradiography, it was amplified by PCR. First, the 2.1 kb PCR product was isolated by cutting a region of an agarose gel in which the specific DNA was expected to have migrated. The DNA was eluted from the gel using an S&S Elu-Quik DNA Purification Kit (Schleicher & Schuell, Keene, N.H.) following the manufacturer's directions. A PCR reaction was carried out on an aliquot of the eluted DNA utilizing primer T7: 476-30 (SEQ ID NO: 11) at the 5' end. The 3' primer was as follows:

485-26 GGGTACGTGTGAATGATATCCAGGTAG (SEQ ID NO: 12) (antisense)

This oligonucleotide sequence lies approximately 350 bp upstream from the 3' end of the 2.1 kb PCR fragment. This sequence was elucidated by sequencing a partial mouse cDNA which was isolated by screening a mouse lymphoma BW 5147 library with the approximately 200 bp PCR amplimer sequence.

A 100 µl PCR reaction using the eluted 2.1 kb PCR fragment as template was prepared as follows:

8 µl MgCl$_2$ 25 mM

10 µl 10×PCR buffer 61.5 µl sterile H$_2$O

2 µl dGTP 10 mM

2 µl dATP 10 mM

2 µl dTTP 10 mM

2 µl dCTP 10 mM

1 µl T7: 476-30 primer 15 µM

1 µl 485-26 primer 15 µM

10 µl eluted 2.1 kb PCR fragment

The reaction mix was treated as described in Example 7, Part C and the thermal cycler was programmed as follows:

| 94° C. | 30 sec | |
|---|---|---|
| 60° C. | 1 min | ] 40 cycles |
| 72° C. | 1 min | |
| 72° C. | 10 min | |
| 4° C. | soak | |

Figure 9:
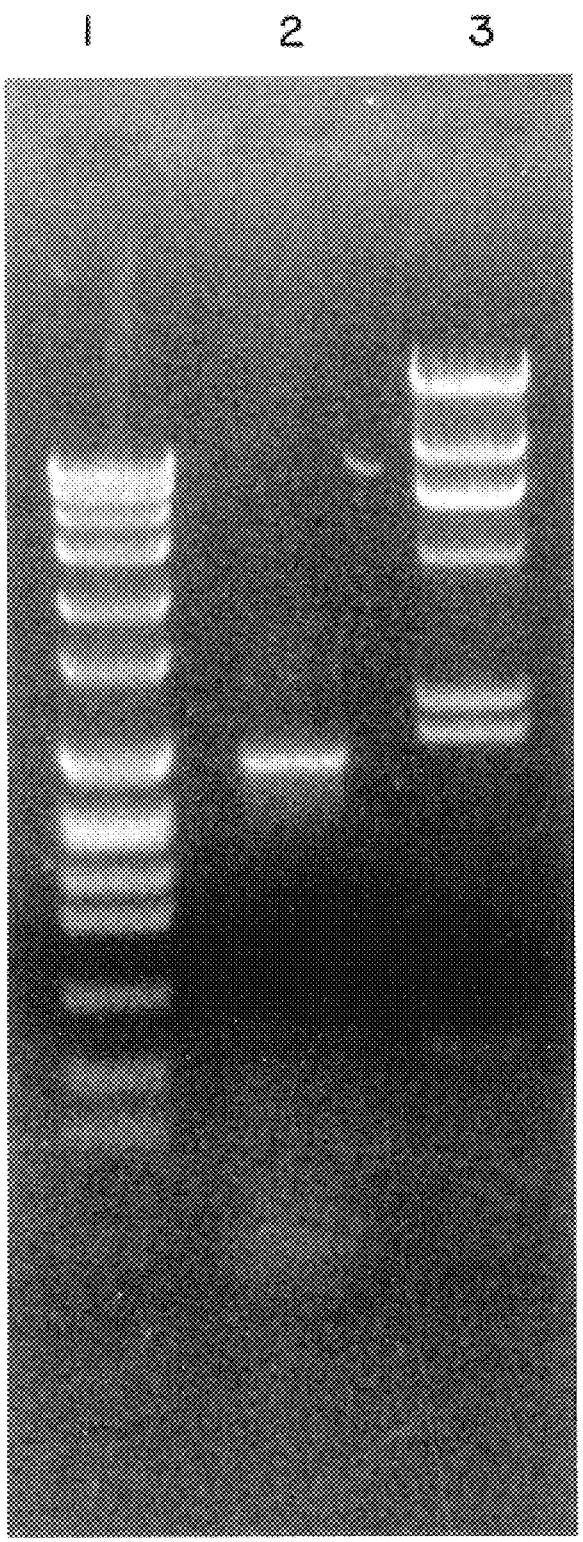
FIG. 9 is a reproduction of an ethidium bromide-stained agarose gel, showing the products obtained after PCR amplification of an approximately 2.1 kb PCR product that was visualized in the autoradiogram in FIG. 8. Lane 1 contains molecular weight standards (Molecular Weight Marker VII, Boehringer Mannheim); Lane 2 contains the PCR products obtained after amplification of the approximately 2.1 kb PCR fragment with primer T7:476-30 (SEQ ID NO: 11) and primer 485-26: (SEQ ID NO: 12); Lane 3 contains molecular weight standards (Molecular Weight Marker II, Boehringer Mannheim).

An aliquot of the reaction products was analyzed by agarose gel electrophoresis (0.8% agarose in TBE containing ethidium bromide) and the gel was photographed (FIG. 9). Analysis of the ethidium bromide-stained gel revealed a single DNA band of approximately 1.8 kb.

F. DNA Sequence Analysis

The approximately 1.8 kb PCR product described in Example 7, Part E was sequenced using Taq DyeDioxy Terminator cycle sequencing kits (Applied Biosystems, Inc., Foster City, Calif.) and an automated DNA sequencer (Applied Biosystems 373A) following the manufacturer's instructions. The PCR fragment was sequenced after it was passed over a Centricon-100 unit (Amicon, Beverly, Mass.) and washed with sterile water. In some instances, sequences were derived after the PCR fragment was subcloned into a pUC13 vector (Promega, Madison, Wis.). Nucleotide sequencing was carried out using synthetic oligonucleotides as primers.

Sequencing of approximately 1750 bp of the PCR fragment and analysis of all possible reading frames revealed overlap with the partial mouse BW 5147 cDNA sequence.

The partial mouse cDNA contained 3' untranslated sequence as well as an open reading frame of approximately 885 bases which would code for approximately 295 amino acids, but no start codon. The sequencing of the PCR fragment extended the open reading frame coding region by an additional approximately 445 amino acid residues and located the methionine specifying ATG start codon. In addition, approximately 300 bp of 5' untranslated region was identified in the PCR fragment.

Alternatively, cDNA clones encoding GlcNAc T-V can be isolated using the following strategy.

Total RNA is prepared in parallel isolations from rat kidney tissue, according to standard procedures, and from mouse lymphoma BW5147 cells and from ascites-grown rat mammary gland MAT-C1 cells, as described in Sambrook et al. (eds.) (1989) supra. ATCC T1B47 is a clone (BW5147.3) of the BW5147 cell line adapted into culture (J. Natl. Cancer Inst. (1973) 51:883; J. Immunol. (1973) 110:1470). MAT C1 cells are described in Carraway et al. (1976) J. Biol. Chem. 251:6173–6178. The Poly(A)+ fraction of the total RNA is prepared by chromatography over Oligo(dT) cellulose chromatography as described in Sambrook et al. (eds.) (1989) supra. Polyadenylated mRNA encoding GlcNAc T-V is included within the Poly(A)+ RNA thus prepared.

cDNA libraries are prepared using the poly(A)+ RNA prepared from rat kidney, mouse lymphoma BW5147 cells, and MAT-B1 cell total RNA according to the procedure of Sambrook et al. (eds.) (1989) supra. Cloning of the cDNA population into a suitable vector (such as λgt11) is done according to standard protocols. (See, e.g., Huynh et al. (1985) in DNA Cloning, a Practical Approach, Vol. 1 (Glover, D. M., ed.), IRL Press, Washington, D.C., pp. 49–78.)

Commercially-available cDNA libraries (e.g., rat kidney cDNA library, Clontech Laboratories, Palo Alto, Calif.) can also be screened for GlcNAc T-V clones.

The cDNA libraries are screened for sequences encoding GlcNAc T-V by plaque hybridization under low stringency conditions using the approximately 200 bp amplimer radiolabelled by random hexamer labelling as described in Sambrook et al. (eds.) (1989) supra. Clones specifically hybridizing the amplimer sequence are selected for further analysis (restriction endonuclease digestion, nucleotide sequence determination).

Genomic clones encoding GlcNAc T-V can be identified from a rat (or mouse or other mammal) genomic library using Primer 1 (SEQ ID NO:5) or Primer 2 (SEQ ID NO:7) e.g., or Primers 1 and 2 in combination, or the amplimer where PCR synthesized as above was primed with Primer 1 (SEQ ID NO: 5) and AntiPrimer 2 (SEQ ID NO:8) to identify appropriate genomic sequences.

From the clones analyzed it is possible to reconstruct the entire coding sequence of GlcNAc T-V. If a full-length coding sequence is not reconstructed, further primers can be designed using sequences near the ends of the sequenced region for use in the RACE procedure (Rapid Amplification of cDNA Ends) as described in Frohman et al. (1988) Proc. Natl. Acad. Sci. USA 85:8998–9002. Where the entire gene is desired, genomic libraries can be screened, and "walking" procedures known in the art are used to extend in both directions.

Example 8
Cloning of a Rat cDNA Sequence Encoding GlcNAc T-V
A. Southern Hybridization of Rat 1-EJ Library Pools Nitrocellulose filters, containing NotI-linearized plasmid DNA from each of the individual 43 pools of the Rat 1-EJ cDNA library, were probed in order to identify which pool(s) contained a full-length GlcNAc T-V cDNA. A cDNA probe was derived from the partial mouse cDNA coding region and was obtained as a HindIII/PstI fragment starting approximately 855 bp down stream from the Rat 1-EJ PCR fragment ATG sequence and extending approximately 650 bp toward the 3' end of the sequence.

The nitrocellulose filters were incubated with prehybridization solution at 42° C. as described in Sambrook et al., (eds.) (1989) supra. Hybridization was then carried out in an overnight incubation using an approximately 650 bp mouse cDNA probe which was labeled with [$\alpha^{32}$P]-dCTP using a Multiprime DNA Labelling System kit (Amersham). The nitrocellulose was then washed and the filters were exposed to X-ray film with an intensifying screen at –80° C. overnight. Autoradiography of the filters revealed 4 positive pools among the 43 screened.

B. PCR Analysis of Rat 1-EJ Library Pools

PCR was carried out using template DNA from each of the 4 positive Rat 1-EJ cDNA library pools identified in Example 8, Part A in order to determine which pool contained a full-length cDNA. The reactions were carried out as described in Example 7, Part C, except that the following primers were used:

Primer 501-16 CCCGTCGACGAGAGCCAAGGGAATG-GTAC (SEQ ID NO: 13) (sense)

Primer 496-2 CCCAGCAGGTACAGAGATGTG (SEQ ID NO: 14) (antisense)

Primer 501-16 (SEQ ID NO: 13) was determined by sequencing the Rat 1-EJ PCR fragment to hybridize in the 5' untranslated region approximately 15 to 35 bases upstream from the ATG start codon. Primer 496-2 (SEQ ID NO: 14) was determined by sequencing to hybridize within the coding region about 900 bases downstream from the ATG start coon. Therefore, PCR with these two primers gives a predicted product of about 900 bp in length covering the 5' end of the coding region. The thermal cycle was programmed as follows:

| 94° C. | 30 sec | |
|---|---|---|
| 55° C. | 1 min | 40 cycles |
| 72° C. | 1 min | |
| 72° C. | 10 min | |
| 4° C. | soak | |

An aliquot of the reaction mixture was separated by agarose gel electrophoresis as described in Example 7, Part C. Analysis of the ethidium bromide-stained gel indicated two of the four pools gave the correct size band (about 900 bp). This information, together with the size of the bands obtained by Southern hybridization of the Rat 1-EJ cDNA library pools (Example 8, Part A) revealed that one pool could contain a full-length GlcNAc T-V cDNA.

C. Colony Hybridization Procedures for Screening a Rat 1-EJ cDNA Library Pool

Transformed E. coli from the glycerol stock of the one pool of the Rat 1-EJ cDNA library identified in Example 8, Part B, above, were spread out at a density of approximately 4,500 colonies per 10×10 cm plate on nutrient plates containing 50 μg/ml Ampicillin. Nitrocellulose filters were used to lift the colonies off the plate. The filters (colony side up) were treated by serially placing them over a piece of Whatman 3 MM paper saturated with each of the following:

1. 1.5 M NaCl, 0.5 N NaOH for 10 min
2. 1.5 M NaCl, 0.5 M Tris-HCl (pH 7.5) for 5 min
3. 2×SSC for 5 min The filters were then air dried and crosslinked by UV irradiation. The filters were then subjected to digestion with Proteinase K by incubating in a solution containing 0.2% SDS, 100 mM Tris-HCl (pH 8.5), 50 mM NaCl, 10 mM EDTA (pH 8) and 50 μg/ml proteinase K at 55° C. for 30 min. The filters were then transferred to a solution containing 5×SSC, 0.5% SDS and 1 mM EDTA (pH 8) and incubated at 55° C. for 30 min. Prehybridization, hybridization and subsequent treatments were carried out using an ECL 3' Oligolabelling and Detection System kit (Amersham) with the following conditions:

1. prehybridization was carried out at 53° C. for approximately 2 hours.
2. hybridization was carried out at 53° C. in an overnight incubation using primer 501-16 (SEQ ID NO: 13) at approximately 7 ng/ml.

After hybridization, the filters were washed as described in Example 7, Part D. After ECL detection, the filters were exposed to X-ray film at room temperature for 4 minutes.

Among the 36,000 colonies screened, 24 individual colonies and mixtures of colonies were picked for further analysis by PCR. PCR was carried out in the same manner as described in Example 8, Part B except that a 20 μl reaction volume was used and the template was obtained by touching a pipet tip to the bacterial plate and then dipping the pipet tip in the PCR mixture. After overlayering with mineral oil, the PCR tubes were incubated in the thermal cycler at 94° C. for 4 min prior to adding 0.2 μl of Taq polymerase. The following temperature regime was applied:

| 94° C. | 30 sec | |
|---|---|---|
| 53° C. | 1 min | |
| 72° C. | 1 min | 25 cycles |
| 72° C. | 10 min | |
| 4° C. | soak | |

An aliquot of the reaction mixture was separated by agarose gel electrophoresis as described in Example 7, Part C. Analysis of the ethidium bromide-stained gel revealed three positives among the 24 mixtures examined.

The 3 positive mixtures were replated and probed with primer 496-2 (SEQ ID NO: 14) as described above. Prehybridization and hybridization, according to instructions in the ECL 3' Labelling and Detection System kit, were carried out at 53° C. for 30 min and approximately 2 hours respectively. Washes were as described above and autoradiography was carried out for 20 min at room temperature. Analysis of the X-ray film revealed one positive among approximately 600 colonies screened. This colony was confirmed by PCR analysis with primers 501-16 (SEQ ID NO: 13) and 496-2 (SEQ ID NO: 14) as described above except the reaction volumes were 50 μl.

The one positive colony mixture from above was replated at low density and probed with primer 496-2 (SEQ ID NO: 14) as described above except prehybridization and hybridization were carried out at 55° C. Filters were exposed to X-ray film for 2 min revealing 7 positives among approximately 300 colonies screened.

D. Sequence Analysis of Rat 1-EJ cDNA

Plasmid DNA was isolated from 4 of the final positive colonies described in Example 8, Part C. Restriction enzyme analysis revealed that the plasmids each contained an approximately 4.8 kb cDNA insert. Nucleotide sequence analysis of one of the plasmids was carried out using the procedures described in Example 7, Part F. Results are shown in FIG. 10A–10E and SEQ ID NO:15–16.

In SEQ ID NO:15, the DNA sequence designated the sense strand of approximately 300 bases in what appears to comprise the 5' untranslated region preceding the translated portion of the rat GlcNAc T-V cDNA. Translation initiates with an ATG beginning at nucleotide 299. The coding region spans 2220 bases and codes for 740 amino acids and a stop codon (TAG) ending at nucleotide 2521. The subsequent sequence appears to be an untranslated 3' region of the rat GlcNAc T-V cDNA. By restriction mapping analysis of the plasmid DNA, this 3' untranslated region of the cDNA appears to be approximately 2300 bases in length.

SEQ ID NO:16 thus provides the primary structure (amino acid sequence) of rat GlcNAc T-V as including 740 specified amino acid residues (estimated M.W.=84,561 without glycosylation).

Example 9

Southern Hybridizations

Appropriate amounts of rat mammary tumor genomic DNA and rat liver genomic DNA were digested in parallel reactions with restriction enzymes (BglII, NcoI, and NcoI/XhaI and BamHI/BglII) according to the instructions of the suppliers. Restriction fragments were then separated by agarose gel electrophoresis (1.0% agarose, Tris-Acetate-EDTA buffer).

The gels were then stained with ethidium bromide, excess stain was removed by soaking in TAE buffer, and the gels were photographed. The DNA in the gels was then depurinated by soaking in 0.25 N HCl for 10 min with agitation.

Prior to transfer to nitrocellulose, the DNA was denatured by soaking the gels in 0.5 N NaOH, 1.5 M NaCl for 30 min. The nitrocellulose was soaked in double distilled water for 20–30 min, and then in 10×SSC for 20–30 min. The gel was rinsed with double distilled water and the base was neutralized by soaking the gel in 0.5 M Tris-HCl (pH 7.4), 3 M NaCl for 30 min.

The DNA bands in the treated gel were then blotted to the nitrocellulose by capillary transfer in 10×SSC overnight at room temperature. The positions of the wells and the orientation of the gel were marked on the nitrocellulose with a #1 pencil.

The nitrocellulose sheet was then rinsed in 4×SSC, air dried for 30 min, and baked in a vacuum oven at 80° C. for 2 hr (until thoroughly dried).

The nitrocellulose was washed with prehybridization solution for 4 hr at 42° C. Hybridization was then carried out in an overnight incubation using an approximately 200 bp amplimer probe which was random-hexamer labeled with [$\upsilon-^{32}P$]-CTP (See Sambrook et al. (eds.) (1989) supra). The approximately 200 bp amplimer was made in a Taq polymerase reaction with Primer 1 (SEQ ID NO:5) and AntiPrimer 2 (SEQ ID NO:8) as described herein. The nitrocellulose was then washed twice with 2×SSC, 0.2% SDS at 50° C. for 30 min each time.

The hybridized nitrocellulose was then placed on X-ray film with an intensifying screen and held overnight at −80° C. to expose the film.

Example 10

Isolation of Partial Mouse Sequences for GlcNAc T-V

PCR was carried out according to standard methods to determine whether Primers 1 and 2 could amplify a specific product from two cell lines (mouse lymphoma BW5147 and rat mammary tumor Mat C1 cells).

Total RNA and poly(A)+RNA was isolated from each cell line, and used as to generate cDNA using reverse transcriptase. These cDNA preparations served as template in parallel PCR reactions as follows:

10–50 ng template cDNA

5 μl 10× Taq buffer (Mg-free)

3 μl 25 MM MgCl$_2$

1 μl dNTP mix (10 mM each)

1 μl 30 μM Primer 1

1 μl 30 μM Primer 2

38 μl sterile water 0.5 μl Taq polymerase

Each reaction was overlayered with oil and then placed in a thermal cycler apparatus with the following temperature regime:

| 5 min | 94° C. | |
|---|---|---|
| 1 min | 94° C. | |
| 1 min | 55° C. | 35–41 cycles |
| 2 min | 72° C. | |
| 10 min | 72° C. | |

The reaction products were then separated by agarose gel electrophoresis (2% agarose)

Example 11

Recombinant GlcNAc T-V Expression

A. Transient Expression of Rat GlcNAc T-V in COS-7 Cells

The entire approximately 4.8 kb cDNA insert from one rat GlcNAc T-V clone described in Example 8, Part D was ligated into an SalI- and NotI-digested pJT-2 plasmid expression vector (Wen et al.(1992) Cell 69:559–572). COS-7 cells (CRL 1651, American Type Culture Collection, Rockville, Md.) were transfected with the pJT-2 plasmid alone or with pJT-2 plasmid containing the rat GlcNAc T-V cDNA insert by electroporation as follows: 4×10$^6$ cells in 0.8 ml of DMEM (Dulbeccol's Modified Minimal Medium, Gibco BRL Life Technologies, Gaithersburg, Md.) and 7.5% FBS (Fetal Bovine Serum, Bocknek, Ltd.) were transferred to a 0.4 cm cuvette and mixed with 10 μg of plasmid DNA in 10 μl of water. Electroporation was performed at room temperature at 1600 volts and 25 μF using a Gene Pulser apparatus (Bio-Rad Laboratories, Hercules, Calif.) with the pulse controller unit set at 200 ohms (Wen et al. (1988) supra). The cells were then diluted into approximately 40 ml of DMEM, 7.5% FBS and transferred to 100 mm culture dishes. After a 17 hr incubation at 37° C., the medium was replaced and incubation continued for an additional 51 hr or 75 hr.

B. Preparation of COS-7 Cells for GlcNAc T-V Activity Assay

The medium from each COS-7 plasmid transfected plate was removed and the cells were rinsed with phosphate-buffered saline (PBS). Cell scrapers were used to collect the cells, which were placed in tubes, diluted with PBS and centrifuged to pellet the cells. After the PBS had been aspirated, the cell pellet was subjected to quick freezing by immersion of the tube in liquid nitrogen. The cells were kept frozen on dry ice until resuspended in buffer for analysis by radiochemical assay and ELISA.

C. Assay of GlcNAc T-V Activity

Cell pellets were resuspended in 20 μl MES (pH 6.0) 150 mM NaCl buffer and disrupted by sonication. The protein content of each extract was determined as described in Example 4. GlcNAc T-V activity was then determined in radiochemical and ELISA assays.

The radiochemical assay uses a synthetic trisaccharide acceptor molecule (Srivastava et al. (1988) supra; Pierce et al. (1987) supra; Arango and Pierce (1988) supra; Palcic et al. (1988) Glycoconjugate J. 5:49–63; Pierce and Arango (1986) J. Biol. Chem. 261:10772–10277; Crawely et al. (1990) Anal. Biochem. 185:112–117). A typical assay mixture contains the following reagents dried under vacuum in a 1.5 ml centrifuge tube: 10$^6$ cpm of UDP-[$^3$H]-GlcNAc (25 cpm/pmol), and 1 mM of the synthetic acceptor in a total volume of 0.01 ml. To initiate the reaction, 0.01 ml of cell extract, typically containing about 30 μg protein, in a buffer containing 50 mM MES (pH 6.0) and 1% Surfact-Amps (Triton) X-100, was added to the assay tube and incubated at 37° C. several hours (e.g., about 7 hrs). To terminate the assay, 0.5 ml H$_2$O was added to each tube, vortexed to mix thoroughly, and then contents of the tubes were centrifuged. Radiolabeled product was separated from unincorporated substrate by virtue of its hydrophobic moiety by C-18 chromatography. Each supernatant was then loaded onto a pellicular C-18 Sep Pak column which had previously been activated with methanol and pre-equilibrated with water. The column was then washed with 200 ml H$_2$O to remove water-soluble radioactivity resulting from unreacted substrate and breakdown products. The radiolabeled product was then eluted with 100% methanol, and radioactivity was measured by liquid scintillation counting. All assays were conducted at least in duplicate for two time points and the results were averaged. The variation between the values from duplicate assays did not exceed plus or minus 5%, and typically were less than plus or minus 2% of the averaged value.

The ELISA assay for GlcNAc T-V activity allows the detection of femtomole amounts of assay product, and the assay range covers a 10$^6$-fold range of GlcNAc T-V activity. This assay utilizes unlabeled sugar nucleotide, the trisaccharide acceptor coupled to bovine serum albumin (BSA), and a rabbit polyclonal antibody specific for the tetrasaccharide-BSA product of the reaction. In order to determine GlcNAc T-V activity, standard calibration curves must be generated in each assay using known amounts of GlcNAc T-V, as measured in the radiochemical assay, and then absorbance in a test sample must be correlated with a particular specific activity by comparison to the standard curve.

An alternate approach to demonstrate that the full-length cDNA clone isolated does encode GlcNAc T-V, the coding sequence is fused to the N-terminal Protein A coding sequence as described in Larsen et al. (1989) Proc. Natl. Acad. Sci. USA 86:8227–8231. The resultant recombinant plasmid is then introduced into mammalian cells such that cells which have incorporated the cDNA sequences survive in culture. Because the fusion protein contains the N-terminal sequences of Protein λ, the fusion protein is directed to the secretion pathway and released from the cells. After removal of the cells by centrifugation, the culture medium is assayed for GlcNAc T-V activity as described herein. A portion of the cell-free medium is chromatographed over an IgG column to which the N-terminal Protein A sequences bind, causing GlcNAc T-V activity to be retained on the column.

A second alternative approach for confirming that the cDNA isolated does encode GlcNAc T-V is to insert the complete cDNA into a vector under the control of regulatory sequences which will allow expression in the chosen mammalian host cells. The host cell chosen is a GlcNAc T-V-deficient variant of the mouse lymphoma BW5147 cell line, which variant is PHA 2.1; this variant cell line is described in Cummings et al. (1982) J. Biol. Chem. 257:13421–13427. An alternative GlcNAc T-V-deficient cell line is the Lec4 variant of CHO cells, described by Stanley, P. (1983) Methods Enzymol. 96:157–184. Both variant cells lines were selected for growth in the presence of the cytotoxic lectin L-phytohemagglutinin, which binds to the galactosylated product of GlcNAc T-V. Expression of the cDNA sequences encoding the GlcNAc T-V restores GlcNAc T-V activity and lectin sensitivity to these variant cell lines.

The use of any one or more of the foregoing approaches provides confirmation that GlcNAc T-V is cloned as cDNA.

Example 12

Determination of CHO GlcNAc T-V Sequence

The sequences for CHO GlcNAc T-V was readily determined using standard molecular biological techniques and the rat sequence information provided herein.

A cDNA library was constructed using mRNA from CHO dhfr⁻ cells using standard procedures. Briefly, total RNA was isolated and poly $(A)^+$ mRNA was selected using an mRNA separator kit (Clontech Laboratories, Palo Alto, Calif.). cDNA was synthesized using a Time-Saver cDNA Synthesis Kit (Pharmacia Biotech, Piscataway, N.J.) using a 3' oligo which encompassed the rat GlcNAc T-V TAG stop codon to enrich for the CHO GlcNAc T-V cDNA.
Primer GCTATAGGCAGTCTTTGC (SEQ ID NO:23) (antisense)

Double-stranded cDNA was ligated into the phage cloning vector lambda gt10 (Promega Corporation, Madison, Wis.) and packaged using Gigapack II Gold Packaging Extract (Stratagene, La Jolla, Calif.). The phage were propagated using the bacterial host strain E. coli C600Hfl.

The CHO cDNA library was screened with a 5'342 bp rat GlcNAc T-V PCR amplimer which hybridizes 14 bp upstream from the ATG start codon and extends 328 nucleotides into the GlcNAc T-V coding region. Positive phage clones were then screened with a 3'320 bp rat GlcNAc T-V PCR amplimer which hybridizes 5 bp upstream from the TAG stop codon and extends into the 3' untranslated region. One putative CHO GlcNAc T-V clone hybridized to both the 5' and 3' rat GlcNAc T-V probes. Sequence analysis of the positive clone after second and third round plaque purification revealed the full length CHO GlcNAc T-V cDNA sequence (FIG. 11A–11F, SEQ ID NO:17)

It is obvious to one normally skilled in the art that Chinese Hamster GlcNAc T-V genomic or cDNA clones can be readily isolated using CHO cell mRNA or DNA, standard molecular biology procedures and the sequence information revealed in FIG. 11A–11F. There would not be a need to practice the procedures described in this example exactly.

Example 13

Determination of Human GlcNAc T-V Sequence

The sequences for human GlcNAc T-V was readily determined using standard molecular biology procedures and the rat GlcNAc T-V sequence information provided herein.

The portion of the GlcNAc T-V cDNA in which rat, mouse and CHO sequences were determined was analyzed, and specific oligonucleotides were designed covering areas where the rat, mouse and CHO sequences were identical:
Primer 663-11 TGTAGGAGACAGAATCGTTGAGC (SEQ ID NO:24) (sense)
Primer 663-12 CCGGCACAACTGAAGAGCAGG (SEQ ID NO:25) (antisense)

PCR was carried out using a GeneAmp RNA PCR Kit (Perkin Elmer Cetus, Norwalk, Conn.) according to the manufacturer's instructions. In the first step human kidney total RNA (Clontech Laboratories #64060-1) was converted to cDNA using Reverse Transcriptase. After the RNA was converted to cDNA, it was amplified by PCR using primers 663-11 (SEQ ID NO:24) and 663-12 (SEQ ID NO:25). An aliquot of the reaction products was analyzed by agarose gel electrophoresis and the single band of the expected size of approximately 1125 bp was excised. The PCR product was isolated from the gel using an S&S Elu-Quick DNA Purification Kit (Schleicher & Schuell, Keene, N.H.). The DNA was sequenced directly using the amplification primers 663-11 (SEQ ID NO:24) and 663-12 (SEQ ID NO:25). After the initial sequencing additional oligonucleotide primers were designed using the human PCR sequence to complete the sequencing of the 1125 bp fragment.

The human GlcNAc T-V sequence upstream from the kidney PCR product was obtained by amplifying sequences in a commercially available human placenta cDNA library (Stratagene, #936203). Specific oligonucleotide primers from the human kidney PCR sequence were used as the 3' end antisense primers and a primer covering the T7 promoter sequence of the library cloning vector λZAPII (Stratagene) was used as the 5' end sense primer. PCR was carried out using the following primers:
Primer T7:689-30 CGCGTAATACGACTCACTATAGGG (SEQ ID NO:26) (sense)
Primer 682-19 GTTGTCTGGGGTATGAGGGAAC (SEQ ID NO:27) (antisense)

Additional sequences further upstream were obtained by PCR of the human placenta cDNA library using the Primer T7:689-30 (SEQ ID NO:26) at the 5' end and the following primer at the 3' end:
Primer 710-1 GACTTGATTGCTTGGATCCATGC (SEQ ID NO:28) (antisense)

A comparison of the rat GlcNAc T-V sequence with the human sequence obtained by PCR of the human placenta cDNA library revealed that the human sequence lacked 14 bp from the ATG initiation codon. In order to obtain the extreme 5' end of the human GlcNAc T-V sequence, PCR was carried out using a sense primer designed to hybridize to sequences obtained from a portion of human GlcNAc T-V genomic DNA. The 5' primer sequence was as follows:
Primer 734-16 GTTAAGAGCCAAGGACAGGTGAAG (SEQ ID NO:29) (sense)

The 3' antisense primer designed from sequences within the human placenta PCR product was as follows:
Primer 734-17 AGGGTAGCCGTCCATAGGAGGC (SEQ ID NO:30) (antisense)

The human GlcNAc T-V sequence downstream from the approximately 1125 bp kidney PCR product was obtained by amplifying sequences in the human placenta cDNA library using a specific oligonucleotide primer from the human kidney PCR sequence as the 5' end sense primer and a primer covering the T3 promoter sequence of the library cloning vector λZAPII (Stratagene) as the 3' end antisense primer. PCR was carried out using the following primers:
Primer 689-1 CCATGGTATCCTCAGTGGACGG (SEQ ID NO:31) (sense)
Primer T3:689-31 GCGCAATTAACCCTCACTAAAGGG (SEQ ID NO:32) (antisense)

The PCR products obtained by amplification of the human placenta cDNA library were analyzed by agarose gel electrophoresis and the appropriate bands were excised. The DNA was isolated using the S&S Elu-Quick DNA Purification Kit (Schleicher & Schuell) and the fragments were subcloned into the vector pCRII using the TA Cloning Kit (Invitrogen, San Diego, Calif.) prior to sequencing.

Example 14

Secretion of Enzymatically Active Soluble GlcNAc T-V

A. Construction of a Vector Engineered to Express Secretable GlcNAc T-V.

Soluble, secreted recombinant rat GlcNAc T-V with enzymatic activity was produced by the methods described in U.S. Pat. No. 5,032,519, "Method for Producing Secretable Glycosyltransferases and Other Golgi Processing Enzymes," J. Paulson et al., Jul. 16, 1991. Briefly, the membrane anchor domain and the Golgi apparatus retention signal are deleted and the sequence information for expressing a cleavable secretion signal are inserted in the GlcNAc T-V genetic material. After transfection of the modified GlcNAc T-V sequences into cells, the cells secrete into the culture media soluble enzymatically active GlcNAc T-V. The GlcNAc T-V can be readily purified from the culture media for further use.

Using standard procedures and following the teachings of the cited patent, the cleavable signal sequence of human gamma-interferon was fused with the rat GlcNAc T-V at the sequence corresponding to amino acid number 70 of SEQ ID NO:16. This chimera has replaced the GlcNAc T-V putative cytoplasmic domain (amino acids 1–13), transmembrane domain (amino acids 14–30) and a portion of the stem region (amino acids 31–69) with a fragment coding for the 23 amino acid signal peptide and first amino acid of mature human gamma-interferon. The resulting fusion gene product is cleaved to yield secretable GlcNAc T-V containing one amino acid from the gamma-interferon (Gln) at the new $NH_2$-terminus.

PCR was carried out using rat GlcNAc T-V cDNA in the plasmid pSPORT described in Example 8, Part D with the following primers:

Primer 553-28 (sense) CGCGCTCTAGATGCAAAGATGAAATACACCTCTTACATTTTGGCTTTCCAATTGTGTATTGTTTTGG GTTCTTTGGGTTGTTACTGTCAGGATGGCCCGTATGCCGGTGTC (SEQ ID NO:33)

Primer 516-5 (antisense) GCGGTCGACCTACTATAGGCAGTCTTTGCAGAGGG (SEQ ID NO:34)

Primer 553-28 (SEQ ID NO:33) contains the gamma-interferon signal sequence, one amino acid of the mature gamma-interferon and joins into the rat GlcNAc T-V sequence at amino acid 70. Primer 516-5 (SEQ ID NO:34) contains the rat GlcNAc T-V carboxy-terminal sequence and the TAG stop codon. After 20 cycles, the PCR products were cleaned using a PCR Magic Prep Kit (Promega Corporation) and a portion of the resulting sample was digested with XbaI and SalI. The restriction endonuclease digested sample was analyzed by agarose gel electrophoresis, and the approximately 2.1 kb PCR product was excised. The DNA was isolated using an S&S Elu-Quick DNA Purification Kit (Schleicher & Schuell) and ligated to an XbaI/SalI cut mammalian expression vector overnight at 16° C. using T4 DNA ligase (Boehringher Mannheim, Indianapolis, Ind.). A portion of the ligation mixture was electroporated into *E. coli* DH10B cells as described in Example 7, Part A. Plasmid DNA that contained the correct insert was isolated from eight bacterial colonies using a Plasmid Midi Kit (Qiagen Inc., Chatsworth, Calif.).

B. Transient Expression of Secreted GlcNAc T-V in COS-7 cells.

COS-7 cells were transfected with the mammalian expression vector containing the secretable rat GlcNAc T-V cDNA insert by electroporation as described in Example 11, Part A, except that 15 $\mu$l of plasmid DNA was used for each of the eight clones described above. The cells were transferred to T-75 culture flasks containing 10 ml of DMEM, 10% FBS (fetal bovine serum) and a 1× solution of Glutamine, Penicillin and Streptomycin (Irvine Scientific, Santa Ana, Calif.; final concentrations in medium: L-Glutamine 0.292 mg/ml; Penicillin G, 100 units/ml; Streptomycin sulfate 100 $\mu$g/ml) After a 7 hour incubation at 37° C., the medium was replaced with 7 ml of DMEM, 1% FBS and 1×GPS and incubation continued for an additional 3 days. The cell conditioned medium from each COS-7 plasmid transfection flask was collected and centrifuged to pellet cells and debris. The clear supernatant was frozen at −70° C. until analyzed by radiochemical assay as described in Example 11, Part C.

The results obtained from analysis of 10 $\mu$l of cell conditioned supernatant indicated that four of the transfected clones (A, B, F and H) made little or no active soluble GlcNAc T-V (≦50 pmol/mg×hr) while four of the transfected clones made the following amounts of active soluble GlcNAc T-V:

C=420 pmol/mg×hr

D=470 pmol/mg×hr

E=320 pmol/mg×hr

G=250 pmol/mg×hr

Clone D was chosen for further analysis because it gave the highest enzyme activity in the radiochemical assay. The portion of the mammalian expression vector that carried the PCR derived insert was sequenced in both directions as described in Example 7, Part F. For Clone D, the human gamma-interferon signal sequence joined to the truncated rat GlcNAc T-V sequence was found to be 100% identical to the expected sequence.

C. Stable Expression of Secreted GlcNAc T-V in CHO dhfr$^-$ Cells.

The secreted rat GlcNAc T-V expression vector, clone D from above, was transfected into CHO dhfr$^-$ cells by the calcium phosphate precipitation method (Graham and van der Eb, *Virology* (1973) 52:456–467) modified as described by Wigler et al. (*Cell* (1978) 41:725–731) and Lewis et al. (*Somatic Cell Genetics* (1980) 6:333–347). Following selection by growth in media containing 5% dialyzed FBS (Irvine Scientific), pools and clones of stably transfected CHO dhfr$^-$ cells were obtained. Cell conditioned media from the transfected CHO dhfr$^-$ cell lines were collected and analyzed by the radionucleotide assay as described in Part B. The CHO dhfr$^-$ cell line which produced the highest amount of active soluble GlcNAc T-V as determined by the radiochemical assay (709 pmol/mg×hr) was used to seed a spinner cell culture flask. The cells were propagated in suspension cell culture and then used to seed roller bottles at an initial seeding density of $2.5\times10^7$ cells in 200 ml of a 50/50 mixture of DMEM and F-12 media (Gibco) supplemented with 5% dialyzed FBS, 1× non-essential amino acids (Gibco) and 2 mM L-glutamine (Gibco). After three days the roller bottles were shifted to 200 ml of serum-free medium. Harvests were collected at 6-day intervals with new serum-free medium added after each harvest. In total, 62 liters of conditioned medium were harvested and concentrated to 2.4 liters by cross-flow ultrafiltration through Mini Sartocon polysulfone modules (Sartorius Corporation, Bohemia, N.Y.) then stored at −80° C. prior to purification. Radionucleotide assays were carried out as described in Example 3 to analyze the GlcNAc T-V activity in the concentrated conditioned medium; the results demonstrated that approximately 26 units of total enzyme activity were produced.

Example 15

Purification of Soluble GlcNAc T-V.

The 20-fold concentrated cell conditioned medium described in Example 14 was the starting material for soluble GlcNAc T-V purification.

A. Assay methods.

GlcNAc T-V was assayed using a radiochemical method and the synthetic trisaccharide acceptor as described hereinabove. A 10 $\mu$l aliquot of UDP-GlcNAc, 0.4 mM acceptor, 1 mM ADP and about $5\times10^5$ cpm radiolabeled UDP-GlcNAc was dried in each assay tube. To perform an assay, 5μ2× assay buffer (50 mM MES, pH 6.5; 20% glycerol; 0.5% Triton X-100; 0.5 mg/ml Bovine serum albumin; 150 mM NaCl) was added, and the reaction was initiated by adding 5 μl sample. The reaction was incubated at 37° C., 60 min. Reacted radiolabeled materials are separated from unreacted materials by chromatography over a $C_{18}$ hydrophobic column.

Protein assays were carried out using the BCA microtiter plate assay method. SDS-PAGE was done using 10% (1.5 mm thickness) gels on a Bio-Rad mini gel system.

B. Soluble Enzyme Purification.

The twenty-fold concentrate of the culture medium containing soluble, secreted GlcNAc T-V was thawed, and during thawing EDTA was added to a final concentration of 5 mM. Then this solution was dialyzed against Buffer X (50 mM MES, pH 6.5, 100 mM NaCl) to remove low molecular weight components and EDTA, which would interfere with the copper-chelating column.

Approximately 20 ml of the dialyzed 20× conditioned medium was loaded directly on a 5 ml Hitrap copper-chelating column (Pharmacia, Piscataway, N.J.) which had been pre-equilibrated with Buffer X. The column was washed and then eluted using a 0–20 mM linear gradient of imidazole in Buffer X. Fractions were assayed for GlcNAc T-V activity, and the active fractions were pooled, and EDTA was added to a concentration of 5 mM.

The pooled fractions from the copper chelating column were diluted at least two-fold in Buffer Y and applied to a CM fast flow Sepharose column (1.1×15 cm), (cation exchange column, Pharmacia) which had been pre-equilibrated with Buffer Y (50 mM MES pH 6.5, 5 mM EDTA). GlcNAc T-V was eluted using a 0–500 mM gradient of NaCl in Buffer Y. Soluble GlcNAc T-V eluted at a NaCl concentration of about 300 mM.

We claim:

1. A non-naturally occurring DNA molecule comprising a nucleotide sequence encoding a polypeptide having N-acetylglucosaminyl transferase V (GlcNAc T-V) activity.

2. The DNA molecule of claim 1 wherein said sequence encodes a mammalian GlcNAc T-V.

3. The DNA molecule of claim 2 wherein said nucleotide sequence encodes human GlcNAc T-V.

4. The DNA molecule of claim 3 wherein said nucleotide sequence encodes a polypeptide having an amino acid sequence as given in SEQ ID NO:20.

5. The DNA molecule of claim 4 wherein said nucleotide sequence is as given in SEQ ID NO:19, from nucleotide 38 to nucleotide 2263.

6. The DNA molecule of claim 2 wherein said nucleotide sequence encodes hamster GlcNAc T-V.

7. The DNA molecule of claim 6 wherein said nucleotide sequence encodes a polypeptide having an amino acid sequence as given in SEQ ID NO:18.

8. The DNA molecule of claim 7 wherein said nucleotide sequence is as given in SEQ ID NO:17, from nucleotide 145 to nucleotide 2367.

9. A DNA molecule comprising the DNA sequence of claim 1 and further comprising an exogenous nucleotide sequence.

10. The DNA molecule of claim 9 wherein said exogenous nucleotide sequence is an expression vector.

11. The recombinant DNA molecule of claim 10 wherein said nucleotide sequence encoding a polypeptide having N-acetylglucosaminyl transferase activity is selected from the group consisting of SEQ ID NO:17 from nucleotide 145 to nucleotide 2367 and SEQ ID NO:19 from nucleotide 38 to nucleotide 2263.

12. A recombinant host cell comprising the DNA molecule of claim 9.

13. The recombinant cell of claim 12 wherein said cell is a bacterial cell.

14. The recombinant cell of claim 13 wherein said bacterial cell is *Escherichia coli*.

15. The recombinant cell of claim 12, wherein said cell is a mammalian cell.

16. The recombinant cell of claim 15 wherein said cell is a COS-7 cell.

17. The recombinant cell of claim 15 wherein said nucleotide sequence encodes human GlcNAc T-V.

18. The recombinant cell of claim 17, wherein said nucleotide sequence encodes GlcNAc T-V having an amino acid sequence as given in SEQ ID NO:20.

19. The recombinant cell of claim 18, wherein said nucleotide sequence is as given in SEQ ID NO:19, from nucleotide 38 to nucleotide 2263.

20. The recombinant cell of claim 15 wherein said nucleotide sequence encodes hamster GlcNAc T-V.

21. The recombinant cell of claim 20, wherein said nucleotide sequence encodes GlcNAc T-V having an amino acid sequence as given in SEQ ID NO:18.

22. The recombinant cell of claim 21, wherein said nucleotide sequence is as given in SEQ ID NO:17, from nucleotide 145 to nucleotide 2367.

23. A method for producing a polypeptide having N-Acetylglucosaminyl transferase V activity (GlcNAc T-V), said method comprising the steps of:

(a) operably linking a nucleotide sequence encoding a polypeptide having GlcNAc T-V activity to an expression control sequence to form a GlcNAc T-V expression cassette;

(b) transforming or transfecting a cell to contain the GlcNAc T-V expression cassette of step (a) to form a GlcNAc T-V recombinant cell; and (c) culturing the GlcNAc T-V recombinant cell of step (b) under conditions appropriate for expression of said GlcNAc T-V expression cassette, whereby said nucleotide sequence directs expression of a polypeptide having GlcNAc T-V activity.

24. The method of claim 23 wherein said nucleotide sequence encodes a mammalian GlcNAc T-V.

25. The method of claim 24 wherein said nucleotide sequence encodes human GlcNAc T-V.

26. The method of claim 25 wherein said nucleotide sequence encodes a polypeptide having an amino acid sequence as given in SEQ ID NO:20.

27. The method of claim 26 wherein said nucleotide sequence is as given in SEQ ID NO:19, from nucleotide 38 to nucleotide 2263.

28. The method of claim 24 wherein said nucleotide sequence encodes hamster GlcNAc T-V.

29. The method of claim 28 wherein said nucleotide sequence encodes a polypeptide having an amino acid sequence as given in SEQ ID NO:18.

30. The method of claim 29 wherein said nucleotide sequence is as given in SEQ ID NO:17, from nucleotide 145 to nucleotide 2367.

31. A non-naturally occurring DNA molecule for use in producing a polypeptide having GlcNAc T-V activity, said molecule comprising:

(a) a portion of said non-naturally occurring DNA molecule having a DNA sequence encoding a polypeptide having an amino acid sequence as given in one of SEQ ID NO:18 and 20, (b) a portion of said non-naturally occurring DNA molecule having a DNA sequence capable of hybridizing to a DNA sequence selected from the group consisting of SEQ ID NO:15, SEQ ID NO:17 and SEQ ID NO:19, and which sequence encodes a polypeptide having GlcNAc T-V activity, or (c) a portion of said non-naturally occurring DNA molecule having a DNA sequence encoding a soluble GlcNAc T-V.

* * * * *

UNITED STATES PATENT AND TRADEMARK OFFICE
CERTIFICATE OF CORRECTION

PATENT NO. : 6,015,701

DATED : January 18, 2000

INVENTOR(S) : Pierce et al.

It is certified that error appears in the above-identified patent and that said Letters Patent is hereby corrected as shown below:

In Column 18, line 38, please delete "$\mu$mole/" and replace with --nmole/--.
In Column 28, line 46, please delete "[$^{\upsilon-32}$P]" and replace with --[$^{\alpha-32}$P]--.
In Column 29, line 1, please delete "MM" and replace with --mM--.

Signed and Sealed this

Sixth Day of March, 2001

Attest:

NICHOLAS P. GODICI

Attesting Officer

Acting Director of the United States Patent and Trademark Office